(12) United States Patent
Johnson et al.

(10) Patent No.: US 8,046,198 B2
(45) Date of Patent: Oct. 25, 2011

(54) METHODS FOR DETERMINING SUSCEPTIBILITY TO DEVELOPMENTAL DISORDERS DUE TO A COMBINATION OF GENETIC AND ENVIRONMENTAL FACTORS

(75) Inventors: William G. Johnson, Short Hills, NJ (US); Edward Scott Stenroos, Harrison, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 1151 days.

(21) Appl. No.: 11/165,253

(22) Filed: Jun. 23, 2005

(65) Prior Publication Data

US 2006/0160104 A1 Jul. 20, 2006

Related U.S. Application Data

(62) Division of application No. 09/577,266, filed on May 23, 2000, now Pat. No. 6,912,492.

(60) Provisional application No. 60/136,198, filed on May 25, 1999.

(51) Int. Cl.
*G06F 17/10* (2006.01)
(52) U.S. Cl. ............... 703/2; 702/20; 702/19; 435/6
(58) Field of Classification Search .................. None
See application file for complete search history.

(56) References Cited

U.S. PATENT DOCUMENTS

| 6,210,950 | B1 | 4/2001 | Johnson et al. | |
|---|---|---|---|---|
| 6,218,120 | B1 | 4/2001 | Rozen et al. | |
| 6,274,564 | B1 | 8/2001 | Sarill et al. | |
| 2005/0197285 | A1* | 9/2005 | Rosen et al. | 514/12 |
| 2007/0031853 | A1* | 2/2007 | Stanton et al. | 435/6 |

FOREIGN PATENT DOCUMENTS

| WO | 90/02203 A1 | 3/1990 |
|---|---|---|
| WO | 99/01560 A1 | 1/1999 |
| WO | 00/04194 A1 | 1/2000 |

OTHER PUBLICATIONS

Metz J, Am J Hematol (Apr. 1995);48(4):251-5.
Molloy AM, Lancet (May 31, 1997);349(9065):1591-3.
Morita H, Circulation (Apr. 15, 1997)95(8):2032-6.
Naurath HJ, Lancet(Jul. 8, 1995);346(8967):85-9.
O'Callaghan E, Br J Psychiatry(Jun. 1991); 158:764-9.
Owen MJ, Psychol Med May 1992;22(2)289-93.
Pauls DL, Adv Neurol 1992;58:151-7.
Pyper CM.box-solid. Eur J Contracept Reprod Health Care Jun. 1997;2(2):131-46.
Regland B, J Neural Transm Gen Sect 1994;98(2):143-52.
Reynolds EH, Lancet Jul. 28, 1984;2(8396):196-8.
Sanders TA, Reddy S, Am J Clin Nutr May 1994;59(5 Suppl):1176S-1181S.
Scholl TO, Am J Clin Nutr Apr. 1996;63(4):520-5.
Schorah CJ, Wild J, Lancet May 29, 1993;341 (8857):1417.
Shapiro RM, Schizophr Res Oct. 1993;10(3):187-239.
Shen F, Biochemistry Feb. 8, 1994;33(5):1209-15.
Sherrington R, Nature Nov. 10, 1988;336(6195):164-7.
Shevell MI, Rosenblatt DS, Can J Neurol Sci Nov. 1992;19(4):472-86.
Spielman RS, Am J Hum Genet Mar. 1993;52(3):506-16.
Susser E, Arch Gen Psychiatry Jan. 1996;53(1):25-31.
Susser ES, Lin SP, Arch Gen Psychiatry Dec. 1992;49(12):983-8.
Terwilliger JD, Ott J, Hum Hered 1992;42(6):337-46.
Torrey EF, Bowler A, Schizophr Bull 1990;16(4):591-604.
Torrey EF, Schizophr Bull 1993;19(3):557-62.
Trakatellis A, Postgrad Med J Oct. 1997;73(864):617-22.
van der Put NM, Lancet Oct. 21, 1995;346(8982):1070-1.
Weiffenbach B, Genomics May 1991;10(1):173-85.
Weinberg CR, Wilcox AJ, Lie RT.box-solid. Am J Hum Genet Apr. 1998;62(4):969-78.
Weinberger DR, Arch Gen Psychiatry Jul. 1987;44(7):660-9.
Whitehead AS, QJM Nov. 1995;88(11):763-6.
Wilcox AJ, Am J Epidemiol Nov. 1, 1998;148(9):893-901.
Wilcox AJ, Hum Reprod Feb. 1998;13(2):394-7.
Wouters MG, Feltil Steril Nov. 1993;60(5):820-5.
Yang JK, J Mol Biol Jun. 25, 1984;176(2):169-87.
Arinami et al., American Journal of Medical Genetics, 74:526-528 (1997).
Brown et al., Journal of Nervous and Mental Disease, 184:71-85 (1996).
Chen et al., Journal of Biological Chemistry, 259:3933-3943 (1984).
Lewis et al., Annals of Pharmacotherapy, 32:1087-1095 (1998).
Pauling, Journal of Nutritional & Environmental Medicine, 5:187-198 (1995).
Naurath et al., Lancet (North American Edition), 346:85-89 (1995).
Regland et al., J. Neural Transm, 104:931-941 (1997).
Database EMBL 'Online? Acc. nb. AA744384, Jan. 19, 1998 abstract only.
Noe et al., The Journal of Biological Chemistry, 274:27807-27814 (1999).
Noe et al., Abstract for the Animal Meeting of the RNA Society, 2000, Dept. of Biochemistry, School of Pharmacy, University of Barcelona and Dept. of Biological Sciences, Columbia University (2000).
Christensen et al. Genetic polymorphisms in methyltetrahydrofolate reductase and methionine synthase, filate levels in red blood cells, andrisk of neural tube defects. Am. J. Medical Genetics (May 21, 1999) vol. 84 (2), pp. 151-157.
Wilson et al. A common variant in methionine synthase reductase combined with low cobalamin (vitamin B12) increases risk for spina bifida. Molecular Genetics and Metabolism (Aug. 1999) vol. 67 (4), pp. 317-323.
Maggio et al. Effects of methylfolate in the treatemtn of heterozygous beta-thalassemia patients. Current Therapeutic Research. 1994. vol. 55, No. 12, pp. 1471-1476, abstract only.

(Continued)

*Primary Examiner* — Carolyn L. Smith
(74) *Attorney, Agent, or Firm* — Fox Rothschild LLP

(57) ABSTRACT

The present invention discloses a novel method for identifying an individual who may be susceptible to develop a developmental disorder. In one particular example, an individual is identified who is genetically susceptible to becoming schizophrenic. In addition, the present invention discloses a novel method for identifying individuals who are genetically susceptible to have offspring with a developmental disorder. Methods of diagnosing, preventing and treating developmental disorders such as schizophrenia are also provided.

11 Claims, 5 Drawing Sheets

OTHER PUBLICATIONS

Steen et al. Neural-tube defects are associated with low concentrations of cobalamin (vitamin B12) in amniotic fluid. Prenatal Diagnosis. 1998. vol. 18, No. 6, pp. 545-555.
Allen LH, Am J Clin Nutr (Nov. 1995);62(5):1013-9.
Anderson JL, J Am Coll Cardiol(Nov. 1997);30(5):1206-11.
Andreasen NC, Science(Oct. 14, 1994),266(5183):294-8.
Baird DD, Hum Reprod(Dec. 1997)12(12):2607-13.
Baron M, Acta Psychiatr Scand (Aug. 1995);92(2):81-6.
Bassett AS, Br J Psychiatry(Sep. 1992)161:323-34.
Bates CJ, Eur J Clin Nutr (Sep. 1994)48(9):660-8.
Benjamin J, Gershon ES, Biol Psychiatry (Sep. 1, 1996)40(5):313-6.
Bogerts B, Arch Gen Psychiatiy(Aug. 1985)42(8):784-91.
Boyd JH, Schizophr Bull(1986),12(2):173-86.
Carmel R, Arch Intern Med(Nov. 1987);147(11):1995-6.
Carpenter WT Jr, Buchanan RW, N Engl J Med(Mar. 10, 1994);330(10):681-90.
Chatkupt S, Am J Med Genet(Nov. 1, 1992)44(4):508-12.
Cooper BA, Rosenblatt DS, Annu Rev Nutr (1987);7:291-320.
Detera-Wadleigh SD, Nucleic Acids Res (Aug. 11, 1989);17(15):6432.
Dohrenwend BP, Science (Feb. 21, 1992);255(5047):946-52.
Duff EM, Cooper ES, Am J Public Health (Mar. 1994)84(3):473-6.
Eaton WW, Schizophr Res(Mar. 1992);6(3):181-92.
Falk CT, Rubinstein P, Ann Hum Gene(Jul. 1987); 51 (Pt 3):227-33.
Feder JN, Nucleic Acids Res(Jul. 24, 1987); 15(14):5906.
Fermo I, Ann Intern Med(Nov. 15, 1995);123(10):747-53.
Freeman JM, N Engl J Med(Mar. 6, 1975);292(10):491-6.
Gadowsky SL, J Adolesc Health (Jun. 1995);16(6):465-74.
Gilliam TC, Genomics (Nov. 1989);5(4):940-4.
Godfrey PS, Lancet(Aug. 18, 1990);336(8712):392-5.
Gordon N, Brain Dev (Sep.-Oct. 1995);17(5):307-11.
Gottesman II, Clin Genet (Jul. 1994);46(1 Spec No):116-23.
Grant SF, Nat Genet (Oct. 1996);14(2):203-5.
Green MF, Psychiatry Res(Aug. 1994); 53(2):119-27.
Guaraldi GP, Ann Clin Psychiatiy(Jun. 1993)5(2):101-5.
Heutink P, Am J Hum Genet(Aug. 1995);57(2):465-73.
Hitzig WH, Ciba Found Symp(1978)(68):77-91.
Horie N, Cell Struct Funct(Jun. 1995):20(3):191-7.
Hornsby PP, Epidemiology(Mar. 1998);9(2):193-8.
Jeste DV, Br J Psychiatiy(Oct. 1988); 153:444-59.
Kendall RE, Kemp IW, Arch Gen Psychiatry(Oct. 1989)46(10):878-82.
Kendall RE, Adams W, Br J Psychiatry(Jun. 1991);158:758-63.
Kirch DG, Schizophr Bull (1993);19(2):355-70.
Kirke PN, Q J Med (Nov. 1993)86(11):708-8.
Kovelman JA, Scheibel AB, Biol Psychiatry(Dec. 1984);19(12):1601-21.
Lewis BA, Behav Genet (May 1993);23(3):291-7.
Li N, Biochim Biophys Acta(Oct. 18, 1994);1219(2):515-20.
Lombroso PJ, J Am Acad Child Adolesc Psychiatry (Sep. 1994);33(7):921-38.
Louis-Ferdinand RT, Adverse Drug React Toxicol Rev (1994 Winter);13(4):193-206.
McPartlin J. Lancet(Jan. 16, 1993); 341(8838):148-9.
Mednick SA, Arch Gen Psychiatry (Feb. 1988);45(2):189-92.

* cited by examiner

FIG. 1

Primers for PCR Amplification the DHFR Deletion Polymorphism Region

Forward primer(SEQ ID NO:38):    5'-CTA AAC TGC ATC GTC GCT GTG-3'

Reverse primer(SEQ ID NO:39):    5'-AAA AGG GGA ATC CAG TCG G-3'

Genotypes of the DHFR 19 bp Deletion by Non-Polyacrylamide Gel Electrophoresis

FIG. 3

Sequences of PCR Amplification Products
in the Region of the DHFR Deletion Polymorphism Region

```
                                           *
Allele 1  GCTGCCCACGGTCGGGGTACCTGGGCGGGACGCGCCAGGCCGACTCCCGGCGAGA
          |||||||||||||||||||||                |||||||||||||||||||
Allele 2  GCTGCCCACGGTCGGGGT...................GGCCGACTCCCGGCGAGA
```

FIG. 4A

```
   1 CTGCAGCGCC AGGGTCCACC TGGTCGGCTG CACCTGTGGA GGAGGAGGTG
  51 GATTTCAGGC TTCCCGTAGA CTGGAAGAAT CGGCTCAAAA CCGCTTGCCT
 101 CGCAGGGGCT GAGCTGGAGG CAGCGAGGCC GCCCGACGCA GGCTTCCGGC
 151 GAGACATGGC AGGGCAAGGA TGGCAGCCCG GCGGCAGGGC CCGGCGAGGA
 201 GCGCGAACCC GCGGCCGCAG TTCCCAGGCG TCTGCGGGCG CGAGCACGCC
 251 GCGACCCTGC GTGCGCCGGG GCGGGGGGGC GGGGCCTCGC CTGCACAAAT
 301 AGGGACGAGG GGGCGGGGCG GCCACAATTT CGCGCCAAAC TTGACCGCGC
 351 GTTCTGCTGT AACGAGCGGG CTCGGAGGTC CTCCCGCTGC TGTCATGGTT
 401 GGTTCGCTAA ACTGCATCGT CGCTGTGTCC CAGAACATGG GCATCGGCAA
 451 GAACGGGGAC CTGCCCTGGC CACCGCTCAG GTATCTGCCG GGCCGGGGCG
 501 ATGGGACCCA AACGGGCGCA GGCTGCCCAC GGTCGGGGTA CCTGGGCGGG
 551 ACGCGCCAGG CCGACTCCCG GCGAGAGGAT GGGGCCAGAC TTGCGGTCTG
 601 CGCTGGCAGG AAGGGTGGGC CCGACTGGAT TCCCCTTTTC TGCTGCGCGG
 651 GAGGCCCAGT TGCTGATTTC TGCCCGGATT CTGCTGCCCG GTGAGGTCTT
 701 TGCCCTGCGG CGCCCTCGCC CAGGGCAAAG TCCCAGCCCT GGAGAAAACA
 751 CCTCACCCCT ACCCACAGCG CTCCGTTTGT CAGGTGCCTT AGAGCTCGAG
 801 CCCAAGGGAT AATGTTTCGA GTAACGCTGT TTCTCTAACT TGTAGGAATG
 851 AATTCAGATA TTTCCAGAGA ATGACCACAA CCTCTTCAGT AGAAGGTAAT
 901 GTGGGATTAA GTAGGGTCTT GCTTGATGAA GTTTACCAGT GCAAATGTTA
 951 GTTAAATGGA AAGTTTTCCG TGTTAATCTG GGACCTTTTC TCTTATTATG
1001 GATCTGTATG ATCTGTATGC AGTTCCCAAG GTTCATTTAC CATTATTAAA
1051 AAATTTTTGT CTTAGAAATT TTATGTATGT CAACGCACGA GCAAATTATC
1101 AGGCATGGGG CAGAATTGGC AACTGGGTGG AGGCTTCGGT GGAGGTTAGC
1151 ACTCCGAAAG GAAAACAGAG TAGGCCTTTG GAACAGCTGC TGGAAGAGAT
1201 AAGGCCTGAA CAAGGGCAGT GGAGAAGAGA GGGTAAAAAT TTTTTAAGGT
1251 TACATGACCC TGGATTTTGG AGATC
```

FIG 4B

```
   1 CTGCAGCGCC AGGGTCCACC TGGTCGGCTG CACCTGTGGA GGAGGAGGTG
  51 GATTTCAGGC TTCCCGTAGA CTGGAAGAAT CGGCTCAAAA CCGCTTGCCT
 101 CGCAGGGGCT GAGCTGGAGG CAGCGAGGCC GCCCGACGCA GGCTTCCGGC
 151 GAGACATGGC AGGGCAAGGA TGGCAGCCCG GCGGCAGGGC CGGCGAGGA
 201 GCGCGAACCC GCGGCCGCAG TTCCCAGGCG TCTGCGGGCG CGAGCACGCC
 251 GCGACCCTGC GTGCGCCGGG GCGGGGGGGC GGGGCCTCGC CTGCACAAAT
 301 AGGGACGAGG GGGCGGGCG GCCACAATTT CGCGCCAAAC TTGACCGCGC
 351 GTTCTGCTGT AACGAGCGGG CTCGGAGGTC CTCCCGCTGC TGTCATGGTT
 401 GGTTCGCTAA ACTGCATCGT CGCTGTGTCC CAGAACATGG GCATCGGCAA
 451 GAACGGGGAC CTGCCCTGGC CACCGCTCAG GTATCTGCCG GGCCGGGGCG
 501 ATGGGACCCA AACGGGCGCA GGCTGCCCAC GGTCGGGGT
 551          GG CCGACTCCCG GCGAGAGGAT GGGGCCAGAC TTGCGGTCTG
 601 CGCTGGCAGG AAGGGTGGGC CCGACTGGAT TCCCCTTTTC TGCTGCGCGG
 651 GAGGCCCAGT TGCTGATTTC TGCCCGGATT CTGCTGCCCG GTGAGGTCTT
 701 TGCCCTGCGG CGCCCTCGCC CAGGGCAAAG TCCCAGCCCT GGAGAAAACA
 751 CCTCACCCCT ACCCACAGCG CTCCGTTTGT CAGGTGCCTT AGAGCTCGAG
 801 CCCAAGGGAT AATGTTTCGA GTAACGCTGT TTCTCTAACT TGTAGGAATG
 851 AATTCAGATA TTTCCAGAGA ATGACCACAA CCTCTTCAGT AGAAGGTAAT
 901 GTGGGATTAA GTAGGGTCTT GCTTGATGAA GTTTACCAGT GCAAATGTTA
 951 GTTAAATGGA AAGTTTTCCG TGTTAATCTG GGACCTTTTC TCTTATTATG
1001 GATCTGTATG ATCTGTATGC AGTTCCCAAG GTTCATTTAC CATTATTAAA
1051 AAATTTTGT CTTAGAAATT TTATGTATGT CAACGCACGA GCAAATTATC
1101 AGGCATGGGG CAGAATTGGC AACTGGGTGG AGGCTTCGGT GGAGGTTAGC
1151 ACTCCGAAAG GAAAACAGAG TAGGCCTTTG AACAGCTGC TGGAAGAGAT
1201 AAGGCCTGAA CAAGGGCAGT GGAGAAGAGA GGGTAAAAAT TTTTAAGGT
1251 TACATGACCC TGGATTTTGG AGATC
```

METHODS FOR DETERMINING SUSCEPTIBILITY TO DEVELOPMENTAL DISORDERS DUE TO A COMBINATION OF GENETIC AND ENVIRONMENTAL FACTORS

CROSS-REFERENCE TO RELATED APPLICATIONS

The present application is a divisional of application U.S. Ser. No. 09/577,266 filed May 23, 2000, now issued U.S. Pat. No. 6,912,492, which is a non-provisional application claiming the priority of provisional U.S. Ser. No. 60/136,198 filed May 25, 1999, the disclosures of which are hereby incorporated by reference in their entirety. Applicants claim the benefits of these applications under 35 U.S.C. §119(e).

FIELD OF THE INVENTION

The invention relates generally to novel methods of diagnosing, preventing, and treating specific diseases which are caused by a combination of genetic and environmental factors. One such disease exemplified is schizophrenia.

BACKGROUND OF THE INVENTION

The term "schizophrenia" was introduced by Bleuler in the beginning of this century to encompass a dissociation or disruption of thought processes, along with a dichotomy among thought, emotion, and behavior [Bleuler, *Translation J. Zinkin*, New York: International University Press (1950)]. The current definition of schizophrenia includes a break with reality that is usually manifested as hallucinations, delusions, or disruption in thought processes [Carpenter et al., *Medical Progress*, 330:681-690 (1994)]. At present the nationally accepted definition for the diagnosis of schizophrenia is contained in Diagnostic and Statistical Manual for Mental Disorders, Fourth Edition, Washington, D.C. (1994): American Psychiatric Association, hereby incorporated by reference in its entirety.

Schizophrenia is a clinical syndrome that has a profound influence on public health. The symptoms for schizophrenia begin early in life, and continues for most patients throughout their lives. An estimate of the direct and indirect costs of schizophrenia was thirty-three billion dollars for 1990 in the United States alone [Carpenter et al., 1994, supra]. Indeed, one of every forty dollars spent for total heath care expenditures in the United States is spent on treating schizophrenia [Rupp et al., *Psychiatric Clin. North Am.*, 16:413-423 (1993)]. Furthermore, estimates have been made suggesting that up to 50% of the homeless American population is schizophrenic [Bachrach, In: *Treating the Homeless Mentally Ill*, Washington, D.C., American Psychiatric Press, 13-40, Lamb et al. ed. (1992)].

The genetic factors in schizophrenia, though clearly documented to be present, are not simple [Carpenter and Buchanan, *N. Engl. J. Med.*, 330:681-689 (1994); Gottesman, *Clin. Genet.*, 46:116-123 (1994)]. Schizophrenia is, at least in part, a neurodevelopmental disorder, a birth defect in which the brain has been subtly damaged during development [Carpenter and Buchanan, *N. Engl. J. Med.*, 330:681-689 (1994); Weinberger, *Arch. Gen. Psychiatry*, 44:660-669 (1987); Brixey et al., *J. Clin. Psychol*, 49:447-456 (1993)]. Evidence of this damage is seen both at autopsy [Kovelman and Scheibel, *Biol. Psychiatry*, 19:1601-1621 (1984); Bogerts et al., *Arch. Gen. Psychiatry*, 42:784-791 (1985); Jakob and Beckman, *J. Neural Transm.*, 65:303-326 (1986); Brown et al., *Arch. Gen. Psychiatry*, 43:36-42 (1986); Benes and Bird, *Arch Gen Psychiatry*, 44:608-616 (1987); Colter et al., *Arch Gen Psychiatry*, 44:1023 (1987); Altshuler et al., *Arch. Gen. Psychiatry*, 47:1029-1034 (1990); Pakkenberg, *Schizophr. Res.*, 7:95-100 (1992); Bogerts, *Schizophr. Bull.*, 19:431-445 (1993); Shapiro, *Schizophr. Res.*, 10:187-239 (1993)] and by neuroimaging [Jeste et al., *Br. J. Psychiatry*, 153:444-459 (1988); Suddath et al., *Am. J. Psychiatry*, 146:464-472 (1989); Suddath et al., *N. Engl. J. Med.*, 322:789-794 (1990); DeLisi et al., *Biol. Psychiatry*, 29:159-175 (1991); Breier et al., *Arch. Gen. Psychiatry*, 49:921-926 (1992); O'Callaghan et al., *J. R. Soc. Med.*, 85:227-231 (1992); Bogerts et al., *Biol. Psychiatry*, 33:236-246 (1993); Andreasen et al., *Science*, 266:294-298 (1994)]. The pattern of this brain damage and the presence of minor congenital abnormalities point to an insult occurring during the second trimester of fetal development [Bracha et al., *Biol. Psychiatry*, 30:719-725 (1991); Bracha et al., *Am. J. Psychiatry*, 149:1355-1361 (1992); Green et al., *Psychiatry Res.*, 53:119-127 (1994)]. Epidemiological studies have documented a season-of-birth effect by which schizophrenics are more frequently born during winter and early spring than during other seasons [Boyd et al., *Schizophr. Bull.*, 12:173-186 (1986); Kendell and Adams, *Br. J. Psychiatry*, 158:758-763 (1991); O'Callaghan et al., *Br. J. Psychiatry*, 158:764-769 (1991)]. Also, individuals exposed to an influenza epidemic [Mednick et al., *Arch. Gen. Psychiatry*, 45:189-192 (1988); Barr et al., *Arch. Gen. Psychiatry*, 47:869-874 (1990); O'Callaghan et al., *Lancet.*, 337:1248-1250 (1991); Murray et al., *J. Psychiatr. Res.*, 26:225-235 (1992); Adams et al., *Br. J. Psychiatry*, 163:522-534 (1993)] or famine [Susser and Lin, *Arch. Gen. Psychiatry*, 49:983-988 (1992)] during their second trimester of fetal development have increased risk of later developing schizophrenia, according to some studies but not others [Kendell, *Arch. Gen. Psychiatry*, 46:878-882 (1989); Crow and Done, *Br. J. Psychiatry*, 161:390-393 (1992)]. This has suggested that an environmental effect such as dietary deficiency, virus infection [Kirch, *Schizophr. Bull.*, 19:355-370 (1993)], vitamin deficiency, or effect of cold weather may be acting during fetal development.

Linkage mapping studies in schizophrenia have been difficult. Recently, some studies [Straub et al., *Nature Genet.*, 11:287-293 (1995); Schwab et al., *Nature Genet.*, 11:325-327 (1995); Moises et al., *Nature Genet.*, 11:321-324 (1995)] have supported a gene locus on chromosome 6 (6p24-22, near the HLA region) as having an effect in schizophrenia; other studies gave little or no support to a marker in this region [Wang et al., *Nature Genet.*, 10:41-46 (1995); Mowry et al., *Nature Genet.*, 11:233-234 (1995); Gurling et al., *Nature Genet.*, 11:234-235 (1995); Antonarakis et al., *Nature Genet.*, 11:235-236 (1995)]. At best this locus appeared to be involved in only about 15-30% of families [Straub et al., 1995, supra]. Also, some evidence for loci on chromosomes 3 [Pulver et al., *Am. J. Med. Genet.*, 60:252-260 (1995), 8 [Pulver et al., *Am. J. Med. Genet.*, 60:252-260 (1995); Kendler et al., *Am. J. Psych.* 153:1534-1540 (1996), 9 [Coon et al., *Biol. Psychiatry*, 34:277-289 (1993); Moises et al., *Nature Genet.*, 11:321-324 (1995)] and 22 [Coon et al., *Am. J. Med. Genet.*, 54:72-79 (1994); Pulver et al., *Am. J. Med. Genet.*, 54:3-43 (1994)] have been reported. In addition, two polymorphic markers very close to the gene encoding dihydrofolate reductase (DHFR) on chromosome 5q, D5S76 and D5S39, gave very high lod scores (as high as 6.49, i.e. odds of about 3 million to one in favor of genetic linkage versus chance occurrence) in 7 British and Icelandic schizophrenia families studied [Schwab et al., *Nat. Genet.* 11:325-327

(1997); Straub et al., Molec Psychiatr. 2:148-155 (1997)]. However, this result could not be confirmed in studies of numerous other families.

There could be several reasons for this difficulty. First, there may be more than one gene involved, (locus heterogeneity). Second, the genetic factor(s) may be common in the population (high disease allele frequency), thus diminishing the power of linkage studies [Terwilliger and Ott, *Handbook of Human Genetic Linkage*, Baltimore: Johns Hopkins Univ. Pr., 181 (1994)]. Third, the correct genetic model may be unknown [Owen, *Psychol. Med.*, 22:289-293 (1992)]. Any or all of these factors could diminish the power of a linkage study sufficiently to make success very difficult [Terwilliger and Ott, 1994, supra].

Thus the current (developmental) model for schizophrenia is that genetic and environmental factors cause brain damage in a fetus that later develops schizophrenia. However, the genetic and environmental factors have not been identified. Also, extensive linkage and association studies have failed to identify genes determining schizophrenia.

Indeed, schizophrenia appears to be just one of a family of developmental disorders whose cause has not been identified. Other such developmental disorders are defined by the Diagnostic and Statistical Manual for Mental Disorders, Fourth Edition, Washington, D.C (1994) and include: Tourette Syndrome which is identical to Tourette's Disorder and is a sub-category of Tic Disorders; Bipolar Disorder which is identical with Bipolar I Disorder or Bipolar II disorder; Autism which is identical with Autistic Disorder which is a subcategory of Pervasive Developmental Disorders; Conduct disorder which is a subcategory of Attention-Deficit and Disruptive Behavioral Disorders; Attention-Deficit Hyperactivity Disorder which is identical to Attention-Deficit/Hyperactivity Disorder and to Attention-Deficit/Hyperactivity Disorder NOS (not otherwise specified) which is also a subcategory of Attention-Deficit and Disruptive Behavioral Disorders; Obsessive-Compulsive Disorder which is a subtype of Anxiety Disorders; Chronic Multiple Tics Syndrome which is identical to Chronic Motor or Vocal Tic Disorder which is a subtype of Tic Disorders; and Learning Disorders.

In addition Spina bifida is a developmental disorder. Spina bifida is a form of neural tube defect in which neural elements (spinal nerves or spinal chord) or coverings of the brain and spinal chord (dura mater, arachnoid mater) herniate through a midline defect into a cystic cavity covered completely or partially by skin.

Therefore, there is a need for new methods of diagnosing individuals susceptible to developing a developmental disorder. In addition, there is a need for methods of identifying individuals susceptible to having offspring that develop a developmental disorder. Finally, there is a need for a method of treating such susceptible individuals in order to prevent and/or ameliorate the symptoms due to and/or associated with the developmental disorder.

The citations of any reference herein should not be construed as an admission that such reference is available as "Prior Art" to the instant application.

SUMMARY OF THE INVENTION

The present invention provides methods of diagnosing, preventing and/or treating specific developmental disorders. Towards this end the present invention provides methods of identifying an individual as being genetically or environmentally susceptible for developing or having a developmental disorder or for having offspring that develop the developmental disorder. Such a developmental disorder can be schizophrenia, spina bifida cystica, Tourette's syndrome, bipolar illness, autism, conduct disorders, attention deficit disorder, obsessive compulsive disorder, chronic multiple tic syndrome and learning disorders such as dyslexia. In addition, any of the methods provided herein for identifying an individual as being genetically and/or environmentally susceptible for having or developing a developmental disorder or for having offspring that develop the developmental disorder can also be used in diagnosing the individual, preferably in conjunction with a clinical diagnosis.

Therefore, the present invention provides methods of identifying an individual as being genetically susceptible for having or developing a developmental disorder.

The present invention further provides methods of identifying an individual as being genetically susceptible for having offspring that are susceptible for developing a developmental disorder. Methods of identifying an individual as being susceptible due to environmental factors for having or developing a developmental disorder are also provided. In addition, the present invention provides methods of identifying an individual as being susceptible of having offspring that are susceptible for developing a developmental disorder. The present invention also provides methods of identifying an individual as being susceptible for having or developing a developmental disorder due to both environmental and genetic factors. The present invention further provides methods of identifying an individual as being susceptible for having offspring that are susceptible for developing a developmental disorder The present invention therefore provides methods for compiling genetic reference datasets, environmental reference datasets and/or genetic and environmental reference datasets for use in determining a predicted probability for an individual of having a susceptibility for having or developing a developmental disorder, or for having offspring that develop a developmental disorder.

In one aspect of the invention, the present invention provides methods that comprise generating a genetic reference dataset for use in determining the predicted probability of an individual for having a susceptibility for having or developing a developmental disorder due to genetic factors, or for having offspring that develop a developmental disorder due to genetic factors.

One such embodiment comprises collecting a biological sample from a human subject. The human subject can be a diagnostic proband, a blood relative of the diagnostic proband, an affected proband, a blood relative of the affected proband, a control proband, and/or a blood relative of the control proband. The biological sample contains nucleic acids and/or proteins from the human subject. The nucleic acids and/or proteins from the biological sample are then analyzed resulting in a partial or full genotype for the alleles of the genes involved in folate, pyridoxine, and/or cobalamin metabolism. The partial or full genotype then forms a dataset of genetic explanatory variables for the human subject. The dataset of genetic explanatory variables is then compiled from multiple human subjects into a genetic reference dataset. Such compilations are exemplified in the Detailed Description and Examples below.

In another aspect, the present invention provides a method that comprises generating a genetic and environmental reference dataset for use in determining the predicted probability of an individual for having a susceptibility for having or developing a developmental disorder due to genetic factors and environmental factors, or for having offspring that develop a developmental disorder due to genetic factors and environmental factors. One such embodiment comprises obtaining dietary and epidemiological information for environmental explanatory variables for the human subjects and combining the environmental explanatory variables with a genetic reference dataset for the human subjects as described above.

In another aspect, the present invention provides an environmental reference dataset for use in the determination of the predicted probability for an individual for having a susceptibility for having or developing a developmental disorder due to environmental factors, or for having offspring that develop a developmental disorder due to environmental factors One such embodiment comprises obtaining dietary and epidemiological information for environmental explanatory variables for a human subject. The human subject can be a diagnostic proband, a blood relative of the diagnostic proband, an affected proband, a blood relative of the affected proband, a control proband, or a blood relative of the control proband. The dataset of environmental explanatory variables is then compiled from multiple human subjects into an environmental reference dataset for the human subjects.

The developmental disorder forming the basis of the reference datasets of the present invention can be schizophrenia, or spina bifida cystica, or Tourette's syndrome, or dyslexia, or conduct disorder, or attention-deficit hyperactivity disorder, or bipolar illness, or autism, or chronic multiple tic syndrome or obsessive-compulsive disorder, or like disorders. A blood relative is preferably the mother of the individual, a sibling, the father or a grandparent of the individual. When the reference dataset is for use in the determination of the predicted probability for an individual of having a susceptibility for having offspring that develop a developmental disorder, the individual is preferably a pregnant woman. The reference datasets of the present invention are themselves part of the present invention.

The present invention further provides methods of estimating the genetic susceptibility of an individual to have or to develop a developmental disorder, or to have offspring that develop a developmental disorder. In one such embodiment the method comprises collecting a biological sample from a participant (or participants) who is either the individual or a blood relative of the individual. The biological sample contains nucleic acids and/or proteins of the participant. The analysis of the nucleic acids and/or proteins from the biological sample yield a partial or full genotype for the alleles of the genes involved in folate, pyridoxine, and/or cobalamin metabolism. The partial or full genotype forms a dataset of genetic explanatory variables for the participants. The dataset of genetic explanatory variables obtained are added to a genetic reference dataset forming a combined genetic dataset. A model is then formulated comprising the genetic explanatory variables obtained from the participants and the combined genetic dataset is analyzed. A predicted probability for the individual for having and/or developing a developmental disorder and/or having offspring that develop a developmental disorder is then determined. The genetic susceptibility of an individual to have or to develop a developmental disorder and/or have offspring that develop a developmental disorder is estimated. In a preferred embodiment, analyzing the combined genetic dataset is performed by binary linear regression. In a more preferred embodiment, the binary linear regression is performed with the SAS system. In another preferred embodiment, the model is modified by adding or subtracting one or more genetic explanatory variables and the combined genetic dataset is re-analyzed, preferably by binary logistic regression. In this case a model is chosen that best fits the data. This can be accomplished by testing the model for goodness of fit.

The present invention also provides methods of estimating the genetic and environmental susceptibility of an individual to have or to develop a developmental disorder and/or for having offspring that develop a developmental disorder. One such embodiment comprises collecting a biological sample from one or more participants. Again, the participant is either the individual or a blood relative of the individual. The biological sample contains nucleic acids and/or proteins of the participant. The nucleic acids and/or proteins from the biological sample are analyzed resulting in a partial or full genotype for the alleles of the genes involved in folate, pyridoxine, and/or cobalamin metabolism. The partial or full genotype forms a dataset of genetic explanatory variables for the participant. Dietary and epidemiological information for environmental explanatory variables for the participant(s) are also obtained which are used to form a dataset of environmental explanatory variables for the participant(s). The datasets of genetic explanatory variables and the dataset of environmental explanatory variables are added to a genetic and environmental reference dataset forming a combined genetic and environmental dataset. A model is formulated comprising the genetic and environmental explanatory variables obtained from the participant(s). The combined genetic and environmental dataset is then analyzed and a predicted probability for the individual for having and/or developing a developmental disorder and/or for having offspring that develop a developmental disorder is determined. The genetic and environmental susceptibility of an individual to have or to develop a developmental disorder and/or have offspring that develop a developmental disorder is estimated. In a preferred embodiment, analyzing the combined genetic and environmental dataset is performed by binary linear regression. In a more preferred embodiment the binary linear regression is performed with the SAS system. In another preferred embodiment the model is modified by adding or subtracting one or more genetic and/or environmental explanatory variables and the combined genetic and environmental dataset is re-analyzed preferably, by binary logistic regression. In this case a model is chosen that best fits the data. This can be accomplished by testing the model for goodness of fit.

For any of these methods, the developmental disorder can be schizophrenia, spina bifida cystica, Tourette's syndrome, bipolar illness, autism, conduct disorder, attention deficit hyperactivity disorder, obsessive compulsive disorder, chronic multiple tic syndrome and learning disorders such as dyslexia.

In a particular embodiment, the individual is suspected of being genetically susceptible of having or for developing the developmental disorder and/or of being genetically susceptible of having offspring that develop the developmental disorder. In a preferred embodiment of this type, the individual is suspected of being genetically susceptible for having or for developing the developmental disorder and/or of being genetically susceptible of having offspring that develop the developmental disorder because a blood relative has the developmental disorder. In one such embodiment the blood relative is a parent, a sibling, or a grandparent. In a preferred embodiment the blood relative is the mother of the individual. In a particular embodiment in which the individual is suspected of being genetically susceptible of having offspring that develop the developmental disorder, the individual is a pregnant woman. In another such embodiment the individual is the mate of the pregnant woman. In a particular embodiment exemplified below, the developmental disorder is schizophrenia.

Since the availability of the data regarding the genetic and environmental explanatory factors can vary in separate determinations, variations in the explanatory factors used is clearly envisioned by the present invention.

The present invention further provides methods of lowering the risk of a pregnant woman to have a child that will develop a developmental disorder. One such embodiment comprises administering methylfolate, cobalamin or pyridoxine to the pregnant woman and/or fetus, which lowers the risk of the pregnant woman to give birth to a child with a developmental disorder. In a particular embodiment of this type, the pregnant woman had been previously determined to be susceptible of having offspring that develop a developmental disorder by a method disclosed herein. The present invention further provides a method of determining if any treatment is advisable for a pregnant woman that is genetically susceptible to having offspring that develop a developmental disorder which comprises determining the concentration of a risk factor from a tissue sample or body fluid from the pregnant woman. When the concentration of the risk factor is statistically above or below an accepted normal range, treatment is advisable.

The present invention further provides methods of determining if any treatment is advisable for a pregnant woman who has been determined to be susceptible to having offspring that develop a developmental disorder. One such embodiment comprises determining the concentration of a risk factor from a tissue sample or body fluid from the pregnant woman. When the concentration of the risk factor is statistically above or below an accepted normal range, treatment is advisable. In a particular embodiment of this type, the pregnant woman had been previously determined to be susceptible of having offspring that develop a developmental disorder by a method disclosed herein.

Methods of monitoring the effect of the administration of methylfolate, cobalamin or pyridoxine to the pregnant woman who has been determined to be susceptible to having offspring that develop a developmental disorder are also included in the present invention. One such embodiment comprises determining the concentration of a risk factor from a tissue sample or body fluid from the pregnant woman. When the concentration of the risk factor is statistically within an accepted normal range, the treatment is deemed effective. In a particular embodiment of this type, the pregnant woman had been previously determined to be susceptible of having offspring that develop a developmental disorder by a method disclosed herein. The risk factor can be any substance and/or metabolite linked to folate and/or cobalamin and/or pyridoxine metabolism. In one embodiment, the risk factor is homocysteine. In yet another embodiment, the risk factor is folate. In still another embodiment, the risk factor is cobalamin.

The present invention also provides a method of treating an asymptomatic individual determined to be susceptible for developing a developmental disorder comprising administering methylfolate, cobalamin and/or pyridoxine. In a particular embodiment of this type, the asymptomatic individual had been previously determined to be susceptible of developing a developmental disorder by a method disclosed herein.

The DNA samples from the persons tested may be obtained from any source including blood, a tissue sample, amniotic fluid, a chorionic villus sampling, cerebrospinal fluid, and urine.

The present invention includes but is not limited to the examples of proteins encoded by genes involved in folate, cobalamin and pyridoxine metabolism compiled in Tables 2-7 in the Detailed Description of the Invention, below. For certain genes nucleic acid and/or amino acid sequence data is also provided. These genes and related sequence data are solely intended as examples of genes that are suitable to be used in the methods described herein. Such sequence data can be used for carrying out the genetic analysis of the present invention. However, the present invention is not intended to be limited in any way to such lists of proteins or the related sequence data.

It is further contemplated by the present invention to provide methods that include the testing for a genetic mutations in individual genes involved in folate and cobalamin metabolism and/or in individual combinations of such genes (e.g., methylenetetrahydrofolate reductase gene and methionine synthase). In addition, all possible combinatorials, and permutations of such genes including a constellation comprising all of the genes involved in folate, pyridoxine, and cobalamin metabolism is envisioned by the present invention. Alternatively, a constellation of genes in which any one or more genes can be excluded from those tested is also contemplated by the present invention (for example, a given constellation of genes can include genes encoding all of the proteins in Table 2 and 4 except the folate receptor 2-like protein). Thus all of such possible constellations are envisioned by, and are therefore part of the present invention.

The present invention also provides DNA polymorphisms that can be used as genetic explanatory factors in the present invention. One such embodiment is a nucleic acid encoding a genetic variant of human dihydrofolate reductase comprising a nucleotide sequence having a 19 base-pair deletion spanning nucleotides 540 to 558 of the nucleotide sequence of SEQ ID NO:41. In a preferred embodiment the nucleic acid has the nucleotide sequence of SEQ ID NO:42.

The present invention also includes primers. One such embodiment is a PCR primer that can be used to distinguish SEQ ID NO:42 from SEQ ID NO:41. Another embodiment is a PCR primer that can be used to distinguish SEQ ID NO:42 from SEQ ID NO:45. These primers are useful for identifying the 19 base-pair deletion spanning nucleotides 540 to 558 of the nucleotide sequence of SEQ ID NO:41 (see Example 2). In a particular embodiment, the PCR primer comprises 8 to 100 and preferably 10 to 50 consecutive nucleotides from the nucleotide sequence of SEQ ID NO:41. In another embodiment the PCR primer comprises 8 to 100 and preferably 10 to 50 consecutive nucleotides from the nucleotide sequence of the complementary strand of SEQ ID NO:41. In still another embodiment the PCR primer comprises 8 to 100 and preferably 10 to 50 consecutive nucleotides from the nucleotide sequence of SEQ ID NO:42. In yet another embodiment the PCR primer comprises 8 to 100 and preferably 10 to 50 consecutive nucleotides from the nucleotide sequence of the complementary strand of SEQ ID NO:42. In still another embodiment the PCR primer comprises 8 to 100 and preferably 10 to 50 consecutive nucleotides from the nucleotide sequence of SEQ ID NO:45. In yet another embodiment the PCR primer comprises 8 to 100 and preferably 10 to 50 consecutive nucleotides from the nucleotide sequence of the complementary strand of SEQ ID NO:45.

In a particular embodiment the PCR primer comprises 8 to 100 and preferably 10 to 50 consecutive nucleotides from nucleotides 350 to 530 of SEQ ID NO:41. In a preferred embodiment of this type, the PCR primer has the nucleotide sequence of CTAAACTGCATCGTCGCTGTG (SEQ ID NO:38). In another particular embodiment the PCR primer comprises 8 to 100 and preferably 10 to 50 consecutive nucleotides from the complementary strand of nucleotides 550 to 850 of SEQ ID NO:41. In preferred embodiment of this type, the PCR primer comprises 8 to 100 and preferably 10 to 50 consecutive nucleotides from the complementary strand of nucleotides 570 to 690 of SEQ ID NO:41. In a particular embodiment, the PCR primer has the nucleotide sequence of AAAAGGGGAATCCAGTCGG (SEQ ID NO:39).

The present invention also provides a nucleic acid that hybridizes under standard hybridization conditions to the nucleotide sequence ACCTGGGCGGGACGCGCCA (SEQ ID NO:40). In another embodiment the nucleic acid hybridizes under standard hybridization conditions to the nucleotide sequence complementary to SEQ ID NO:40. In yet another embodiment the nucleic acid hybridizes under standard hybridization conditions to the nucleotide sequence ACCTGGGCGGGACGCGCC (SEQ ID NO:46). In yet another embodiment the nucleic acid hybridizes under standard hybridization conditions to the nucleotide sequence complementary to SEQ ID NO:46. In a particular embodiment the nucleic acid consists of 9 to 96 nucleotides. In another embodiment the nucleic acid consists of 12 to 48 nucleotides. In still another embodiment the nucleic acid consists of 15 to 36 nucleotides. In a preferred embodiment the nucleic acid consists of 17 to 20 nucleotides.

The present invention also provides a nucleic acid that hybridizes to the nucleotide sequence of SEQ ID NO:41, but not to the nucleotide sequence of SEQ ID NO:42 when the hybridization is performed under identical conditions. In a particular embodiment the nucleic acid comprises the nucleotide sequence of CCCACGGTCGGGGTACCTGGGCGG-GACGCGCCAGGCCGACTCCCGGCGA (SEQ ID NO:29). The present invention further provides a nucleic acid that hybridizes to the nucleotide sequence of SEQ ID NO:42, but not to the nucleotide sequence of SEQ ID NO:41 when the hybridization is performed under identical conditions. In a particular embodiment the nucleic acid comprises the nucleotide sequence of CCCACGGTCGGGGTGGCCGACTC-CCGGCGA (SEQ ID NO:37).

In a related embodiment the present invention provides an isolated nucleic acid that hybridizes to the complementary strand of the nucleotide sequence of SEQ ID NO:42, but not to the complementary strand of the nucleotide sequence of SEQ ID NO:41 when the hybridization is performed under identical conditions. In still another embodiment the nucleic acid hybridizes to the nucleotide sequence of SEQ ID NO:41, but not to the nucleotide sequence of SEQ ID NO:42 when the hybridization is performed under identical conditions. In still another embodiment the nucleic acid hybridizes to the complementary strand of the nucleotide sequence of SEQ ID NO:41, but not to the complementary strand of the nucleotide sequence of SEQ ID NO:42 when the hybridization is performed under identical conditions.

The present invention also provides a nucleic acid that hybridizes to the nucleotide sequence of SEQ ID NO:42, but not to the nucleotide sequence of SEQ ID NO:45 when the hybridization is performed under identical conditions. In a related embodiment the present invention provides an isolated nucleic acid that hybridizes to the complementary strand of the nucleotide sequence of SEQ ID NO:42, but not to the complementary strand of the nucleotide sequence of SEQ ID NO:45, when the hybridization is performed under identical conditions. In still another embodiment the nucleic acid hybridizes to the nucleotide sequence of SEQ ID NO:45, but not to the nucleotide sequence of SEQ ID NO:42 when the hybridization is performed under identical conditions. In still another embodiment the nucleic acid hybridizes to the complementary strand of the nucleotide sequence of SEQ ID NO:45, but not to the complementary strand of the nucleotide sequence of SEQ ID NO:42 when the hybridization is performed under identical conditions.

The present invention also provides for the use of the nucleic acids of the present invention (as well as other nucleic acids which can be used to identify DNA polymorphisms in the alleles of the genes involved in folate, pyridoxine, and/or cobalamin metabolism) in the methods of the present invention for identifying, diagnosing, preventing and/or treating individuals.

In methods of estimating the susceptibility due to genetic or genetic and environmental factors for an individual to have or to develop a developmental disorder or to have offspring that develop a developmental disorder, and for the corresponding methods of generating genetic, or genetic and environmental reference datasets, the present invention provides a step of analyzing nucleic acids and/or proteins from biological samples. In one particular embodiment, the assaying for the presence of the genetic variant of human dihydrofolate reductase having a nucleotide sequence with a 19 base-pair deletion spanning nucleotides 540 to 558 of the nucleotide sequence of SEQ ID NO:41 is included as part of this analysis. This genetic variant of human dihydrofolate reductase becomes a genetic explanatory variable.

Determining if the biological sample contains the genetic variant of human dihydrofolate reductase having a nucleotide sequence with a 19 base-pair deletion spanning nucleotides 540 to 558 of the nucleotide sequence of SEQ ID NO:41 can be performed by any appropriate method including PCR, special PCR, RT PCR, RFLP analysis, SSCP, and FISH.

In addition, all of the nucleic acids of the present invention including cDNA or genomic DNA can be placed into expression vectors operably associated with an expression control sequence. Alternatively, when the nucleic acid is part of an expression control sequence, the nucleic acid and/or the expression control sequence can be placed into an expression vector to control the expression of a coding sequence, such as a reporter gene. Such expression vectors can then be placed into either eukaryotic or prokaryotic host cells and expressed. The host cells comprising the expression vectors are also part of the present invention. In addition, when the nucleic acid includes a coding sequence or a part of a coding sequence, the present invention includes methods of purifying the gene products from the coding sequence or part thereof, and the purified gene products themselves.

Accordingly, it is a principal object of the present invention to provide a method for identifying an individual that is genetically inclined to develop a developmental disorder or disease.

It is a further object of the present invention to provide a method for identifying an individual that is genetically inclined to develop schizophrenia.

It is a further object of the present invention to provide a method for identifying an individual that is genetically inclined to have offspring having a developmental disorder.

It is a further object of the present invention to provide a method of diagnosing schizophrenia.

It is a further object of the present invention to provide a method of treating developmental disorders such as schizophrenia.

It is a further object of the present invention to provide a method for monitoring the treatment of the developmental disorder.

It is a further object of the present invention to provide a method for ameliorating the effect of a defect in folate, pyridoxine or cobalamin metabolism on a fetus due to the genetic or environmental status of a pregnant woman.

It is a further object of the present invention to provide a method of treating a patient who is genetically inclined to develop a developmental disorder such as schizophrenia.

It is a further object of the present invention to provide a method of overcoming a nutritional lack of folate, cobalamin or pyridoxine of a pregnant woman to prevent the development of the corresponding fetus developing a developmental disorder.

Other objects and advantages will become apparent to those skilled in the art from a review of the ensuing description.

These and other aspects of the present invention will be better appreciated by reference to the following drawings and Detailed Description.

BRIEF DESCRIPTION OF THE DRAWINGS

FIG. 1 shows primers for PCR amplification of the dihydrofolate reductase (DHFR) deletion polymorphism region.

FIG. 3 shows the sequences of PCR amplification products in the Region of the DHFR polymorphism region. * is explained in Text, see Example 2. Allele 1 corresponds to SEQ ID NO: 43 and Allele 2 corresponds to SEQ ID NO: 44.

FIG. 4A is a nucleotide sequence of the wild type human DHFR, (SEQ ID NO:41) from Yang et al., *J. Mol. Biol.* 176:169-187 (1984), GeneBank accession no: X00855. The start codon is in bold. FIG. 4B is the same nucleotide sequence as that of FIG. 4A except the deletion of the 19 nucleotides due to the DHFR deletion polymorphism, (SEQ ID NO:42).

DETAILED DESCRIPTION OF THE INVENTION

Figure 2:
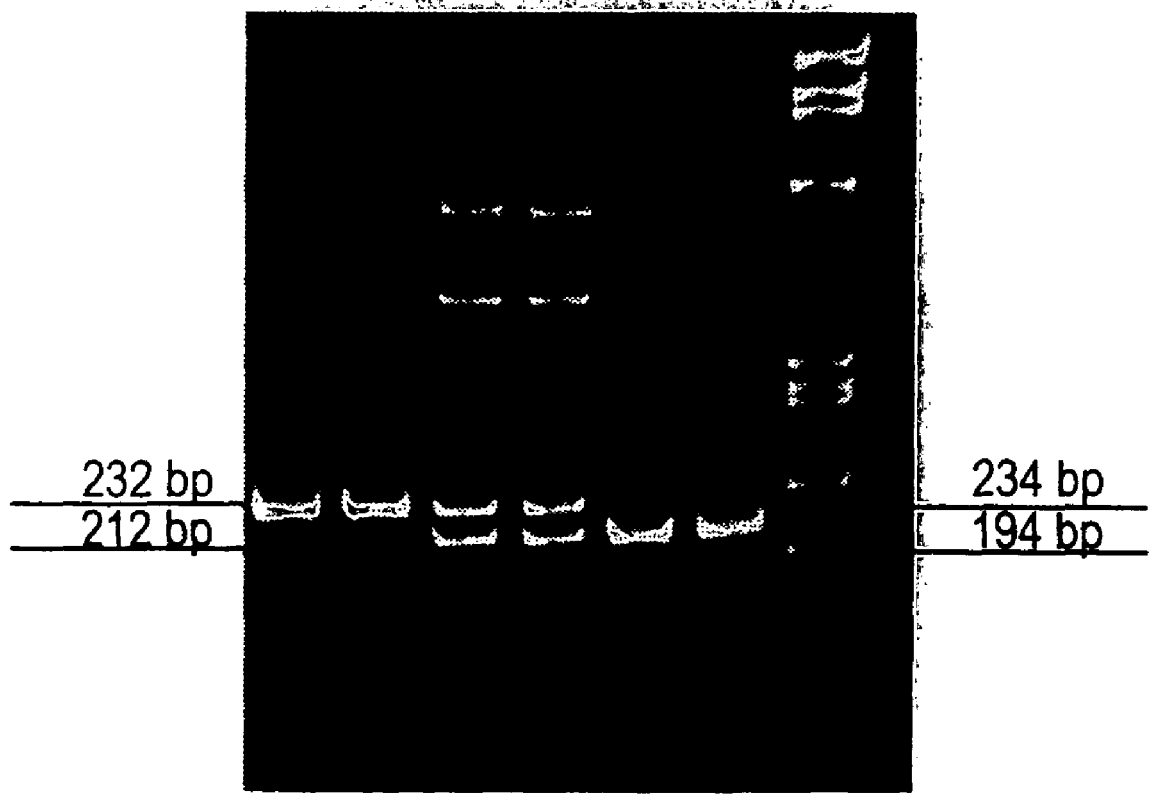
FIG. 2 shows the genotypes of the DHFR 19 basepair deletion by non-denaturing polyacrylamide gel electrophoresis. Lanes 1 and 2 show genotypes 1,1. Lanes 3 and 4 show genotypes 1, 2. Lanes 5 and 6 show genotypes 2,2. Lane 7 shows phiX174 RF DNA/HaeIII size markers from BRL Life Technologies.

The present invention in its broadest embodiment provides a method of diagnosing, preventing and/or treating specific physiological/developmental disorders. Such physiological/developmental disorders include schizophrenia, spina bifida cystica, Tourette's syndrome, bipolar illness, autism, conduct disorders, attention deficit disorder, obsessive compulsive disorder, chronic multiple tic syndrome and learning disorders such as dyslexia.

A particular aspect of the present invention provides methodology for diagnosing, preventing and/or treating a developmental disorder such as schizophrenia. Such methodology is premised on the correlation between abnormalities in folate, cobalamin, and/or pyridoxine metabolism in an individual and/or the mother of an individual and the occurrence of the developmental disorder, e.g., schizophrenia in the individual. Further, the present invention provides a framework (i.e., the gene-teratogen model, and the DNA Polymorphism-Diet-Cofactor-Development both of which are described in detail below) which fully explain the rationale for the correlation, though the ultimate usefulness of the methods of the present invention are independent of any particular model.

Within this context, the DNA Polymorphism-Diet-Cofactor-Development model maintains that a developmental disorder such as schizophrenia results in part from developmental brain damage sustained in utero due to maternal dietary deficiency of folate, pyridoxine or cobalamin potentiated by the aggregate effect of minor defects of folate, pyridoxine or cobalamin genes. The maternal damage to the fetus can result in part from insufficiency of the folate, pyridoxine and cobalamin themselves and/or from resulting effects such as immune deficiency and maternal teratogens, e.g. hyperhomocysteinemia. Genes from either parent acting in the fetus may modify these damaging effects as exemplified in the gene-teratogen model, below.

As described herein the present invention can be practiced on a case by case basis, or alternatively, it can be used in the screening of the general population, or within any particular subgroup, such as newborns (as is presently performed in the diagnosis and treatment of hyperphenylalaninemia).

Therefore, if appearing herein, the following terms shall have the definitions set out below.

As used herein a "gene involved in folate, pyridoxine, or cobalamin metabolism" is a gene that encodes a peptide or protein that plays a role in a pathway involved in either folate, pyridoxine, or cobalamin metabolism. An incomplete listing of examples of such proteins is given in Tables 2-7.

As used herein the term "individual" includes a fetus, infant, child, adolescent, and adult. Therefore, as used herein, an individual originates at conception.

As used herein an individual with a susceptibility for "having offspring that develop a developmental disorder" is meant to be indicative of the susceptibility of the offspring of that individual to develop the developmental disorder and is not in any way meant to be indicative of the susceptibility of the individual to have offspring.

The term "proband" as used herein is operationally defined by Table 8 along with the accompanying explanatory information (see, Example 1). For most purposes, the proband can be considered the central figure in the familial analysis, the remaining individuals in the family being designated as "blood relatives". There are three types of probands: (1) an "affected proband" i.e., an individual that is believed to have a developmental disorder; (2) a "control proband" an individual that is believed not to have a developmental disorder; and (3) a "diagnostic proband" i.e., an individual being diagnosed.

As used herein a "blood relative" of an individual is a relative that is related to the individual in a genetic sense. Blood relatives can include mothers, fathers, children, uncles, aunts, brothers, sisters, and grandparents. Preferably a blood relative is a parent, a sibling, or a grandparent. Adopted relatives, step-parents, relatives through marriage and the like are not blood relatives. Therefore, as used herein, the terms "mother", "father", "sibling", "grandparent", "grandfather" and "grandmother" are indicative of blood relationships.

As used herein a "mate of an individual" is a person whose genetic material is combined with that of the individual for the conception of the offspring in question.

As used herein the term "schizophrenia" describes a disorder that is at least partially due to one or more genetic mutations or polymorphisms in one or more genes involved in folate, cobalamin or pyridoxine metabolism in an individual that is schizophrenic and/or to one or more genetic mutations or polymorphisms in one or more genes involved in folate, cobalamin or pyridoxine metabolism in the mother of that individual.

As used herein an individual is "schizophrenic" when the individual displays symptoms that would be accepted by an experienced psychiatrist to merit a diagnosis of schizophrenia. Such a diagnosis is based, at least in part, on the currently evolving guidelines for the diagnosis of schizophrenia which are listed in the successive editions of Diagnostic and Statistical Manual for Mental Disorders, put out by the American Psychiatric Association. The current edition is the DSM, Fourth Edition (1994).

As used herein the terms "spina bifida cystica", "Tourette's syndrome", "bipolar illness", "autism", "conduct disorder", "attention deficit disorder", "obsessive compulsive disorder", "chronic multiple tic syndrome" and "learning disorders" such as "dyslexia"describe disorders which display symptoms that would be accepted by an experienced psychiatrist to merit a diagnosis of that disorder. Such a diagnosis is based, at least in part, on the currently evolving guidelines which are listed in the successive editions of Diagnostic and Statistical Manual for Mental Disorders, put out by the American Psychiatric Association. The current edition is the DSM, Fourth Edition (1994).

As used herein the term "teratogenic locus" indicates one or more alleles that act in a pregnant woman to cause an intrauterine teratogenic effect on the fetus.

As used herein the terms "specificity locus" or "modifying locus" are used interchangeably and are indicative of one or more alleles that can act during pregnancy and/or after birth to prevent, modify, and/or ameliorate the teratogenic effect of the teratogenic locus.

As used herein a "constellation of genetic mutations" is the set of genetic risk factor mutations that is present in a proband and relatives of the proband. One example of a constellation of genetic mutations is shown in a line of Table 8, below.

As used herein a "risk factor" is a teratogen or substance (including a defective gene) that can lead to a teratogenic effect that is present or suspected of being present in a tissue sample or body fluid of an individual's mother during the individual's gestation and/or present or suspected of being present in a tissue sample or body fluid of the individual.

As used herein a "genetic risk factor" is used interchangeably with the term "genetic explanatory variable" and is a genetic mutation and/or polymorphism that causes or potentially can cause the formation of and/or lead to the development of a risk factor in an individual or the individual's mother during gestation.

As used herein an "environmental risk factor" is used interchangeably with the term "environmental explanatory variable" and is an environmental factor that causes or potentially can cause the formation of and/or lead to the development of a risk factor in an individual or the individual's mother during gestation.

As used herein an "explanatory variable" is either an "environmental explanatory variable" or a "genetic explanatory variable" or the variable defined by their interaction or any combination of the above.

Enzymes whose deficiency may raise plasma homocysteine include methylenetetrahydrofolate reductase (MTHFR), methionine synthase, and folate receptors/transport proteins/binding proteins (as well as all of the proteins listed in Tables 2-7 below).

The current (developmental) model for schizophrenia is that genetic and environmental factors cause brain damage in a fetus that later develops schizophrenia. However, the genetic and environmental factors have not been identified. Also, extensive linkage and association studies have failed to identify genes determining schizophrenia. The reasons usually given for this difficulty include: (i) locus heterogeneity, i.e., more than one gene locus is involved, perhaps many gene loci each with a small effect; (ii) the mode of inheritance of schizophrenia is unknown; and (iii) an additional possible factor is that the frequency of the disease alleles may be high, thus greatly reducing the power of linkage studies.

The DNA Polymorphism-Diet-Cofactor-Development model explains all of these difficulties and at the same time proposes a unified metabolic abnormality. The unified metabolic abnormality is: (a) ENVIRONMENTAL, i.e., due to a folate/cobalamin/pyridoxine deficiency caused by either decreased ingestion or increased requirement during pregnancy; (b) GENETIC, i.e., due to a folate/cobalamin/pyridoxine genetic defect caused by the aggregate effect of multiple mutations of folate/cobalamin/pyridoxine genes each individually having a small effect; and (c) the interaction of the folate/cobalamin/pyridoxine environmental and genetic factors (indicated above) to cause other harmful effects such as maternal teratogens and immune deficiency during gestational development. Different gene loci and different combinations of gene loci will be involved in different patients and different families. The problem of locus heterogeneity is addressed by the hypothesis that the folate/cobalamin/pyridoxine genetic defect is the aggregate effect of multiple mutations of folate/cobalamin/pyridoxine genes each of which have a relatively small effect.

The problem of mode of inheritance is addressed by the gene-teratogen model. The gene-teratogen model describes the special features of genes acting in utero; both teratogenic and modifying of specificity loci may be involved. If these effects are not taken into account, the assignment of affection status in schizophrenia pedigrees is inaccurate. Assignment of affection status is a key element in defining the mode of inheritance for all kinds of linkage mapping. Failure to assign the correct mode of inheritance is another factor that has made the linkage studies very difficult.

Finally, the DNA Polymorphism-Diet-Cofactor-Development model proposes that some of the genetic factors for schizophrenia are common in the population. In fact, subclinical deficiency of folate, pyridoxine, and cobalamin is common in the population and common among pregnant women as well. Pregnancy further increases the requirement for folate, pyridoxine, and cobalamin. Common genetic polymorphisms of folate and cobalamin genes are also known, some of them functional. Common genetic risk factors tend to be functional polymorphisms and/or mutant alleles that individually have small effects. Otherwise, they would be largely eliminated from the population by natural selection and would not be common. High disease allele frequency is yet another factor that greatly diminishes the power of a linkage study.

Besides explaining the difficulties with current linkage studies, the DNA Polymorphism-Diet-Cofactor-Development model explains all of the unusual biological and epidemiological features of schizophrenia: e.g. the decreased amount of gray matter in brain areas, the unusual birth-month effect, the geographical differences in incidence, the socioeconomic predilection, the association with obstetrical abnormalities (low birth weight and prematurity), and the association with famine and viral epidemics. Consistently, genetic linkage and cytogenetic studies in schizophrenia have implicated various chromosome regions, some of them containing folate, pyridoxine, and cobalamin genes including dihydrofolate reductase, thymidylate synthase, and transcobalamin II. The DNA Polymorphism-Diet-Cofactor-Development model predicts that folate, pyridoxine, or cobalamin gene mutations have a high frequency in schizophrenia patients or family members. Furthermore, mothers of schizophrenics are predicted to be particularly susceptible to producing one or more teratogens during pregnancy.

The present invention therefore provides methods for: (a) Diagnostic testing of schizophrenia by identifying a folate, pyridoxine, or cobalamin gene mutation or constellation of mutations in the patient, mother, and father. (b) Prevention of schizophrenia by diagnostic testing in families already affected by schizophrenia or by diagnostic population screening for folate mutations and identifying couples at risk for producing schizophrenic offspring. These pregnancies can be further monitored for risk factors, e.g. dietary folate/pyridoxine/cobalamin, plasma folate/pyridoxine/cobalamin, or red blood cell folate; plasma homocysteine or other teratogens. (c) Therapy for schizophrenia, e.g., treating the pregnant mother with folate, pyridoxine, cobalamin or other agents. The treatment can be monitored at regular intervals to determine the effect of therapy. (d) Presymptomatic treatment of schizophrenia on young children found to be susceptible to schizophrenia by diagnostic testing for folate gene mutations and other risk factors can also be treated with methylfolate or related therapeutic modalities to forestall the appearance of schizophrenia symptoms in adolescence or adulthood.

Empirical studies with methylfolate treatment of schizophrenia have shown modest clinical improvement. The DNA Polymorphism-Diet-Cofactor-Development model gives a rationale for such therapy as well as for intensive testing of related therapeutic modalities. Genetic testing will need to be carried out in such patients to gauge their likelihood of responding to therapy. In addition, the DNA Polymorphism-Diet-Cofactor-Development model gives direction and impetus toward uncovering the mechanism of fetal brain damage leading to schizophrenia.

Diagnostic testing for schizophrenia can involve testing not just the patient, but mother and father as well, for not just one factor but multiple genetic factors. For example, data for two gene loci (both folate-related genes) were used in Example 2. In this case, there were only four explanatory variables for each comparison.

In addition, risk factors appearing only during pregnancy may play a role, e.g. dietary folate which can be further monitored during the pregnancy. In certain instances, genotype data can be used as the sole explanatory variables, particularly in the case when no environmental explanatory variables are known. In such a case, the predicted probabilities will be only for the genetic component of the proband's risk of schizophrenia. In addition, schizophrenia mothers, fathers, and sibs do not necessarily have to come from the same families as the schizophrenia probands, as described in Example 2.

Of course certain genetic factors will turn out to be more common than others. This may simplify testing somewhat. Also some genetic factors may operate chiefly in the mother, while others will operate chiefly in the schizophrenic patient. This may also simplify testing. There are some approaches to assessing risk factors during a past pregnancy, e.g. current dietary history as an indicator of past diet, methionine loading as in indicator of how susceptible a mother is to raising her plasma homocysteine, assessment of other risk factors besides folate metabolism that may affect pregnancy outcome. Procedures including all of these variables are both envisioned and included in the present invention.

Thus the present invention provides a method of diagnosis of schizophrenia. In one aspect of the invention, diagnostic testing for genetic susceptibility to schizophrenia determines the probability that the proband is affected with schizophrenia due to genetic factors. This is carried out by genetic testing of a patient suspected of having schizophrenia and/or whatever informative relatives are available, e.g. mother, father, sibs, or children. The genotypes of certain folate and/or cobalamin and/or pyridoxine gene mutations or constellation of mutations (folate and/or cobalamin and/or pyridoxine gene mutations) are determined for each individual.

Since the abnormal phenotype of schizophrenia can be determined by both genetic and environmental factors and since other genetic factors besides folate/cobalamin/pyridoxine gene mutations may be involved, the presence of folate/cobalamin/pyridoxine gene mutations may be neither necessary nor sufficient to cause schizophrenia. Thus, an unaffected individual may have the same genetic risk factors as an affected individual but may lack sufficient environmental factors to cause the abnormal clinical disease. Also, an affected individual may lack folate/cobalamin/pyridoxine gene mutations but may have other related or non-related genetic risk factors that caused the schizophrenia.

Therefore folate/cobalamin/pyridoxine gene mutations are used as explanatory variables (genetic risk factors) to calculate the predicted probability that an individual has genetic susceptibility to schizophrenia due to these mutations. Genetic variation can be expected to account for approximately about half of the risk of developing schizophrenia since the concordance rate in identical twins has been estimated to be about 50%. The other half of the risk results from environmental factors due to their different positions in the uterus and to differences in the blood supply. The use of environmental factors as additional explanatory variables enhances this probability calculation, although this environmental data is more difficult to gather. Together, using both genetic and environmental explanatory variables, the predicted probability that an individual is schizophrenic may approach 1.0.

One likely situation for the use of the present methodology is in the diagnosis of a patient that has developed a psychosis. In such a case, the clinician is likely to be interested in determining the probability that this individual has schizophrenia. The number of blood relatives (preferably first degree relatives) of the patient-to-be diagnosed, both unaffected and affected, could then be determined. The number of these who would contribute a blood sample for analysis, for example, could then be ascertained. It is preferable that the patient-to-be-diagnosed also contributes a blood sample, however in certain situations, this may not be an option. The availability of dietary and epidemiological information for environmental explanatory variables, especially from the patient and the mother, can also ascertained. Of course all relevant legal and ethical rules should be followed regarding informed consent for the genetic testing.

Biological samples such as tissue or fluid samples (e.g., 7 ml of blood in an EDTA-containing vacutainer, see Example 2, below), and obtainable environmental data from the patient and family members are then collected. DNA is extracted from the sample and genotypes for alleles of folate and/or cobalamin and/or pyridoxine genes are determined. The methods for genotyping depend upon the specific genetic markers used as explanatory variables. The methods for allele determination for two genetic markers are discussed in the Examples below.

Data of the genetic and environmental explanatory variables for the patient-to-be-diagnosed (proband) and participating family members are added to a reference data set preferably consisting of well-defined schizophrenia probands and family members, and control probands, and family members for whom data is available for many explanatory variables. As an approximation the control probands themselves also can be used as the controls for each proband family member class as shown in Example 2, below. Thus, as an approximation the control probands can be used as controls for the affected probands; and/or separately for the mothers of affected probands; and/or separately for the fathers of affected probands, etc. Another example of a use of the control probands is in the evaluation and/or analysis of a particular diagnostic proband. In this case, the approximation is obtained by adding the diagnostic proband to the group of affected probands and control probands.

A model is then created consisting of the explanatory variables actually available from specific patient-to-be diagnosed and family members participating in the testing. This new combined data set (reference data set and data from patient-to-be-diagnosed with participating family members) is analyzed by binary logistic regression (e.g., using a statistical software package such as the SAS System embodied in Example 1 below, though other programs may be used) for the model chosen giving the predicted probability that a proband is affected with schizophrenia for all of the probands including the patient-to-be-diagnosed.

In a particular embodiment the model is modified and the goodness of fit for the patient-to-be-diagnosed is checked. The predicted probability that the patient-to-be-diagnosed has schizophrenia is compared with a classification table generated from the model used to determine the likelihood of false positives and false negatives.

The predicted probability that the patient-to-be-diagnosed is affected with schizophrenia, with the likelihood of false positive or false negative result, can then be forwarded to the clinician.

The methods for determining an individual's risk for developing schizophrenia taught by the present invention can be used in a variety of settings. For example, the present invention also provides a therapy for schizophrenia. Empirical studies with methylfolate treatment of schizophrenia have shown modest clinical improvement. The DNA Polymorphism-Diet-Cofactor-Development model provides a rationale for such therapy as well as for intensive testing of related therapeutic modalities, e.g. other cofactors such as cobalamin or pyridoxine. In addition, the DNA Polymorphism-Diet-Cofactor-Development model gives direction and impetus toward uncovering the mechanism of fetal brain damage leading to schizophrenia. Of course such therapy also can be provided on a case by case basis in order to gauge the likelihood of the patient of responding to such therapy, with the methodology for diagnosis of the present invention enabling the skilled practitioner to assess that likelihood.

In addition, the present invention provides a method of identifying individuals that are likely to be aided by presymptomatic treatment for schizophrenia. For example, young children found to have a high risk for susceptibility to schizophrenia by diagnostic testing can be treated with methylfolate or related therapeutic modalities to forestall the appearance of schizophrenia symptoms in adolescence or adulthood. The present invention further provides methodology for diagnostic testing for specific families already affected by schizophrenia.

The present invention further provides methodology for population screening for folate/cobalamin/pyridoxine mutations to help identify couples at risk for producing schizophrenic offspring. Subsequent or concurrent pregnancies can then be monitored for environmental risk factors, and treated with folate, cobalamin, pyridoxine or other agents and monitored at intervals for the effect of therapy. Such monitoring can include measuring levels of folate, cobalamin, pyridoxine or homocysteine in a particular tissue and/or fluid sample, such as blood.

Since schizophrenia is a developmental disorder, it is likely that these same risk factors discussed here for schizophrenia could play a role in other developmental disorders including spina bifida cystica, Tourette's syndrome, learning disorders including dyslexia, conduct disorder, attention-deficit hyperactivity disorder, bipolar illness, autism, and obsessive-compulsive disorder. Interestingly, the mode of inheritance of these disorders, like that of schizophrenia, has been difficult to determine despite the fact that a genetic component to the etiology of each has been documented. Therefore, methodology analogous to that exemplified herein for schizophrenia can be readily adapted for diagnosing and/or treating other such developmental disorders.

Nucleic Acids

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994)].

A "nucleic acid molecule" refers to the phosphate ester polymeric form of ribonucleosides (adenoside, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules including restriction fragments, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. High stringency hybridization conditions correspond to 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids, the GC percentage, and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-10.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid (e.g., a nucleotide probe or primer such as a PCR or RT-PCR primer) is at least about 12 nucleotides; preferably at least about 18 nucleotides; and more preferably the length is at least about 27 nucleotides; and most preferably at least about 36 nucleotides. Specific probes and primers that can be used to distinguish specific variants of the nucleic acids encoding the proteins involved in folate, pyridoxine, and/or cobalamin metabolism are also part of the present invention.

Such nucleotide probes and primers can be labeled or used to label complementary DNA (where appropriate) by any number of ways well known in the art including using a radioactive label, such as $^3H$, $^{14}C$, $^{32}P$, or $^{35}S$, a fluorescent label, a boron label [U.S. Pat. No. 5,595,878, Issued Jan. 21, 1997 and U.S. Pat. No. 5,876,938, Issued Mar. 2, 1999 which are incorporated by reference in their entireties], and enzymatic tags such as urease, alkaline phosphatase or peroxidase. In the case of enzyme tags, colorimetric indicator substrates are known which can be employed to provide a means visible to the human eye or spectrophotometrically, to identify specific hybridization with complementary nucleic acid-containing samples.

In a specific embodiment, the term "standard hybridization conditions" refers to a $T_m$ of 55° C., and utilizes conditions as set forth above e.g., 5×SSC. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A "signal sequence" is included at the beginning of the coding sequence of a protein to direct the protein to a particular site/compartment in the cell such as the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

Identification of Genetic Mutations

A biological sample can be obtained from an individual and/or a blood relative of the individual, and from appropriate controls, using a sample from any body component including tissue punches, body fluids, and hair, as long as the biological sample contains nucleic acids and/or proteins/peptides. Thus the DNA, mRNA, proteins or peptides of the biological sample can be used to identify mutations and/or variants in genes involved in folate, pyridoxine, or cobalamine metabolism. The present invention therefore includes methods of detecting and quantifying these nucleic acids and/or proteins/peptides that can be used to identify genetic risk factors.

In a particular embodiment the DNA is extractable. A particularly useful source of DNA is blood. For example, 2.5-40 mls of blood can be collected in a vacutainer containing EDTA. The blood sample is placed on ice and then centrifuged to separate plasma, red cells, and buffy coat. The separated fractions are then frozen at −80° C.

The DNA can be isolated from the buffy coat by a number of procedures well known in the art including using a QIAmp column DNA extraction procedure or the QIAGEN Genomic-tip method. The isolated DNA can be digested with a series of restriction enzymes, for example, and then the digested products can be hybridized with one or more particular nucleic acid probes designed from a particular gene to identify the gene and preferably to test for particular genetic mutations.

Preferably the genomic DNA can be amplified by PCR using appropriate primer pairs such as the primer pairs for the MTHFR or DHFR genes which were used in the Example below. The PCR amplified product can be sequenced directly, or alternatively be digested with one or more appropriate restriction enzymes. The resulting digested products can be separated e.g., by column chromatography, or preferably by polyacrylamide or agarose gel electrophoresis. The isolated digestion products can be compared e.g., by previously determined restriction maps, and/or alternatively, the digestion products can be sequenced directly. Alternatively, as in the case of DHFR, genetic polymorphisms can be detected through the use of restriction enzymes.

Although a restriction map of a gene is sufficient for the employment of the methods disclosed herein, in preferred embodiments the nucleotide sequences of the genes used in the testing steps are known. To this end a large sampling of such sequences are provided in Tables 2-7. (These sequences may also be used in the design of restriction maps.) Thus, initially each gene whether used separately or used in a constellation of genes is characterized by the sequencing of the wild type gene, preferably including the coding regions, introns, control sequences, and other non-coding regions. In addition, mutations of such genes found in the general population can also be characterized. With the recent advances in the sequencing of the human genome the present invention contemplates that additional sequence information will become publicly available, particularly with regard to mutations in relevant introns, and control sequences etc. which are not available in cDNA libraries. Such sequence information is fully envisioned to be incorporated into the on-going compilations of relevant DNA sequence databases of the present invention, as well as for its parallel use in the general methodology described herein. Thus DNA or mRNA or cDNA made from the mRNA can be used to identify mutations and/or variants in genes involved in folate, pyridoxine, or cobalamine metabolism.

There are many methods currently known in the art to identify variant/mutant DNA, all of which may be used in the present invention (see e.g., ich.bpmf.ac.uk/cmgs/mutdet. Such methods include but in no way are limited to direct sequencing, array sequencing, matrix-assisted laser desorption/ionization time-of-flight mass spectrometry (Malditof) [Fitzgerald et al., *Ann. Rev. Biophy. Biomol. Struct.* 24:117-140 (1995)], Polymerase Chain Reaction "PCR", reverse-transcriptase Polymerase Chain Reaction "RT-PCR", RNAase protection assays, Array quantitation e.g., as commercially provided by Affymetrix, Ligase Chain Reaction or Ligase Amplification Reaction (LCR or LAR), Self-Sustained Synthetic Reaction (3SR/NASBA), Restriction Fragment Length Polymorphism (RFLP),Cycling Probe Reaction (CPR), Single-Strand Conformation Polymorphism (SSCP), heteroduplex analysis, hybridization mismatch using nucleases (e.g., cleavase), Southern, Northerns, Westerns, South Westerns, ASOs, Molecular beacons, footprinting, and Fluorescent In Situ Hybridization (FISH). Some of these methods are briefly described below.

PCR is a method for increasing the concentration of a segment of target sequence in a mixture of genomic DNA without cloning or purification. PCR can be used to directly increase the concentration of the target to an easily detectable level. This process for amplifying the target sequence involves introducing a molar excess of two oligonucleotide primers which are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization, and polymerase extension can be repeated in order to obtain relatively high concentrations of a segment of the desired target sequence. The length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified." [Mullis (U.S. Pat. No. 4,683,195) and Mullis et al. (U.S. Pat. No. 4,683,202)]

In Ligase Chain Reaction or Ligase Amplification Reaction (LCR or LAR) four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. [Barany, Proc. Natl. Acad. Sci., 88:189 (1991); Barany, PCR Methods and Applic., 1:5 (1991); and Wu and Wallace, Genomics 4:560 (1989)] LCR has also been used in combination with PCR to achieve enhanced detection of single-base changes. Segev, PCT Public. No. WO9001069 A1 (1990).

Self-Sustained Synthetic Reaction (3SR/NASBA) is a transcription-based in vitro amplification system [Guatelli et al., *Proc. Natl. Acad. Sci.*, 87:1874-1878, 7797 (1990); Kwok et al., *Proc. Natl. Acad. Sci.*, 86:1173-1177) that can exponentially amplify RNA sequences at a uniform temperature. The amplified RNA can then be utilized for mutation detection (Fahy et al., *PCR Meth. Appl.*, 1:25-33 (1991). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo-and deoxyribonucleoside triphosphates, the target sequence undergoes repeated rounds of transcription, cDNA synthesis and second-strand synthesis to amplify the area of interest.

RFLP can be used to detect DNA polymorphisms arising from DNA sequence variation. This method consists of digesting DNA with one or more restriction endonucleases (e.g., EcoRI) and analyzing the resulting fragments by means of Southern blots [Southern, E., *Methods in Enzymology*, 69:152 (1980)], as further described by Botstein, et al., *Am. J. Hum. Genet.*, 32:314-331 (1980) and White, et al., *Sci. Am.*, 258:40-48 (1988). Since a DNA polymorphism may create or delete a restriction site, the length of the corresponding restriction fragment with any given restriction enzyme could change. Once a difference in a restriction fragment length is identified it can be used to readily distinguish a particular polymorphism from the wild type DNA. Mutations that affect the recognition sequence of the endonuclease will preclude enzymatic cleavage at that site, thereby altering the cleavage pattern of that DNA. DNAs are compared by looking for differences in restriction fragment lengths. A technique for detecting specific mutations in any segment of DNA is described in Wallace, et al.,[*Nucl. Acids Res.*, 9:879-894 (1981)]. It involves hybridizing the DNA to be analyzed (target DNA) with a complementary, labeled oligonucleotide probe. Due to the thermal instability of DNA duplexes containing even a single base pair mismatch, differential melting temperature can be used to distinguish target DNAs that are perfectly complementary to the probe from target DNAs that differ by as little as a single nucleotide. In a related technique, described in Landegren, et al., Science, 41:1077-1080 (1988), oligonucleotide probes are constructed in pairs such that their junction corresponds to the site on the DNA being analyzed for mutation. These oligonucleotides are then hybridized to the DNA being analyzed. Base pair mismatch between either oligonucleotide and the target DNA at the junction location prevents the efficient joining of the two oligonucleotide probes by DNA ligase.

When a sufficient amount of a nucleic acid to be detected is available, there are advantages to detecting that sequence directly, instead of making more copies of that target, (e.g., as in PCR and LCR). Most notably, a method that does not amplify the signal exponentially is more amenable to quantitative analysis. Even if the signal is enhanced by attaching multiple dyes to a single oligonucleotide, the correlation between the final signal intensity and amount of target is direct. Such a system has an additional advantage that the products of the reaction will not themselves promote further reaction, so contamination of lab surfaces by the products is not as much of a concern. Traditional methods of direct detection including Northern and Southern blotting and RNase protection assays usually require the use of radioactivity and are not amenable to automation. Recently devised techniques have sought to eliminate the use of radioactivity and/or improve the sensitivity in automatable formats.

One such example is the Cycling Probe Reaction (CPR) [Duck et al., BioTech., 9:142 (1990)]. CPR, uses a long chimeric oligonucleotide in which a central portion is made of RNA while the two termini are made of DNA. Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. The signal, in the form of cleaved probe molecules, accumulates at a linear rate. While the repeating process increases the signal, the RNA portion of the oligonucleotide is vulnerable to RNases that may carried through sample preparation.

Single-Strand Conformation Polymorphism (SSCP) is based on the observation that single strands of nucleic acid can take on characteristic conformations in non-denaturing conditions, and these conformations influence electrophoretic mobility. [Hayashi, *PCR Meth. Appl.*, 1:34-38, (1991). The complementary strands assume sufficiently different structures that one strand may be resolved from the other. Changes in sequences within the fragment will also change the conformation, consequently altering the mobility and allowing this to be used as an assay for sequence variations (Orita, et al., *Genomics* 5:874-879, (1989). The SSCP process involves denaturing a DNA segment (e.g., a PCR product) that is labeled on both strands, followed by slow electrophoretic separation on a non-denaturing polyacrylamide gel, so that intra-molecular interactions can form and not be disturbed during the run. This technique is extremely sensitive to variations in gel composition and temperature.

In Fluorescent In Situ Hybridization (FISH), specific probes are designed which can readily distinguish the wild-type gene from the variant/mutant gene. Such methodology allows the identification of a variant/mutant gene through in situ hybridization (U.S. Pat. No. 5,028,525, Issued Jul. 2, 1991; U.S. Pat. No. 5,225,326, Issued Jul. 6, 1993; and U.S. Pat. No. 5,501,952, Issued Mar. 26, 1996. FISH does not require the extraction of DNA. In addition, procedures for separating fetal blood cells from maternal blood cells are well known in the art allowing the fetus and the mother to be analyzed from the same body fluid sample (see U.S. Pat. No. 5,629,147, Issued May 13, 1997).

Similarly, antibodies raised against specific mutations and/or variants in the gene products of the genes involved in folate, pyridoxine, or cobalamine metabolism can be used to identify specific polymorphisms. Alternatively, antibodies raised against the wild type proteins can be used to detect and/or quantify the amount of wild type protein present in a given biological sample. In the case in which cross-reacting protein isn't synthesized by the cells of an individual, or is synthesized in significantly lower amounts than those of control subjects, such determinations can be used to identify a genetic risk factor. In addition, these antibodies can be used in methods well known in the art relating to the localization and activity of the gene products, e.g., for Western blotting, imaging the proteins in situ, measuring levels thereof in appropriate physiological samples, etc. using any of the detection techniques known in the art. Furthermore, such antibodies can be used in flow cytometry studies, in immunohistochemical staining, and in immunoprecipitation which serves to aid the determination of the level of expression of a protein in the cell or tissue.

In the particular instance when the gene product is an enzyme, e.g., dihydrofolate reductase, the enzymatic activity of a biological sample can be indicative of the presence of a genetic risk factor. In a particular embodiment, a decrease in an enzyme activity that is associated with folate, pyridoxine, or cobalamine metabolism can be indicative of the presence of the genetic risk factor. Such assays can be performed on multiple samples such as on a microplate reader [Wideman et al., Clin Chem. 45:223-228 (1999)].

Model 1

The Gene-Teratogen Model for the Inheritance Pattern of Certain Developmental Disorders Introduction It has long been known, e.g. from extensive studies of exogenous teratogens in inbred mice [Funnell and Chernoff, Gene-teratagen interactions: an approach to understanding the metabolic basis of birth defects, In Pharmacokinetics in Teratogenesis, Vol. II:97-109 *Experimental Aspects In Vivo and In Vitro*, CRC Press, Inc, Boca Ratan, Fla. (1987)], that teratogens may be influenced by genetic factors. It is less well known that the same gene defect may cause different clinical disorders depending upon whether the metabolic effect of the gene defect is exerted during gestation in utero or during postnatal life. However, the consequences of gene-teratogen interactions in human pedigrees have not been extensively explored, especially the consequences for the use of linkage mapping to identify an unknown gene acting in utero to cause a developmental disorder. A number of common human developmental disorders have been shown to have a genetic component to their etiology. However, for certain developmental disorders, the mode of inheritance has been difficult to determine and linkage studies have met with unexpected difficulties or have achieved limited success. These developmental disorders include spina bifida cystica [Chatkupt, *Am J Med Genet*, 44:508-512 (1992)], Tourette's syndrome & related disorders, e.g. obsessive-compulsive disorder and chronic multiple tics syndrome [Pauls, *Adv Neurol*, 58:151-157 (1992); McMahon et al., *Adv Neurol*, 58:159-165 (1992); Heutink et al., *Am J Hum Genet*, 57:465-473 (1995); Grice et al., *Am J Hum Genet*, 59:644-652 (1996)], learning disorders, including dyslexia [Lewis, et al., *Behav Genet*, 23:291-297 (1993); Pennington, *J Child Neurol* 10 Suppl, 1:S69-S77 (1995)], conduct disorder [Lombroso et al., *J Am Acad Child Adolesc Psychiatry*, 33:921-938 (1994)], attention-deficit hyperactivity disorder [Lombroso et al., *J Am Acad Child Adolesc Psychiatry*, 33:921-938 (1994)], bipolar illness [Baron, *Acta Psychiatr Scand*, 92:81-86 (1995); Benjamin and Gershon, *Biol Psychiatry*, 40:313-316 (1996); Risch and Botstein, *Nature Genet*, 12:351-353 (1996); Jamison and McInnis, *Nature Med*, 2:521-522 (1996); Morell, *Science*, 272:31-32 (1996)], schizophrenia [Owen, *Psychol Med*, 22:289-293 (1992); Cloninger, *Am J Med Genet*, 54:83-92 (1994); Lander and Kruglyak, *Nature Genet*, 11:241-247 (1995); Baron, *Acta Psychiatr Scand*, 92:81-86 (1995); Benjamin and Gershon, *Biol Psychiatry*, 40:313-316 (1996); Baron, *Am J Med Genet*, 67:121-123 (1996)], autism [Lombroso et al., *J Am Acad Child Adolesc Psychiatry*, 33:921-938 (1994)], and obsessive-compulsive disorder in adults [Lombroso et al., *J Am Acad Child Adolesc Psychiatry*, 33:921-938 (1994)]. A recent article [Moldin, *Nature Genet*. 17:127-129 (1997)] has reviewed "The maddening hunt for madness genes."

The present model addresses the question of the mode of inheritance of certain developmental disorders and proposes the "gene-teratogen model." The model suggests that the mode of inheritance of genes acting prenatally may in some cases be fundamentally different from that of genes acting postnatally. Even the same gene acting prenatally may produce a different disorder from that gene acting postnatally. The inheritance pattern in the gene-teratogen model is simple, but from the perspective of the patient with the developmental disorder is neither dominant nor recessive. Some disorders regarded as multifactorial, polygenic, or oligogenic may have this mode of inheritance. In the gene-teratogen model, genetically determined teratogen production by the mother during pregnancy damages the fetus producing the abnormal phenotype of a developmental disorder. The model is illustrated with two types of loci, 1. a teratogenic locus acting in the mother, and 2. a modifying or specificity locus acting in the fetus. Damage by the teratogen is influenced also by environmental factors. The model is interesting because it is simple and because teratogenic loci will be difficult to locate by parametric or non-parametric linkage mapping techniques due to misspecification of the affection status of both mother and affected children. A study design is suggested for identifying teratogenic loci. An example of the gene-teratogen model is the major intrauterine effect seen in offspring of phenylketonuric mothers. Certain developmental disorders whose mode of inheritance has been difficult to determine or whose genetic factors have been difficult to locate are candidates for the gene-teratogen model, including spina bifida cystica, Tourette's syndrome, learning disorders including dyslexia, conduct disorder, attention-deficit hyperactivity disorder, bipolar illness, schizophrenia, autism, and obsessive-compulsive disorder.

The Gene Teratogen Model

The model is described in Table 1 using two kinds of loci: a "teratogenic" locus and a "modifying" or "specificity" locus. The gene-teratogen model requires a teratogenic locus. One or more modifying or specificity loci may or may not be present. Also, two types of phenotypes are defined: 1. the teratogen-induced phenotype; and 2. the teratogenic phenotype, i.e., the phenotype of a mother that produces a teratogenic effect during pregnancy. The two phenotypes are different for the teratogenic locus but are identical for the modifying or specificity loci.

TABLE 1

DIAGRAM OF THE GENE-TERATOGEN MODEL

| Grandparents: | Maternal Grandmother AabbCCdd | Maternal Grandfather AaBbCcdd | Paternal Grandmother AAbbCcDd | Paternal Grandfather AAbbCCdd |
|---|---|---|---|---|
| Parents: | | Mother aaBbCcdd | | Father AAbbCcDd |
| Child: | | Child (fetus) with developmental disorder AabbccDd | | |
| locus A: | | teratogenic locus, recessive, acting in the mother to cause intrauterine teratogenic damage to the fetus. | | |
| locus B: | | teratogenic locus, dominant, acting in the mother to cause intrauterine teratogenic damage to the fetus. | | |
| locus C: | | modifying or specificity locus, recessive, acting in the fetus. | | |
| locus D: | | modifying or specificity locus, dominant, acting in the fetus. | | |

The teratogenic locus may be dominant (locus A) or recessive (locus B). This locus acts in the mother during pregnancy to cause an intrauterine teratogenic effect in the fetus. The teratogenic effect may result from the production of an endogenous teratogen, from potentiation of an exogenous teratogen, from a metabolic deprivation or imbalance or from some other mechanism. Only one teratogenic locus is required; both locus A and locus B are shown on the same diagram for simplicity. A specificity or modifying locus may be dominant (locus C) or recessive (locus D). Such a locus acts during pregnancy or after to modify the extent of the developmental damage done by the teratogenic locus or even to prevent or repair the damage. For example, for a teratogen acting at a certain time in development, locus C or D may determine whether brain or kidney is damaged, which structures of the brain are damaged, or whether damage occurs at all.

1. Locus A, recessive teratogenic locus, acting in the mother: The child is the patient with the abnormal phenotype of a specific developmental disorder, while mother, father, and grandparents do not have the abnormal phenotype of that disorder (Table 1). Locus A acts in the mother during pregnancy causing her to produce the teratogenic effect that damages the developing fetus leading to the developmental disorder either in the fetus or postnatally in the child or adult. Since this locus is recessive in action, the mother, a homozygote (aa) for the disease allele, is the genetic "patient." Her abnormal phenotype, the "teratogenic phenotype", is the trait of producing the teratogenic effect during pregnancy. Her fetus, damaged by the teratogenic effect in utero, does develop the teratogen-induced phenotype. However, the fetus is only a heterozygote (Aa) at locus A and thus lacks both the abnormal homozygous genotype at locus A and the abnormal teratogenic phenotype; e.g., if the fetus is a daughter, she will not produce the teratogenic effect later during pregnancy. Thus, the fetus is affected with the developmental disorder but is not the genetic "patient." Locus A, acting through a teratogenic effect, cannot be the only etiological factor for the developmental disorder. If it were, then all pregnancies of an aa mother would have the teratogen-induced phenotype which is not the case. Environmental and/or other genetic factors, are required. An aa father will have the abnormal genotype, but not the abnormal teratogenic phenotype because he could never become pregnant.

2. Locus B, dominant teratogenic locus acting in the mother: The situation is the same as for locus A except that locus B is dominant in action (Table 1). The mother has the abnormal genotype, Bb, and the abnormal teratogenic phenotype. The fetus has the teratogen-induced phenotype but in the instance shown (Table 1) has neither the abnormal genotype, the teratogenic phenotype, nor even a copy of the disease allele. The maternal grandfather shown (Table 1) has the abnormal genotype, Bb, but does not have the teratogenic phenotype because he could never become pregnant.

3. Environmental effects: The teratogenic effect is modified by environmental factors, e.g. maternal dietary factors, infection, or ingestion of teratogen. These environmental factors may interact with locus A or B or may act independently. From the perspective of the fetus later to develop the developmental disorder (teratogen-induced phenotype), intrauterine teratogenic is an environmental not a genetic effect.

4. Modifying or Specificity Loci Acting in the Fetus, Loci C & D: These loci may interact with the teratogenic locus or the environmental factors to increase or decrease their effect, or alternatively could act independently. Such genetic factors may be recessive (locus C) or dominant (locus D). Genotypes and phenotypes of locus C and D behave conventionally with respect to the developmental disorder. For locus C and D, the fetus is with the developmental disorder is now the genetic "patient". Maternal teratogenic in utero is an environmental effect. It is thus possible that the same gene locus could act in part as a teratogenic locus and in part as a modifying or specificity locus.

Discussion

The Example of Phenylketonuria: An example of the gene-teratogen model is the major intrauterine effect in maternal phenylketonuria (PKU). Phenylketonuria itself is a recessive postnatal disorder. Untreated homozygous PKU mothers and fathers both have elevated blood phenylalanine (hyperphenylalaninemia). However, heterozygous offspring of untreated PKU mothers (but not fathers) have an abnormal phenotype. [Koch et al., *Acta Paediatr Suppl*, 407:111-119 (1994); Allen et al., *Acta Paediatr Suppl*, 407:83-85 (1994); Abadie et al., *Archives Pediatr*, 3:489-486 (1996)]. Thus the elevated blood phenylalanine or other metabolite(s) in the mother acts as a teratogen for the fetus. Note that the fetus of an untreated phenylketonuric mother does not have the phenotype of PKU (the "teratogenic phenotype"), but has a different phenotype (the "teratogen-induced phenotype"). Phenylketonurics [Menkes, *Textbook of Child Neurology*, Lea & Febiger, Philadelphia (1990)] are normal at birth and develop a progressive disorder postnatally characterized by vomiting, eczema, seizures (infantile spasms with hypsarrythmia on electroencephalography), and mental retardation. The fetus of an untreated phenylketonuric mother [Menkes, *Textbook of Child Neurology*, Lea & Febiger, Philadelphia (1990)] has a congenital non-progressive disorder of fetal origin characterized by microcephaly, abnormal facies, mental retardation, congenital heart disease, and prenatal and postnatal growth retardation. The PKU phenotype is a postnatal degenerative disorder; the phenotype of the PKU intrauterine effect is a developmental disorder. The teratogenic effect is not dependent upon the fetal genotype, although the fetus is an obligate heterozygote since the mother is a homozygote for phenylketonuria and the father (usually) has the normal genotype. Thus, in phenylketonuria, a mutation at the same gene locus causes two distinct disorders depending upon whether the period of abnormal gene action is prenatal or postnatal. A fetus with the abnormal homozygous genotype who is carried by a heterozygous mother is protected in utero, but develops PKU postnatally. A heterozygous fetus carried by a mother with the abnormal homozygous genotype is damaged in utero when the mother's genotype predominates, but is protected from PKU postnatally by its own genotype.

An Example from Studies in Inbred Mice: Funnell and Chernoff [Gene-teratagen interactions: an approach to understanding the metabolic basis of birth defects, In Pharmacokinetics in Teratogenesis, Vol. II:97-109 *Experimental Aspects In Vivo and In Vitro*, CRC Press, Inc, Boca Ratan, Fla. (1987)] have reviewed a group of elegant experiments in inbred mice documenting that differences in susceptibility to exogenous teratogens can be regarded as a genetic trait that is determined by susceptibility or liability genes of either the maternal or fetal genotype [Funnell and Chernoff, Gene-teratagen interactions: an approach to understanding the metabolic basis of birth defects, In Pharmacokinetics in Teratogenesis, Vol. II:97-109 *Experimental Aspects In Vivo and In Vitro*, CRC Press, Inc, Boca Ratan, Fla. (1987)]; Funnell et al., *Am J. Med. Genet.* 70:303-311 (1997); Bennett et al., *Epilepsia* 38:415-423 (1997)]. For example, sensitivity to acetazolamine-induced ectrodactyly is determined by the presence of three genes, and the fetus must be homozygous for the recessive allele at all three loci in order to express the malformation. However, the inbred mouse models used do not mirror the human situation in at least three respects. First, the human population is an outbred population compared to these inbred mouse models. Consequently, the relevant genotypes may be highly variable among members of different families. Second, the inbred mouse experiments address the question of exogenous rather than endogenous teratogens. Third, the inbred mouse studies rely upon known or candidate susceptibility loci, whereas in humans, the problem has been to locate and identify disease unknown loci largely by using linkage mapping techniques.

Implications for Linkage Mapping:

Teratogenic Locus (LocusA or B): The gene-teratogen model has major implications for linkage mapping done with either parametric or non-parametric methods. The problem for both methods is incorrect assignment of affection status. In the lod score method, a genetic model of the disease is constructed and an affection status is assigned to each member of the pedigree. If the genetic model specified is wrong, the linkage results may be falsely positive or falsely negative [Terwilliger and Ott, *Handbook of Human Genetic Linkage*, Johns Hopkins Univ. Pr., Baltimore (1994)]. In developmental disorders resulting from the gene-teratogen model, the phenotype assignment for lod score analysis will be incorrect. The patient with the developmental disorder will be assigned the affected phenotype, whereas the patient is actually affected only for the teratogen-induced phenotype, but is unaffected for the teratogenic phenotype. Likewise, the mother will be assigned the unaffected phenotype for linkage analysis. Actually, she is unaffected only for the teratogen-induced phenotype, but is affected for the teratogenic phenotype. Lod scores should increase when phenotype assignments have been corrected. However, apparently dominant inheritance may in fact turn out to be pseudodominant if the mutant allele is common in the population. For non-parametric analysis, a similar misassignment occurs. In the case of affected sib-pairs, the affected sibs will be assigned the affected phenotype. Actually, the sibs are affected only for the teratogen-induced phenotype, but are unaffected for the teratogenic phenotype. The mother will be assigned the unaffected or unknown phenotype. Actually, she is unaffected only for the teratogen-induced phenotype but is affected for the teratogenic phenotype. Thus, the "affected sib-pair" families are likely to turn out to contain only a single sporadic case, since the only individual in the kindred affected with the teratogenic phenotype will be the mother.

For the transmission/disequilibrium test (TDT) [Spielman et al., *Am J Hum Genet*, 52:506-516 (1993); Ewens and Spielman, *Am J Hum Genet*, 57:455-464 (1995)] the patient with the developmental disorder will be assigned the affected phenotype. Actually, the patient will be affected only for the teratogen-induced phenotype but will be unaffected for the teratogenic phenotype. The mother will be assigned the unaffected or unknown phenotype. Actually, she is unaffected only for the teratogen-induced phenotype but is affected for the teratogenic phenotype. The expectation of TDT is that alleles of a linked locus will show distortion from random transmission from mother (or father) to the patient. Since the patient is unaffected for the teratogenic phenotype, no transmission distortion from mother (or father) to child will be observed. Transmission distortion for alleles of a teratogenic locus will in fact occur from the mother's parents to the mother, the actual patient for the teratogenic phenotype. But this will not be looked for because the phenotypes have been wrongly assigned. In addition, grandparents of the patients with the developmental disorder have probably not had DNA collected. Therefore, for the TDT, negative results may occur for disease alleles of a teratogenic locus because incorrect phenotype assignments will have been made. When correct phenotype assignments have been made, transmission distortion to the mother from her parents should be expected for disease alleles of a teratogenic locus. Analogous misassignments are made in allelic association and haplotype relative-risk analyses [Falk and Rubinstein, *Ann Hu, Genet*, 51:227-

233 (1987); Terwilliger and Ott, *Hum Hered*, 42:337-346 (1992); Thomson, *Am J Hum Genet*, 57:487-498 (1995)].

Modifying or Specificity Loci (Locus C and/or D): Since these loci behave in a conventional fashion, the phenotype assignments will be correct. Consequently, genes identified by conventional parametric or non-parametric linkage studies are likely to be modifying or specificity loci. An important question for linkage mapping is the relative contribution to the abnormal phenotype of the developmental disorder made by the teratogenic locus versus that of a modifying or specificity locus. If the effect of a teratogenic locus is small, then loci identified by conventional linkage studies will be specificity or modifying loci and the mode of inheritance will be Mendelian or multifactorial. If a teratogenic locus makes a major contribution to phenotype, then linkage mapping studies will not give a consistent answer and the mode of inheritance will be difficult to determine.

The presence of a teratogenic locus may be suspected if the maternal contribution to phenotype is different from or greater than the paternal contribution. For example, the mother's relatives of spina bifida infants more frequently have affected children than the father's relatives. Suggested explanations for this observation have been mitochondrial inheritance, maternal effect, or genomic imprinting [Chatkupt, *Am J Med Genet*, 44:508-512 (1992)]. The operation of a teratogenic locus is another explanation and is itself a form of maternal effect. For a recessive teratogenic locus, the mother's sisters would be at greatest risk of having offspring with the teratogen-induced phenotype.

Implications for Definition of Phenotype: All the pregnancies of a mother with the teratogenic phenotype are at risk for the developmental disorder, the teratogen-induced phenotype. Yet only a few of the fetuses will be affected by the developmental disorder because of the action of environmental factors and/or the modifying or specificity loci. The action of the environmental factors is fully quantitative: depending upon the amplitude of the environmental effect, a mild, moderate, or severe teratogen-induced phenotype may result. In addition, the environmental factor may act at different times in fetal development producing qualitatively different phenotypes. Thus, quantitatively or qualitatively different teratogen-induced phenotypes may result from pregnancies of the same mother with the teratogenic phenotype. In addition, the action of the modifying or specificity loci may produce quantitatively or qualitatively different phenotypes in offspring of the same couple. Such different phenotypes may be diagnostically classified as different disorders. This may complicate attempts at associating specific loci with a specific teratogen-induced phenotype. All of the teratogen-induced phenotypes resulting from pregnancies of a mother with the teratogenic phenotype modified only by environmental factors are genetically indistinguishable. However, such teratogen-induced phenotypes affected also by the various modifying or specificity loci segregating among the offspring of a single couple are only partially genetically related.

Methods to Identify Teratogenic Loci: One effective approach to finding a putative teratogenic locus is to carry out non-parametric linkage studies of families consisting of a patient affected with the developmental disorder, the patient's two (unaffected) parents, and the patient's four (unaffected) grandparents (Table 1). In such a family, the mother is the genetic patient but the other family members are not. Now, the mother's nuclear family (the mother and her parents) is compared with the father's nuclear family (the father and his parents). In a haplotype relative risk study, the disease allele(s) of the teratogenic locus will occur more frequently in the mother compared with other alleles of her parents; the disease allele(s) of the teratogenic locus will not occur more frequently in the father compared with other alleles of his parents. In a transmission/disequilibrium test, transmission distortion will be seen for the disease allele(s) of a teratogenic locus in the mother's nuclear family but not in the father's nuclear family. In an allelic association study, the disease allele will occur more frequently in mothers, patients (with the developmental disorder), and patient's sibs (both affected and unaffected) than in unrelated control individuals. Disease allele frequency in fathers will not be distinguishable from that in control individuals.

Certain developmental disorders with a genetic component to etiology, whose mode of inheritance has been difficult to determine or whose genetic factors have been difficult to locate, including those mentioned earlier, are candidates for the gene-teratogen model.

Model 2

The DNA Polymorphism-Diet-Cofactor-Development Hypothesis for Schizophrenia and Other Developmental Disorders Folate metabolism is complex. At least 30 gene loci are involved in absorption, transport, and metabolism of folate, and these are regulated by additional gene loci. Any of these is potentially a genetic risk factor for schizophrenia, although MTHFR and DHFR are particularly good candidates. Likewise, genes encoding proteins involved in the pathways of other vitamin-cofactors may be genetic risk factors.

Two cofactors that may be of particular potential importance are cobalamin and pyridoxine. Cobalamin is relevant because its metabolism is closely intertwined with that of folate. For example, cobalamin is required for the activity of methionine synthase (MTR), a folate-related enzyme. Decreased cobalamin can affect folate metabolism through the folate trap. Pyridoxine is relevant because the pyridoxine-dependent enzyme cystathionine beta-synthase (CBS), along with the cobalamin-dependent enzyme MTR and folate pathways including MTHFR and DHFR all participate in catabolism of homocysteine, an amino acid that is suspected of being a teratogen during pregnancy. Also, kynureninase, an important enzyme affecting niacin metabolism and serotonin synthesis is pyridoxine-dependent. Therefore, mutations of the genes encoding such proteins, especially common polymorphisms, could play a role in the cause of schizophrenia.

Since folate, cobalamin, and pyridoxine are all dietary constituents, the dietary content of these cofactors could be lead to an "environmental" generation of a risk factor for schizophrenia. In addition genes encoding proteins involved in folate, cobalamin, and pyridoxine metabolism and catabolism could be genetic risk factors for schizophrenia. Thus, the cofactors and the proteins involved in pathways relevant to these cofactors can potentially have either or both environmental and genetic effects on the susceptibility of an individual on schizophrenia.

Since the genetic aspect of schizophrenia differs so profoundly from other disorders which have been identified by linkage mapping techniques, it is clear that a new model for the genetic connection to schizophrenia is required. Therefore, the DNA Polymorphism-Diet-Cofactor-Development (DDCD) hypothesis, is disclosed herein.

The DDCD hypothesis is that interacting genetic and environmental factors affecting the metabolism of folate, cobalamin, or pyridoxine or all of these, play a role in the etiology of schizophrenia. The genetic effect results from the aggregate effect of multiple mutations that individually, for the most part, have small effects on folate-, cobalamin- or pyridoxine-related genes, some of which will be common in the population, and can act in utero. Environmental factors include dietary folate and cobalamin and pyridoxine. If schizophrenia results from mild deficiency during fetal development of dietary folate, cobalamin, or pyridoxine potentiated by mild genetic susceptibility mutations of genes related to these cofactors and by pregnancy, then this would be difficult to document by linkage mapping techniques. An example of interaction of genetic and environmental factors is that genetic factors are important for incorporating dietary folate; the enzyme dihydrofolate reductase is required for conversion of dietary folate to folinic acid thus allowing dietary folate to enter the body's metabolic pathways. Another example is that folate and cobalamin requirements increase during pregnancy; thus pregnancy could potentiate the effects of mild genetic defects of mother, fetus, or both. Deficiencies of a vitamin are often part of a broader dietary deficiency affecting multiple nutrients in addition to the vitamin being measured.

Locus Heterogeneity: The metabolic pathways of folate, cobalamin, and pyridoxine are complex and related to each other. Multiple gene loci code for the enzymes and transport proteins are required (Tables 2-7). Thus, a defect of folate, cobalamin, or pyridoxine metabolism could result from the aggregate effect of multiple mutations each of relatively small effect interacting with environmental factors. Different individuals might have different combinations of mutations. Such a metabolic defect would be difficult to detect by linkage mapping techniques because of locus heterogeneity.

Alternatively, even if one genetic defect were sufficient to make an individual more susceptible to having schizophrenic offspring, for example, because of the large number of potential genetic factors, and the corresponding importance of environmental factors, elucidation of such an individual genetic defect would still be difficult unless, of course, the genetic defect caused a major effect. The difficulty in elucidating an individual genetic defect is magnified when the genetic factor acts in the mother, and not in the schizophrenic patient.

High Disease Allele Frequency: Numerous mutational variants of folate and cobalamin genes are known. Some of these have functional significance and in addition are sufficiently common in a given population to be regarded as genetic polymorphisms. However, these common alleles are unlikely to have a major harmful effect by themselves, for if they did they would become uncommon in the population in the absence of selection effects, and would likely appear as Mendelian disorders. Thus, the folate, cobalamin, or pyridoxine disease alleles related to schizophrenia would appear to be more likely those of minor deleterious effect or those with harmful effect only in the presence of environmental deficiencies or pregnancy. Such disease genes of high population frequency will be difficult to detect by linkage mapping methods because high disease allele frequency decreases the power of linkage studies [Terwilliger and Ott, *Handbook of Human Genetic Linkage*, John Hopkins Univ. Press, Baltimore, (1994)].

Developmental Genes: Folate, cobalamin, and pyridoxine defects act prenatally as well as postnatally. Folate, cobalamin, and pyridoxine metabolism are crucial for DNA synthesis and cell division, which are of disproportionate importance during brain development. Some defects of folate, cobalamin, or pyridoxine metabolism elevate blood homocysteine, a toxic and potentially teratogenic substance. Genes acting in the mother to damage the developing fetus, e.g. via the gene-teratogen model (Model 1, above), have a mode of inheritance that is neither dominant nor recessive with respect to the fetus. Attempts to assign a mode of inheritance in this situation will be unsatisfactory because affection status would be incorrectly assigned. The mode of inheritance of a developmental disorder resulting from a teratogenic locus would be regarded as either multifactorial or unknown. This is the situation with schizophrenia whose mode of inheritance is unknown. Use of an incorrect genetic model decreases the power of a linkage studies [Terwilliger and Ott, *Handbook of Human Genetic Linkage*, John Hopkins Univ. Press, Baltimore, (1994)].

Genes of Folate Metabolism: Folate metabolism is extremely complex [Rosenblatt, In: *The Metabolic and Molecular Bases of Inherited Disease*, Scriver et al. (eds), New York: McGraw-Hill, pp. 3111-3128 (1995); Mudd et al., In: *The Metabolic and Molecular Bases of Inherited Disease*, Scriver et al. (eds), New York: McGraw-Hill pp. 1279-1327 (1995)]. At least 30 gene loci (Table 2) have been identified as folate-related. These contribute to folate mediated 1-carbon transfer reactions, binding, transport and metabolism of folate, and other functions. A number of these have been cloned and localized to a chromosomal region (Table 3).

TABLE 2

FOLATE-RELATED GENES/ENZYMES/TRANSPORTERS[a]

| Folate-Related Genes/Enzymes/Tranporters[a] | SEQ ID NO: |
|---|---|
| methylenetetrahydrofolate reductase, MTHFR, MIM 236250 | 1 |
| methionine synthase (methyltetrahydrofolate:L-homocysteine S-methyltransferase), MTR, MIM 156570 | 2 |
| dihydrofolate reductase, DHFR, MIM 126060 | 3 |
| folylpolyglutamate synthase, FPGS, MIM 136510 | 4 |
| folate receptor 1, folate receptor alpha (FOLR1, adult; FR-alpha), MIM 136430 | 5 |
| folate receptor 2, folate receptor beta (FOLR2, fetal; FR-beta), MIM 136425(a.a.) | 6 |
| folate receptor 2-like (FOLR2L, fetal-like), MIM-none | |
| folate receptor gamma (FR-gamma), MIM 602469 | 7 |
| serine hydroxymethyltransferase 1, SHMT1, MIM 182144 | 8 |
| methylenetetrahydrofolate dehydrogenase, methenyltetrahydrofolate cyclohydrolase, 10-formyltetrahydrofolate synthetase (trifunctional enzyme, MTHFD), MIM 172460 | 9 |
| serine hydroxymethyltransferase 2, SHMT2, MIM 138450 | 10 |
| thymidylate synthase, TYMS, MIM 188350 | 11 |
| GAR (5-phosphoribosylglycineamide) transformylase, GART, MIM 138440 | 12 |
| reduced folate carrier-1, RFC1. Probably identical to micromolar membrane transport protein, intestinal folate carrier-1 (IFC1), and neutral folate transport protein. MIM 600424 | 13 |
| cystathionine beta-synthase, CBS, MIM 236200 | 14 |
| AICAR (5-phosphoribosyl-5-aminoimidazole-4-carboxamide) transformylase glutamate formiminotransferase, MIM 229100 forminotetrahydrofolate cyclodeaminase | 15 |
| 5,10-methenyltetrahydrofolate synthetase 10-formyltetrahydrofolate dehydrogenase, Mim 600249 glycine cleavage pathway (SHMT plus three enzymes): MIM 238331 | 16 |
| Gly-decarboxylase MIM 238300 | 17 |
| H-Protein MIM 238330 | 18 |
| T-Protein MIM 238310 | 19 |
| cblG (affects function of MTR), MIM 250940 | |
| methionine adenosyltransferase 1, MAT1A, (ATP: L-methionine S-adenosyltransferase), MIM 250850 | 20 |
| pteroyl polyglutamate hydrolase ("conjugase"), form 1 | |
| pteroyl polyglutamate hydrolase ("conjugase"), form 2 | |
| NAD-dependent enzyme methylene tetrahydrofolate dehydrogenase cyclohydrolase(a.a.) | 21 |

TABLE 2-continued

FOLATE-RELATED GENES/ENZYMES/TRANSPORTERS[a]

| Folate-Related Genes/Enzymes/Tranporters[a] | SEQ ID NO: |
|---|---|
| methionine adenosyltransferase 2, MAT2A, MIM 601468 | 22 |
| 5-methyltetrahydrofolate-homocysteine methyltransferase reductase (MTRR) MIM 602568; #Variant in MTRR linked to cblE MIM 236270 methyltranferases | 23 |
| S-adenosylmethionine decarboxylase, MIM 180980 | 24 |
| decarboxylated S-adenosylmethionine:putrescine propyl-aminotransferase or spermidine synthetase(a.a.) | 25 |
| S-adenosylhomocysteine hydrolase, MIM 180960 | 26 |
| betaine-homocysteine methyltransferase dimethylthetin-homocysteine methyltransferase | 27 |
| gamma-cystathionase (L-cystationine cysteine-lyase (deaminating)), MIM 602888 | 28 |
| folic acid transport protein, MIM 229050 | |
| DHFR (exon 6 and 3' flanking region) | 30 |
| kynureninase | 35 |
| human DHFR, exons 1 and 2 [Chen et al., J. Biol. Chem. 259: 3933-3943 (1984)] | 36 |

[a]listed with alternate names, abbreviations, and MIM numbers;

cblE is a phenotype for a particular group of disorders of folate/cobalamin metabolism.

(a.a.) indicates the amino acid sequence

TABLE 3
LOCALIZED GENE LOCI RELATED TO FOLATE METABOLISM

| Gene/enzyme/transport protein | Location | References |
|---|---|---|
| MTHFR | 1p36.3 | Goyette et al., (1994); *, ** |
| MTR | 1q43 | Cook and Hamerton, (1979); Mellman et al., (1979) ** |
| DHFR | 5q11.2-13.2 | Weiffenbach et al., (1991) Gilliam et al. (1989b) *, ** |
| FPGS | 9cen-q34 | Jones and Kao (1984); Walter et al. (1992) *, ** |
| MAT | 10q22 | ** |
| FR | 11q13.3-q14.1 | Lacey et al. (1989), Ragoussis et al, (1992); Ratnum et al. (1989); Walter et al. (1992); * |
| | 11q13.3-113.5 | Ragoussis et al, (1992), ** |
| SHMT2 | 12q12-q14 | Garrow et al., (1993); Law and Kao, (1979) * |
| | 12q13 | ** |
| MTHFD | 14q24 | Rozen et al., (1989), Jones et al. (1981), *, ** |
| LCCL | 16pter-qter | *, ** |
| SHMT1 | 17p11.2 | Garrow et al., (1993) *, ** |
| TYMS | 18p11.31.-p11.22 | * |
| | 18p11.32 | Hori et al., (1990); Silverman et al., (1993) |
| SAHH | 20cen-q13.1 | * |
| GART | 21q22.1 | McInnis et al. (1993) Schild et al. (1990) Avrarmopoulos et al. (1993) Goto et al. (1993) *, ** |
| RFC1 | 21q22.2-22.3 | Moscow et al., (1995) |
| CBS | 21q22.3 | Munke et al., (1988) | notes:
MTHFR = methylenetetrahydrofolate reductase.
MTS = methionine synthase.
DHFR = dihydrofolate reductase.
FPGS = folylpolyglutamate synthase.
MAT = methionine adenosyltransferase, (ATP: L-methionine S-adenosyltransferase).
FR = folate receptor complex: FR-alpha = FOLR1 = folate receptor 1, adult; FR-beta = FOLR2 = folate receptor 2, fetal; FR-gamma; FOLR2L = folate receptor 2-like.
SHMT2 = serine hydroxymethyltransferase 2, mitochondrial.
MTHFD = 5,10-methylenetetrahydrofolate dehydrogenase, 5,10-methylenetetrahydrofolate cyclohydrolase, 10-formytetrahydrofolate synthase (trifunctional enzyme).
LCCL = gamma-cystathionase (L-cystathionine cysteine-lyase (deaminating).
SHMT1 = serine hydroxymethyltransferase 1, soluble.
TYMS = thymidylate synthetase.
SAHH, S-adenosylhomocysteine hydrolase.
GART = phosphoribosylglycineamide formyltransferase.
RFC1 = reduced folate carrier-1 (possibly identical to IFC1, intestinal folate carrier-1).
CBS = cystathionine beta-synthase.
Location information from GOD (*), from MIM (**).
Goyette et al., Nat. Gen. 7: 195-200 (1994)
Cook and Hamerton, Cytogenet Cell Genet. 25: 9-20 (1979)
Mellman et al., Proc. Natl. Acad. Sci. 76: 405-409 (1979)
Weiffenbach et al., Genomics 10: 173-185 (1991)
Gilliam et al. Genomics 5: 940-944 (1989b)
Jones and Kao Cytogenet Cell Genet. 37: 499 (1984)
Walter et al. Ann. Hum. Genet. 56: 212 (1992)
Lacey et al. Am. J. Med. Genet. 60: 172-173 (1989)
Ragoussis et al, Genomics 14: 423-430 (1992)
Ratnum et al. Biochem. 28: 8249-8254 (1989)
Garrow et al. J. Biol. Chem. 268: 11910-11916 (1993).
Law and Kao, Cytogenet Cell Genet, 24: 102-114 (1979)
Rozen et al.,Ann. Hum. Genet, 44: 781-786 (1989)
Jones et al. Somat. Cell Genet. 7: 399-409 (1981)
Hori et al., Hum. Genet 85: 576-580 (1990)
Silverman et al., Genomics 15: 442-445 (1993)
McInnis et al. Genomics 16: 562-571 (1993)
Schild et al. Proc. Natl. Acad. Sci 87: 2916-2920 (1990)
Avrarmopoulos et al. Genomics 15: 98-102 (1993)
Goto et al. Neuromusc Disord. 3: 157-160 (1993)
Moscow et al.,Cancer Res. 55: 3790-3794 (1995)
Munke et al.Am J. Hum. Gen 42: 550-559 (1988)

Genes of Cobalamin Metabolism: Cobalamin metabolism is also complex [Benton and Rosenberg, In: *The Metabolic and Molecular Bases of Inherited Disease*, Disease, Scriver et al. (eds), New York: McGraw-Hill, 3129-3149 (1995)]. At least 15 gene loci (Table 4) have been identified as cobalamin-related. These contribute to the binding, transport, and metabolism of cobalamin, and its functions. A number of these have been cloned and localized to a chromosomal region (5). Cobalamin metabolism is closely intertwined with that of folate. For example, cobalamin is required for the activity of MTR, a folate-related enzyme. Decreased cobalamin can affect folate metabolism through the folate trap [Rosenblatt, In: *The Metabolic and Molecular Bases of Inherited Disease*, Scriver et al. (eds), New York: McGraw-Hill, pp. 3111-3128 (1995); Quadros et al., *Biochem. Biophys. Res. Commun.*, 222:149-154 (1996)].

TABLE 4
COBALAMIN-RELATED GENES/ENZYMES/TRANSPORTERS[a]

| Cobalamin-Related Genes/Enzymes/Tranporters[a] | SEQ ID NO: |
|---|---|
| (gastric) intrinsic factor, GIF, MIM-261000 (combined deficiency of GIF & R-binder, MIM 243320 intrinsic factor receptor, IFCR, MIM-261100 | 31 |
| transcobalamin I, TCI (an R-protein, plasma), MIM 189905 transcobalamin III, TCIII (an R-protein, plasma), MIM-none other R-proteins (R-binders, cobalophylins, haptocorrins), | 32 |

TABLE 4-continued

COBALAMIN-RELATED GENES/ENZYMES/TRANSPORTERS[a]

| Cobalamin-Related Genes/Enzymes/Tranporters[a] | SEQ ID NO: |
|---|---|
| MIM 193090 | |
| transcobalamin II, TCII MIM 275350 | 33 |
| transcobalamin II receptor, TCII receptor, MIM-none | |
| methylmalonyl Co-A mutase, MCM (MUT locus), MIM 251000 | 34 |
| cblF, lysosomal cbl efflux, MIM 277380 | |
| cblC, cytosolic cbl metabolism, MIM 277400 | |
| cblD, cytosolic cbl metabolism, MIM 277410 | |
| cblA, mitochondrial cbl reduction, (AdoCbl synthesis only), MIM 251100 | |
| cblB, cob(I)alamin adenosyltransferase, (AdoCbl synthesis only), MIM 251110 | |
| cblE, methyltransferase-associated cbl utilization, MIM 236270 | |
| cblG, methyltransferase-associated cbl utilization, MIM 250940 | |

[a]listed with alternate names, abbreviations, and MIM numbers

TABLE 5

LOCALIZED GENE LOCI RELATED TO COBALAMIN METABOLISM

| Gene/enzyme/ transport protein | Location | References |
|---|---|---|
| MCM (MUT locus) | 6p21.2-p21.1 | Qureshi et al. (1994) * |
| IF/GIF | 11q12-q13 | Hewit et al. (1991) * |
| TCI (an R-protein, plasma) | 11q11-q12.3 | Johnston et al., (1992) |
| | | Sigal et al., (1987), * |
| TCII | 22q11.2-q13 | |
| | 22q12/13 border | Li et al., (1995) | notes:
MCM = methymalonyl Co-A mutase;
IF/GIF = (gastric) intrinsic factor;
TCI = transcobalmin I;
TCII = transcobalamin II.
Location information from GDB (*), from MIM (**).
Qureshi et al., *Crit. Rev. Oncol. Hematol.* 17: 133-151 (1994)
Hewit et al., *Genomics* 10: 432-440 (1991)
Johnston et al., *Genomics* 12: 459-464 (1992)
Sigal et al., *N. Engl. J. Med.* 317: 1330-1332 (1987)
Li et al., *Biochem. Biophys. Res. Comm.* 208: 756-764 (1995)

Genes of Pyridoxine Metabolism: Pyridoxine metabolism is also complex with three dietary forms convertible to pyridoxal phosphate [Whyte et al., *Hypophosphatasia*, In: The Metabolic and Molecular Bases of Inherited Disease, Scriver et al. (eds), New York: McGraw-Hill pp. 4095-4111 (1995)] and many pyridoxine-related and pyridoxine-dependent enzymes including decarboxylases and all aminotranferases (Table 6). A number of pyridoxine-related enzymes have been cloned and localized to a chromosomal region (Table 7). Pyridoxine metabolism is related to folate metabolism, especially 1-carbon transfer reactions: both serine hydroxymethyltransferases and the P-protein (glycine decarboxylase) of the glycine breakdown system are pyridoxine-dependent.

TABLE 6

SOME PYRIDOXINE-RELATED GENES/ENZYMES/[a]

| | |
|---|---|
| 1. cystathionine beta-synthase, CBS, | MIM 236200 |
| 2. gamma-cystathionase, (L-cystathionine cysteine-lyase, deaminating), LCCL | MIM 219500 |
| 3. glycine cleavage system (GCS): glycine decarboxylase (P-protein) | |
| 4. serine hydroxymethyltransferase 1, SHMT1, | MIM 182144 |
| 5. serine hydroxymethyltransferase 2, SHMT2, | MIM 138450 |
| 6. kynureninase | MIM 278600 |
| 7. all aminotransferases, (e.g. ornithine-gamma-aminotranferases, OAT,) | MIM 258870 |
| 8. decarboxylases, e.g. glutamic acid decarboxylases, GAD1, GAD2, | MIM 266100 |
| 9. pyridoxamine(pyridoxine)-5'-phosphate oxidase | MIM 603287 |

[a]listed with alternate names, abbreviations, and MIM numbers.

TABLE 7

SOME LOCALIZED GENE LOCI RELATED TO PYRIDOXINE METABOLISM

| Gene/enzyme | Location | References |
|---|---|---|
| 1. GAD2 | 2q31, | Bu et al., 1992) |
| 2. GCS P-protein | 9p13 | Hamosh et al.1995) |
| 3. GAD1 | 10p11.23 | Bu et al.1992) |
| 4. OAT | 10q26 | ** |
| 5. SHMT2 | 12q12-14 | Garrow et al., 1993; Law and Kao, 1979 |
| 6. LCCL | 16pter-qter | *, ** |
| 7. SHMT1 | 17p11.2 | Garrow et al.1993 * ** |
| 8. CBS | 21q22.3 | Munke et al.1988 |
| 9. PNPO (PPO) | | Ngo et al. 1998 |

[a]listed with alternate names, abbreviations, and MIM numbers.
Location information from GDB (*), from MIM (**).
notes:
GAD2 = glutamic acid decarboxylase 2, 67 kDa.
GCS = glycine cleaving system,
P-protein = glycine decarboxylase subunit.
GAD1 = glutamic acid decarboxylase 1, 65 kDa.
OAT = ornithine-gamma-aminotranferases.
SHMT2 = serine hydroxymethyltransferase 2, mitochondrial.
LCCL = gamma-cystathionase (L-cystathionine cysteine-lyase (deaminating).
SHMT1 = serine hydroxymethyltransferase 1, soluble.
CBS = cystathionine beta-synthase.
PNPO = pyridoxamine (pyridoxine)-5'-phosphate oxidase

REFERENCES

Bu et al., *Proc. Nat. Acad. Sci.*, 89:2115 (1992).
Hamosh et al., In: "The Metabolic and Molecular Bases of Inherited Disease", Scriver et al. (eds), New York: McGraw-Hill pp. 1337-1348 (1995).
Garrow et al. *J. Biol. Chem.* 268:11910-11916 (1993).
Law and Kao, *Cytogenet Cell Genet,* 24: 102-114 (1979).
Munke et al. *Am J. Hum. Gen.* 42:550-559 (1988).
Ngo et al. *Biochemistry* 37:7741-7748 (1998).

Relevance of Folate, Cobalamine, And Pyridoxine to Schizophrenia: There is considerable evidence that schizophrenia results, at least in part, from damage to brain development in utero that becomes symptomatic in late adolescence or early adulthood. The etiology of schizophrenia has both genetic and environmental components. Because folate, cobalamin, and pyridoxine are all ingested and metabolized, they could potentially be both environmental and genetic factors for schizophrenia. Folate, cobalamin, and pyridoxine are relevant to schizophrenia in important ways. First, all of them are required for cell division because of their role in nucleic acid synthesis [Rosenblatt, In: *The Metabolic and Molecular Bases of Inherited Disease*, Scriver et al. (eds) New York: McGraw-Hill, pp. 3111-3128 (1995); Benton and Rosenberg, In: *The Metabolic and Molecular Bases of Inherited Disease*, Scriver et al. (eds)., New York: McGraw-Hill, 3129-3149 (1995)]. The developmental brain insult implicated in schizophrenia [Akbarian et al., *Arch. Gen. Psychiatry,* 50:169-177 (1993); Akbarian et al., *Arch. Gen. Psychia-*

*try,* 50:178-187 (1993)] is an abnormality of neurogenesis and neuronal migration, which are midtrimester events requiring cell division. Thus folate, cobalamin, and pyridoxine deficiencies could result in the widespread decreased grey matter volume observed in schizophrenia.

Individuals that become schizophrenic later in life are more likely to be born during the winter and early spring [Boyd et al., *Schizophr. Bull.,* 12:173-186 (1986); Kendell and Adams, *Br. J. Psychiatry,* 158:758-763 (1991); O'Callaghan et al., *Br. J. Psychiatry,* 158:764-769 (1991)]; this corresponds to midtrimester in late fall & winter. Many folate- and pyridoxine-containing foods, e.g. dark green leafy vegetables, are less readily available in late fall & winter in northern climates. Seasonality was found to be a major determinant of micronutrient status including folate status in a population of pregnant and lactating women in The Gambia where folate deficiency was widespread [Bates et al. Eur. J. Clin. Nutr. 48:660-668 (1994)]. Dietary cobalamin comes from animal foods, e.g. meat, dairy products, and fish, and prolonged dietary insufficiency is required to produce cobalamin deficiency unless a person is a strict vegetarian or already has subclinical deficiency [Sanders and Reddy, *Am. J. Clin. Nutr.,* 59:1176S-1181S (1994)]. In fact, a significant fraction of the population already has subclinical deficiency for folate [Lewis et al., *Ann. NY Acad. Sci.,* 678:360-362 (1993)] and for [Carmel et al., *Arch. Intern. Med.,* 147:1995-1996 (1987); Pennypacker et al., *J. Am. Geriatr. Soc.,* 40:1197-1204 (1992); Naurath et al., *Lancet.,* 346:85-89 (1995); Allen et al., *Am. J. Clin. Nutr.,* 62:1013-1019 (1995); Black et al., *J. Nutr.,* 124:1179-1188 (1994)]. Also, the dietary folate requirement increases during pregnancy [Scholl et al., *Am. J. clin. Nutr.,* 63:520-525 (1996); McPartlin et al., *Lancet.,* 341:148-149 (1993)] and most women become folate deficient during late pregnancy [Giles, *J. Clin. Pathol.,* 19:1-11 (1966)]. Cobalamin deficiency is also common during pregnancy [Gadowsky et al., *J. Adolesc. Health,* 16:465-474 (1995)] although subnormal levels of vitamin B12 during pregnancy must be interpreted with caution [Metz et al., *Am. J. Hemetol.,* 48:251-255 (1995)]. An increase in schizophrenia births has also been noticed after winter famine [Susser and Lin, *Arch. Gen. Psychiatry,* 49:983-988 (1992)]; Susser et al., *Arch. Gen. Psychiatry,* 53:25-31 (1996)], a time when severe dietary deficiency of both folate and cobalamin is more likely. A temporary increase in the incidence of neural tube defects was reported in Jamaica 11-18 months following Hurricane Gilbert and was found to be associated with decreased dietary folate [Duff and Cooper, *Am J. Pub.Health* 84:473-476 (1994)].

Schizophrenia is also associated with obstetrical complications, e.g. low birth weight and prematurity [Lewis and Murray, *J. Psychiatr. Res.,* 21:413-421 (1987)]. Low birthweight and prematurity have also been associated with dietary folate deficiency during pregnancy Scholl et al., *Am. J. clin. Nutr.,* 63:520-525 (1996). Hyperhomocysteinemia is a risk factor for unexplained recurrent early pregnancy loss [Wouters et al., *Fertil. Steril.,* 60:820-825 (1993)] and for abruptio placentae [Goddijn-Wesel et al., *Eur. J. Obstet. Gynecol. Reprod. Biol.,* 66:23-29 (1996)]. Hyperhomocysteinemia may be related to defects in folate-, cobalamin-, or pyridoxine-dependent reactions [Naurath et al., *Lancet.,* 346: 85-89 (1995)]. Interestingly, stillbirths and schizophrenia share a similar seasonality of birth excess [Torrey et al., *Schizophr. Bull,* 19:557-562 (1993)]. Also $N_2O$, an anaesthetic gas that inhibits MTR, a cobalamin-requiring enzyme of folate metabolism, is a reproductive toxin for both men and women [Louis-Ferdinand, *Adverse Drug React. Toxicol Rev.,* 13:193-206 (1994)]. Methotrexate, an inhibitor of dihydrofolate reductase (DHFR), induces abortion.

Dietary folate deficiency and low plasma folate are common in inner city urban populations [Scholl et al., *Am. J. clin. Nutr.,* 63:520-525 (1996)]. Likewise, schizophrenia has been reported to be more common in inner city urban populations [Fuller and Bowler, *Schizophr. Bull.,* 16:591-604 (1990)]. Also, both low folate intake [Schorah and Wild, *Lancet.,* 341:1417 (1993)] and schizophrenia [Dohrenwned et al., *Science,* 255:946-952 (1992)] are correlated with lower socioeconomic status.

Immune function is impaired in folate deficiency [LeLeiko and Chao, In: *Rudolph's Pediatrics,* 20th ed., Stamford, Conn.: Appleton & Lange, pp. 1001-1010 (1996)], in cobalamin deficiency [Hitzig et al., *Ciba. Found. Symp.,* 68:77-91 (1978)] and in pyridoxine deficiency [Trakatellis et al. *Postgrad Med. J.* 73:617-622 (1997)] and deficient individuals are more susceptible to infection. Methotrexate, an inhibitor of dihydrofolate reductase, inhibits immune function [Hughes, In: *Rudolph's Pediatrics,* 20th ed., Stamford, Conn.: Appletone and Lange, pp. 517-519 (1997)]. And, as mentioned, dietary folate and cobalamin requirements increase during pregnancy [Scholl et al., *Am. J. clin. Nutr.,* 63:520-525 (1996); McPartlin et al., *Lancet.,* 341:148-149 (1993)]. This is relevant because the season-of-birth effect just mentioned in connection with dietary folate, or cobalamin deficiency has also been explained by in utero infectious illness, the "viral theory" of schizophrenia. Individuals born following winters with severe influenza epidemics are more likely to develop schizophrenia [Adams et al., *Br. J. Psychiatry,* 163:522-534 (1993)] though not all studies find this effect. Although it has not been demonstrated that either the schizophrenia fetus or the pregnant mother actually developed influenza, the histologic pattern in schizophrenia of a neuronal migration abnormality during brain development has been seen as compatible with a fetal viral infection [Kovelman and Scheibel, *Biol. Psychiatry,* 19:1601-1621 (1984); Bogerts et al., *Arch. Gen. Psychiatry,* 42:784-791 (1985); Akbarian et al., *Arch. Gen. Psychiatry,* 50:169-177 (1993); Akbarian et al., *Arch. Gen. Psychiatry,* 50:178-187 (1993)]. Thus folate or cobalamin, deficiency during pregnancy could result in greater susceptibility to viral infection affecting mother, fetus, or both. The infectious agent could be influenza itself. Alternatively, a severe influenza epidemic could be a "marker" of a severe winter, and infection by another agent could cause the brain damage. In this way, folate or cobalamin deficiency could cause the season-of-birth effect either through the mechanism of dietary deficiency alone, through maternal immune deficiency and infection, or both.

Methotrexate, a DHFR inhibitor, is also an important therapeutic agent for rheumatoid arthritis. Rheumatoid arthritis has repeatedly been found to have a decreased frequency in schizophrenics, a puzzling finding that remains unexplained [Eaton et al., *Schizophr. Res.,* 6:181-192 (1992)].

The developmental model of schizophrenia postulates that brain damage sustained in the second trimester of fetal life results in schizophrenia later in development [Brixey et al., *J. Clin. Psychol.,* 49:447-456 (1993)]. Both folate and cobalamin are already known to contribute to a first trimester fetal nervous system malformation, spina bifida cystica [Kirke et al., *Q. J. Med.,* 86:703-708 (1993); Gordon, *Brain Dev.,* 17:307-311 (1995)], and possibly other birth defects [Shaw et al., *Lancet.,* 346:393-396 (1995); Czeizel, *Lancet.,* 345:932 (1995)]. Some studies [Whitehead et al., *Q. J. Med.,* 88:763-766 (1995); van der Put et al., *Lancet.,* 346:1070-1071 (1995); Ou et al., *Am. J. Med. Genet.,* 63:610-614 (1996); Chatkupt et al., *Am. Acad. Neurol. Works in Progres,* WIP4:

(1996)] suggest that a genetic susceptibility factor for spina bifida is a common allele of the folate gene, MTHFR, the nucleotide 677C->T transition converting an alanine residue to valine resulting in a heat-labile enzyme protein. Homozygotes for this allele, about 10% of the normal population, have lower erythrocyte folate and plasma folate during pregnancy [Molloy et al., Lancet., 349:1591-1593 (1997)]. Homozygotes for this allele also develop moderately elevated blood homocysteine [van der Put et al., Lancet., 346:1070-1071 (1995); Frosst et al., Nature Genet., 10:111-113 (1995)] in the presence of dietary folate deficiency. Moderate hyperhomocysteinemia is toxic to adults [Fermo et al., Ann. Intern. Med., 123:747-753 (1995)], and toxic to the fetus in early gestation [Wouters et al., Fertil. Steril., 60:820-825 (1993)], and possibly teratogenic in the first trimester causing neural tube defects [Whitehead et al., Q. J. Med., 88:763-766 (1995); van der Put et al., Lancet., 346:1070-1071 (1995); Ou et al., Am. J. Med. Genet., 63:610-614 (1996). Thus, the MTHFR heat-labile mutation, in the presence of decreased dietary folate in midtrimester, could be teratogenic both through hyperhomocysteinemia and also through folate deficiency causing the developmental brain damage hypothesized in the developmental model of schizophrenia [Brixey et al., J. Clin. Psychol, 49:447-456 (1993)]. A second common polymorphism of MTHFR, the nt1298 A->C mutation could also be a genetic risk factor for spina bifida [van der Put et al., Lancet., 346:1070-1071 (1995)].

Schizophrenia is a common disorder, affecting 1% or more of the population [Karno et al., In: Comprehensive Textbook of Psychiatry/VI, 6th ed., Baltimore: Williams & Wilkins, pp. 902-910 (1995)]. Thus, if a significant proportion of schizophrenia shares a common etiology, both the genetic susceptibility factors and the environmental factors must be common in the population. As mentioned earlier, a significant fraction of the population is already sub-clinically deficient for folate and for cobalamin; also, pregnancy may increase this fraction since dietary folate and cobalamin requirements increase during that time. Several functional polymorphic alleles of folate and cobalamin genes are also common in the population including the MTHFR mutations just mentioned and polymorphisms of thymidylate synthase [Horie et al., Cell Struct. Funct., 20:191-197 (1995)], transcobalamin II [Li et al., Biochim. Biophys. Acta., 1219:515-520 (1994)], and folate-binding proteins [Li et al., 1994, supra; Shen et al., Biochem., 33:1209-1215 (1994)]. Metabolic indicators of folate or cobalamin deficiency, e.g. hyperhomocysteinemia and hypermethylmalonicacidemia, are also common in the population [Naurath et al., Lancet., 346:85-89 (1995)]. Thus there exists a statistical basis for the hypothesis that schizophrenia is a birth defect resulting from the action during gestation of genetic risk factors and environmental factors related to folate and/or cobalamin that lead to the generation of risk factors. Such factors are sufficiently common that at least in principle all cases of schizophrenia could result from this mechanism.

Finally, folate, cobalamin, and pyridoxine are relevant for schizophrenia because of findings in patients. Severe genetic deficiency of MTHFR may cause a "schizophrenia" phenotype [Freeman et al., N. Engl. J. Med., 292:491-496 (1975); Regland et al., J. Neural Transm. Gen. Sect., 98:143-152 (1994)]. Genetic deficiency of other folate and cobalamin enzymes has been reported to cause nervous system disease, psychiatric disease, or schizophrenia-like illness [Mudd et al., In: The Metabolic and Molecular Bases of Inherited Disease, Scriver et al. (eds), New York: McGraw-Hill pp. 1279-1327 (1995); Hitzig et al., Ciba. Found. Symp., 68:77-91 (1978); Cooper and Rosenblatt, Annu. Rev. Nutr., 7:291-320 (1987); Shevall and Rosenblatt, Can. J Neurol. Sci., 19:472-486 (1992); Hall, Br. J. Haematol., 80:117-120 (1992)]. Likewise, dietary deficiencies of folate or cobalamin may have similar effects [Cooper and Rosenblatt, Annu. Rev. Nutr., 7:291-320 (1987); Shevall and Rosenblatt, Can. J Neurol. Sci., 19:472-486 (1992)]. Methylfolate therapy reportedly improved the clinical status of schizophrenics with borderline or definite folate deficiency [Godfrey et al., Lancet., 2:392-395 (1990); Procter, Br. J. Psychiatry, 159:271-272 (1991)] although the improvement claimed was small and the finding controversial. Folate deficiency has been associated with disturbances in mood [Shulman, In: Folic Acid in Neurology, Psychiatry, and Internal Medicine, New York: Raven Pr., 463-474 (1979)], and it has been suggested that the most common neuropsychiatric system abnormality in severe folate deficiency is depression [Reynolds et al., Lancet., ii:196-198 (1984)]. Methyltetrahydrofolate reportedly improved symptoms of depression in an open trial in elderly depressed patients [Guaraldi et al. Ann. Clin.Psychiatry 5:101-105 (1993)]. Schizophrenics are reported to have an 80% excess mortality from cardiovascular disease [Gottesman, Schizophrenia Genesis, Schizophrenia Genesis—The Origins of Madness, W.H. Freeman & Co. N.Y.(1991)]; hyperhomocysteinemia, dietary folate deficiency and the MTHFR 677C->T mutation have been implicated in cardiovascular disease in some studies [Morita et al., Circulation, 95:2032-2036 (1997)] but not others (Anderson et al., J. Am. Coll. Cardiol. 30:1206-1211 (1997)]. Also, kynureninase, an important enzyme of tryptophan metabolism, affecting niacin metabolism and serotonin synthesis, is pyridoxine-dependent. Niacin deficiency (pellagra) can cause mental changes including psychosis and hallucinations [Wilson, Vitamin deficiency and excess, pp. 472-480. In: Harrison's Principles of Internal Medicine, (Scriber et al. e's.) McGraw-Hill, Inc., N.Y. (1994)]. Also, clozapine, resperidone, and olanzapine are thought to exert their antipsychotic effect in schizophrenia in part through serotonin receptor antagonism.

Gene Localization Studies in Schizophrenia and Folate/Cobalamine/Pyridoxine Genes: If folate, cobalamin, or pyridoxine genes are susceptibility factors for schizophrenia, it is possible that gene localization studies have already identified candidate chromosome regions that contain such a gene (Tables 3, 5, and 7). For three folate or cobalamin genes, DHFR, TCNII and TYMS, there is excellent concordance with schizophrenia gene localization studies.

On chromosome 5, DHFR has been located at 5q11.2-13.2. A schizophrenia translocation [t(1;5)(1q32.3;5q11.2-13.3)] was reported [McGillivray et al., Am. J. Med. Genet., 35:10-13 (1990); Bassett, Br. J. Psychiatry, 161:323-334 (1992)] affecting 5q11.2-5q13.3. A proband and uncle, both with schizophrenia and eye-tracking abnormalities, had partial trisomy for 5q11.2-5q13.3; the third copy was inserted at 1q32.3 giving a derivative chromosome, der(1)inv ins(1;5)(q32.2;q13.3q11.2). The proband's mother had a balanced translocation but was phenotypically normal without schizophrenia or eye-tracking abnormalities. She had the derivative chromosome 1 with extra material from chromosome 5 inserted but a corresponding deletion in one of her chromosomes 5. She thus had only two copies of 5q11.2-5q13.3. Further studies [Gilliam et al., Genomics, 5:940-944 (1989)] showed that the DHFR gene is located within this deleted region, 5q11.2-13.3. Another schizophrenia chromosome abnormality, inv5(p13;q13), has been reported [Bassett, Br. J. Psychiatry, 161:323-334 (1992)] affecting 5q13.

On chromosome 5, two-point lod scores of 4.64 and 2.29 were found [Sherrington et al., Nature, 336:164-167 (1988)] for the polymorphic markers D5S76 and D5S39 respectively in the region of the chromosome abnormality just discussed [McGillivray et al., *Am. J. Med. Genet.*, 35:10-13 (1990); Bassett, *Br. J. Psychiatry*, 161:323-334 (1992)] affecting 5q11.2-13.3. Two other linkage studies found small positive lod scores in this region [Coon et al., *Biol. Psychiatry*, 34:277-289 (1993); Kendler and Diehl, *Schizophr. Bull.*, 19:261-285 (1993)], but numerous other studies excluded this region under the assumptions and models used [Kendler and Diehl, *Schizophr. Bull.*, 19:261-285 (1993)].

On chromosome 18, TYMS has been located at 18p11.32-p11.22. A ring chromosome with deletion of 18pter-p 11,18q23-qter [Bassett, *Br. J. Psychiatry*, 161:323-334 (1992)] was reported in a kindred with schizophrenia and bipolar illness [Bassett, *Br. J. Psychiatry*, 161:323-334 (1992)]. Deletion of a segment of 18p was reported in a schizophrenia chromosome [Bassett, *Br. J. Psychiatry*, 161: 323-334 (1992)].

On chromosome 22, TCNII has been located at 22q11.2-q13, possibly at the 22q12/13 border. High lod scores have consistently been obtained in the region of TCNII: IL2RB, in 22q12-q13.1 gave a lod score [Pulver et al., *Am. J. Med. Genet.*, 54:3-43 (1994)] of 2.82. Other markers over a broad region of 22q have given suggestive lod scores. D22S278, in 22q12, gave a lod score [Vallada et al., *Am. J. Med. Genet.*, 60:139-146 (1995)] of 1.51. CRYB2, in 22q11.2-q12.1, gave a lod score [Lasseter et al., *Am. J. Med. Genet.*, 60:172-173 (1995)] of 1.71. D22S 10, in 22q11.1-q11.2, gave a lod score [Coon et al., *Biol. Psychiatry*, 34:277-289 (1993)] of 0.79. Highly significant p-values for non-parametric analyses have also been obtained: D22S278, in 22q12, for example gave p=0.001 [Gill et al., *Am. J. Med. Genet.*, 67:40-45 (1996)].

The deletions of velocardiofacial (VCF) syndrome and related disorders (DiGeorge syndrome (DGS) and CATCH22) are located [Lindsay et al., *Genomics*, 32:104-112 (1996)] at 22q11.2. A psychotic disorder develops in about 10% of patients with VCF syndrome [Chow et al., *Am. J. Med. Genet.*, 54:107-112 (1994)]. TCNII is not known to be located at or within these deletions. VCF and related disorders are relatively uncommon compared to schizophrenia; only 2 of 100 randomly selected patients (92 schizophrenics, 5 with schizoaffective disorder, and 3 with schizophreniform disorder) in the Maryland Epidemiological Sample were found [Lindsay et al., *Am. J. Hum. Genet.*, 56:1502-1503 (1995)] to have VCF-related deletions (and later VCF syndrome) on 22q11.2. Consequently, it is not clear whether schizophrenia linkage studies are detecting a haplotype related to a VCS locus or some other locus in this region, such as TCNII.

For some other folate, cobalamin, or pyridoxine relevant genes, physical or genetic studies of schizophrenia have identified chromosomal regions near the gene.

Discussion

The folate-cobalamin hypothesis for schizophrenia is attractive because it suggests that a single mechanism of genetic and environmental factors may play a major role in the etiology and pathogenesis of schizophrenia. The combined result of this mechanism is to damage fetal development, especially brain development by inhibiting nucleic acid synthesis, by affecting gene methylations, by increasing susceptibility to infection, and/or by producing teratogens.

This mechanism addresses several puzzling features of schizophrenia such as the season of birth effect, the association with famine and influenza epidemics, the negative association with rheumatoid arthritis, the associations with obstetrical abnormalities, social class, and urban environment. The mechanism also suggests approaches to diagnostic testing, to prevention, and to improved therapy.

It is not excluded that such a mechanism could also apply to a number of common human developmental disorders that have been shown to have a genetic component to their etiology but whose mode of inheritance has been difficult to determine and for which linkage studies have met with unexpected difficulties or have achieved limited success. These developmental disorders include Tourette's syndrome & related disorders (e.g. obsessive-compulsive disorder and chronic multiple tics syndrome) [Pauls, *Adv Neurol*, 58:151-157 (1992); McMahon et al., *Adv Neurol*, 58:159-165 (1992); Heutink et al., *Am J Hum Genet*, 57:465-473 (1995); Grice et al., *Am J Hum Genet*, 59:644-652 (1996)], learning disorders, including dyslexia [Lewis, et al., *Behav Genet*, 23:291-297 (1993); Pennington, *J Child Neurol* 10 Suppl, 1:S69-S77 (1995)], conduct disorder [Lombroso et al., *J. Am. Acad. Child Adolesc. Psychiatry*, 33:921-938 (1994)], attention-deficit hyperactivity disorder [Lombroso et al., 1994, *J. Am. Acad. Child Adolesc. Psychiatry*, 33:921-938 (1994)], bipolar illness [Baron, *Acta. Psychiatr. Scand.*, 92:81-86 (1995); Benjamin and Gershon, *Biol. Psychiatry*, 40:313-316 (1996); Risch and Botstein, *Nature Genet.*, 12:351-353 (1996); Jamison and McInnis, *Nature Med.*, 2:521-522 (1996); Morell, *Science*, 272:31-32 (1996)], autism [Lombroso et al., 1994, *J. Am. Acad. Child Adolesc. Psychiatry*, 33:921-938 (1994)], and obsessive-compulsive disorder in adults [Lombroso et al., 1994, *J. Am. Acad. Child Adolesc. Psychiatry*, 33:921-938 (1994)]. Some of these disorders have been shown to be associated with schizophrenia.

The present invention may be better understood by reference to the following non-limiting Examples, which are provided as exemplary of the invention. The following Examples are presented in order to more fully illustrate one embodiment of the invention. They should in no way be construed, however, as limiting the broad scope of the invention.

EXAMPLE 1

Diagnosing Schizophrenia

Structure of Datafiles

Data are arranged in a file suitable for input into a binary logistic regression program (Table 8). A model is created consisting of those explanatory variables actually available from the specific patient-to-be-diagnosed and family members participating in the testing. This new combined data set (reference data set+data from patient-to-be-diagnosed with participating family members) is analyzed by binary logistic regression for the model chosen giving the predicted probability that a proband is affected with schizophrenia for all of the probands including the patient-to-be-diagnosed.

The model can be modified if required. The goodness of fit for the patient-to-be-diagnosed is checked. The predicted probability that the patient-to-be-diagnosed has schizophrenia is compared with a classification table generated from the model used to determine likelihood of false positives and false negatives. The predicted probability that the patient-to-be-diagnosed is affected with schizophrenia, with likelihood of false positive or false negative result, is returned to the clinician.

TABLE 8

A HYPOTHETICAL PARTIAL REFERENCE DATA SET OF GENETIC
EXPLANATORY VARIABLES TO ILLUSTRATE DATA STRUCTURE

| ID | resp | P111 | P112 | P211 | P212 | M111 | M112 | M311 | F511 | S2-411 | CA1-111 |
|---|---|---|---|---|---|---|---|---|---|---|---|
| 1 | 1 | 1 | 0 | 1 | 1 | 1 | 1 | 0 | 0 | 1 | 1 |
| 2 | 1 | 1 | 0 | 0 | 0 | 0 | 0 | 0 | 1 | 0 | 0 |
| 3 | 1 | 1 | 1 | 1 | 0 | 1 | 0 | 0 | 1 | 1 | 1 |
| 4 | 1 | 0 | 0 | 0 | 0 | 0 | 0 | 1 | 0 | 0 | 0 |
| 5 | 1 | 0 | 0 | 1 | 1 | 1 | 1 | 0 | 0 | 0 | 1 |
| 6 | 0 | 1 | 0 | 0 | 0 | 0 | 0 | 0 | 0 | 0 | 0 |
| 7 | 0 | 0 | 0 | 0 | 0 | 0 | 0 | 1 | 0 | 0 | 0 |
| 8 | 0 | 0 | 0 | 1 | 0 | 0 | 0 | 0 | 1 | 1 | 0 |
| 9 | 0 | 1 | 0 | 0 | 0 | 1 | 0 | 0 | 0 | 1 | 1 |
| 10 | 0 | 0 | 0 | 0 | 0 | 1 | 0 | 0 | 0 | 1 | 0 |
| 11 | ... | | | | | | | | | | |
| n | | | | | | | | | | | |

For each proband (Table 8), the record contains several variables:
- identification number (ID) of the proband.
- a binary response variable (resp) for affection status of the proband: response=1, if the proband is affected with schizophrenia; response=0 if proband is unaffected (i.e. a control individual). The proband is not necessarily one of the individuals for whom genotype data (explanatory variables) are available. The patient-to-be-diagnosed is assigned response=0 when added to the reference data set.
- a set of explanatory variables: i.e. sets of genotypes of mutations found in the schizophrenia patients and family members and controls and family members. The schizophrenia patients and the control individuals are probands (P) as is the patient-to-be-diagnosed. Unaffected family members are the proband's mother (M), father (F), sib(s) (S1, S2, etc.), child(ren) (C1, C2, etc.) or other relatives. Data for affected family members, e.g. the proband's mother (MA), father (FA), sibs (SA1, SA2, etc.), children (CA1, CA2, etc.), or other relatives, are entered as separate explanatory variables.

Genetic explanatory variables: Each individual has 0, 1, or 2 copies of any given mutation allele at a given locus. Thus a genotype at each locus contributes two independent explanatory variables. Most of the affected family members will be relatives of schizophrenia probands, but occasionally a relative of an unaffected proband will turn out to be affected with schizophrenia.

Mutations are tabulated as explanatory variables: (see Table 8):
(i) by the proband or relative in whom they occur, (e.g. P, M, F, S2, C1, MA, FA, SA1, CA1, other);
(ii) by the specific folate, cobalamin, or pyridoxine gene locus in which they occur (e.g. 1=DHFR locus, 2=MTHFR locus, 3=TCN2 locus, 4=MTR locus, 5=CBS locus, etc.);
(iii) by the specific mutation within a locus (e.g., 1=the first-designated mutation within a locus, 2=the second-designated mutation within a locus, etc.); and
(iv) by whether the individual has a single or double dose of the mutation. Thus an explanatory variable P321 records whether the proband has a single dose of the second-designated mutation of the third-designated locus, i.e. TCN2. A variable M312 records whether the proband's mother has a double dose of the first-designated TCN2 mutation studied.

In the present hypothetical reference dataset illustrated of genetic explanatory variables (Table 8), partial genotype data for probands, mothers, fathers, sibs and children are given for five gene loci. Not all of the possible explanatory variables are shown. Probands 1-5 are unrelated individuals with the definite clinical diagnosis of schizophrenia; probands 6-10 are unrelated unaffected (control) individuals. Probands 1, 2, 3, 6 and 9 all have a single copy of the first-designated DHFR mutation; proband 3 also has a second copy of that mutation. Probands 1, 3, 5 and 8 all have a single copy of the first-designated mutation at the MTHFR locus; probands 1 and 5 also have a second copy of that mutation. Mothers of probands 1, 3, 5, 9 and 10 all have a single copy of the first-designated DHFR mutation; mothers of probands 1 and 5 also have a second copy of this mutation. Mothers of probands 4 and 7 each have a single copy of the first-designated mutation of TCN2; data for a double dose are not shown. The fathers of probands 2, 3, and 8 each have a single copy of the first designated mutation of CBS; data for a double dose are not shown. The second (unaffected) sibs of probands 1, 3, 8, 9, and 10 each have a single copy of the first-designated mutation of MTR; data for a double dose are not shown. The first affected children of probands 1, 3, 5, and 9 each have a single copy of the first-designated mutation of DHFR. Other susceptibility loci and mutations can be incorporated in Table 8 in the same fashion e.g., cytokine gene mutations or polymorphisms, or major histocompatibility complex (MHC) mutations or polymorphisms.

Environmental explanatory variables: If only genetic explanatory variables (genotype data) are used, the maximum predicted probability that the proband is affected with schizophrenia is expected to be approximately about 0.5 in most populations. When environmental risk factors are included as explanatory variables, the maximum predicted probability that the proband is affected with schizophrenia may approach 1.0. Examples of environmental risk factors for a schizophrenia patient include:
(1) the proband's dietary folate/cobalamin/pyridoxine intake.
(2) the proband's circulating levels of folate/cobalamin/pyridoxine.
(3) the proband's circulating levels of homocysteine, methylmalonic acid, or cystathionine. Elevated levels are indicators of subtle folate/cobalamin deficiency.
(4) the proband's mother's dietary folate/cobalamin/pyridoxine intake at the time of patient diagnosis, during a pregnancy, or during the pregnancy that produced the proband.
(5) the proband's mother's circulating levels of homocysteine, methylmalonic acid, or cystathionine at the time of patient diagnosis, during a pregnancy, or during the pregnancy that produced the proband.

(6) dietary or circulating folate/cobalamin/pyridoxine or circulating levels of homocysteine, methylmalonic acid, or cystathionine for other family members.

(7) epidemiological factors related to the proband's gestation and birth, e.g. low birth weight or preterm birth, maternal infection, maternal smoking (associated with low plasma folate), season of birth (late winter or spring births are more common in schizophrenia), etc.

Method of Data Analysis

The method exemplified herein is based upon the published guide for the SAS system, but other software can be used. The dataset is analyzed using binary logistic regression to model the response probability, $p_i$, that the ith proband's affection status is 1, i.e. the probability that the ith proband has schizophrenia, given the vector of explanatory variables, $x_i$. That is:

$$p_i = \text{Prob}(y_i = 1 | x_i).$$

To do this the logit transformation of $p^i$ is modeled as a linear function of the explanatory variables in the vector, $x_i$:

$$\text{logit}(p_i) = \log(p_i/[1-p_i]) = \text{alpha} + \text{beta}'x_i$$

where: alpha is the intercept parameter and
beta is the vector of slope parameters.

In SAS, the "descending" option is used to model the probability that the response=1, as in the present analysis, rather than response=0.

Outputs of Binary Logistic Recession Analysis

After analysis of a dataset, the outputs obtained from SAS include:

(a) Estimates and standard errors of the parameters (alpha and beta). Using estimates of the intercept parameter (alpha) and the slope parameter (beta) for each environmental or genetic risk factor, the logistic regression equation for the dataset can be written.

(b) Significance tests of the parameters (e.g. Wald chi-square). From the corresponding p-values, the level of significance of each of the environmental or genetic risk factors is determined. A global significance test of the data with corresponding p-value is also determined.

(c) Odds ratios are given for the slope parameters of each environmental or genetic risk factor. Thus the amount contributed by each environmental or genetic risk factor to the risk of schizophrenia is determined.

(d) The confidence limits for regression parameters and odds ratios are determined.

(e) The predicted probabilities of the observations can be computed, i.e. the probability that each individual in the dataset has schizophrenia:
alpha~=estimate of the intercept parameter;
beta~=vector of the estimates of the slope parameters;
x=vector of the explanatory variables;
p~=predicted probabilities $$p\sim = \frac{1}{1+\exp(\text{alpha}\sim-\text{beta}\sim'x)}$$

(f) The model is modified by adding or removing variables until a model is found that best fits the data;

(g) The model is tested for goodness-of-fit. Also, the degree of influence of each specific observation is tested to detect extreme or ill-fitting observations. These may be examples of data entry errors or alternatively, observations that do not fit the present model for schizophrenia.

(h) The probability that a new individual (the patient-to-be-diagnosed) is schizophrenic is then calculated from the final, modified, best fitting regression equation based upon parameters derived from a corrected/modified data set. A simple method of doing this is to add the data for the patient-to-be-diagnosed to the reference data set, a large group of well-studied schizophrenia probands, schizophrenia family members, control probands and control family members for whom data are available for many explanatory variables. A model is created consisting of those informative explanatory variables actually available from the specific patient-to-be-diagnosed and family members participating in the testing. This new combined data set (reference data set+data from patient-to-be-diagnosed with participating family members) is analyzed by binary logistic regression for the model chosen giving the predicted probability that a proband is affected with schizophrenia for all of the probands including the patient-to-be-diagnosed.

(i) A classification table is produced from the data set by the "jack knifing" procedure or an approximation to it. This procedure classifies each observation as an event or non-event based on the model that omits the observation being classified. A classification table sorts observations into percent correct, percent false positives, and percent false negatives at various probability levels and computes sensitivity and specificity.

(j) The data set used for diagnostic testing is constantly being updated and the regression equation corrected. For example, stratification by geographic residence or geographic origin of ancestors must be considered for some environmental or genetic risk factor.

For example, in Table 9, entries 34-43 are shown for the data file containing genotypes of 38 schizophrenic probands plus 211 control probands; the first 38 are the affected probands. For individual 302088, the proband is affected ("1"); there is a single dose ("1") of the DHFR mutation but not a double dose ("0") and a single dose ("1") of the MTHFR mutation but not a double dose ("0"). The number 302088 identifies the individual whose genotypes are listed; the proband, in this case, is the same individual.

TABLE 9

SAS DATAFILE FOR SCHIZOPHRENIA PATIENTS AND CONTROLS

...

| 34 | 302086 | 1 | 1 | 0 | 1 | 1 |
| 35 | 302088 | 1 | 1 | 0 | 1 | 0 |
| 36 | 302110 | 1 | 1 | 0 | 1 | 0 |
| 37 | 302111 | 1 | 1 | 0 | 0 | 0 |
| 38 | 302136 | 1 | 1 | 1 | 1 | 0 |
| 39 | 100001 | 0 | 1 | 0 | 0 | 0 |
| 40 | 100061 | 0 | 0 | 0 | 0 | 0 |
| 41 | 100064 | 0 | 1 | 0 | 1 | 0 |
| 42 | 100067 | 0 | 0 | 0 | 1 | 0 |
| 43 | 100073 | 0 | 1 | 0 | 0 | 0 |

...

In Table 10, entries 31-40 are shown for the data file containing genotypes of 35 mothers of schizophrenic probands plus (the same) 211 control probands. For individual 302083, the proband is affected ("1"); there is a single dose of the DHFR mutation ("1) but not a double dose ("0"); there is neither a single ("0") nor a double ("0") dose of the MTHFR mutation. The number 302083 identifies the individual whose genotypes are listed, a mother; the proband, in this case, is a different individual, her affected child.

TABLE 10

SAS DATAFILE FOR SCHIZOPHRENIA MOTHERS AND CONTROLS

| ... | | | | | | |
|---|---|---|---|---|---|---|
| 31 | 302083 | 1 | 1 | 0 | 0 | 0 |
| 32 | 302103 | 1 | 0 | 0 | 1 | 0 |
| 33 | 302104 | 1 | 0 | 0 | 1 | 0 |
| 34 | 302105 | 1 | 1 | 0 | 1 | 0 |
| 35 | 302120 | 1 | 0 | 0 | 0 | 0 |
| 36 | 100001 | 0 | 1 | 0 | 0 | 0 |
| 37 | 100061 | 0 | 0 | 0 | 0 | 0 |
| 38 | 100064 | 0 | 1 | 0 | 1 | 0 |
| 39 | 100067 | 0 | 0 | 0 | 1 | 0 |
| 40 | 100073 | 0 | 1 | 0 | 0 | 0 |
| ... | | | | | | |

In Table 11, entries 11-20 are shown for the data file containing genotypes of 15 fathers of schizophrenic probands plus (the same) 211 control probands. For individual 302084, the proband is affected ("1"); there is a single dose ("1") but not a double dose ("0") of the DHFR mutation; there is both a single ("1") and a double dose ("1") of the MTHFR mutation. The number 302084 identifies the individual whose genotypes are listed, a father; the proband, in this case, is a different individual, his affected child.

TABLE 11

SAS DATAFILE FOR SCHIZOPHRENIA FATHERS AND CONTROLS

| ... | | | | | | |
|---|---|---|---|---|---|---|
| 11 | 302102 | 1 | 0 | 0 | 0 | 0 |
| 12 | 302106 | 1 | 1 | 0 | 0 | 0 |
| 13 | 302115 | 1 | 1 | 0 | 0 | 0 |
| 14 | 302117 | 1 | 1 | 0 | 0 | 0 |
| 15 | 302084 | 1 | 1 | 0 | 1 | 1 |
| 16 | 100001 | 0 | 1 | 0 | 0 | 0 |
| 17 | 100061 | 0 | 0 | 0 | 0 | 0 |
| 18 | 100064 | 0 | 1 | 0 | 1 | 0 |
| 19 | 100067 | 0 | 0 | 0 | 1 | 0 |
| 20 | 100073 | 0 | 1 | 0 | 0 | 0 |
| ... | | | | | | |

In Table 12, entries 9-18 are shown for the data file containing genotypes of 13 unaffected sibs of schizophrenic probands plus (the same) 211 control probands. For individual 302089, the proband is affected ("1"); there is a single dose ("1") but not a double dose ("0") of the DHFR mutation; there is both a single ("1") and a double dose ("1") of the MTHFR mutation. The number 302089 identifies the individual whose genotypes are listed, an unaffected sib; the proband, in this case, is a different individual, the affected sib of individual 302089.

TABLE 12

SAS DATAFILE FOR SCHIZOPHRENIA SIBS AND CONTROLS

| ... | | | | | | |
|---|---|---|---|---|---|---|
| 09 | 302071 | 1 | 1 | 0 | 0 | 0 |
| 10 | 302073 | 1 | 0 | 0 | 1 | 0 |
| 11 | 302089 | 1 | 1 | 0 | 1 | 1 |
| 12 | 302118 | 1 | 1 | 0 | 0 | 0 |
| 13 | 302126 | 1 | 1 | 0 | 0 | 0 |
| 14 | 100001 | 0 | 1 | 0 | 0 | 0 |
| 15 | 100061 | 0 | 0 | 0 | 0 | 0 |
| 16 | 100064 | 0 | 1 | 0 | 1 | 0 |

TABLE 12-continued

SAS DATAFILE FOR SCHIZOPHRENIA SIBS AND CONTROLS

| 17 | 100067 | 0 | 0 | 0 | 1 | 0 |
|---|---|---|---|---|---|---|
| 18 | 100073 | 0 | 1 | 0 | 0 | 0 |
| ... | | | | | | |

In Tables 9-12 for individual 100061, the proband is unaffected ("0"); there is neither a single dose ("0") nor a double dose ("0") of the DHFR mutation; there is neither a single dose ("0") nor a double dose ("0") of the MTHFR mutation. Since the proband is unaffected, this is a control individual. The number 100061 identifies the individual whose genotypes are listed, as a control individual; the proband, in this case, is the same individual. The identical group of control individuals is used for all four comparisons.

EXAMPLE 2

Distribution of Folate Gene Polymorphism Genotypes Among Schizophrenics, Schizophrenia Parents, Schizophrenia Sibs, and Controls Summary The DNA polymorphism-Diet-Cofactor-Development hypothesis (DDCD hypothesis, described above) postulates that schizophrenia results in part from developmental brain damage sustained in utero from the aggregate effect of maternal defects of genes related to important cofactors, e.g. folate, cobalamin, pyridoxine, potentiated by a maternal dietary deficiency of these cofactors. The maternal damage to the fetus results in part from insufficiency of these cofactors themselves and in part from resulting effects such as immune deficiency and maternal teratogens, e.g. hyperhomocysteinemia. Genes from either parent acting in the fetus may modify these damaging effects as outlined in the gene-teratogen model (described above).

The hypothesis addresses all of the unusual biological and epidemiological features of schizophrenia: e.g. the decreased amount of grey matter in brain areas, the unusual birth-month effect, the geographical differences in incidence, the socio-economic predilection, the association with obstetrical abnormalities (low birth weight and prematurity), the decreased incidence of rheumatoid arthritis, and the association with viral epidemics (described above).

The hypothesis can be supported by finding significant association of sequence variants of folate, cobalamin, or pyridoxine genes with schizophrenia. Folate, cobalamin, and pyridoxine absorption, transport, and metabolism are complex [Rosenblatt, In: *The Metabolic and Molecular Bases of Inherited Disease*, Scriver et al. (eds), New York: McGraw-Hill, pp. 3111-3128 (1995); Benton and Rosenberg, In: *The Metabolic and Molecular Bases of Inherited Disease*, Scriver et al. (eds), New York: McGraw-Hill, pp. 3129-3149 (1995); Whyte et al., *Hypophosphatasia*, In: The Metabolic and Molecular Bases of Inherited Disease, Scriver et al. (eds), New York: McGraw-Hill pp. 4095-4111] with multiple transport proteins, enzymes, and regulatory components. A strong candidate for harboring a mutation predisposing to schizophrenia is the DHFR gene coding for the folate enzyme dihydrofolate reductase. DHFR chemically reduces dietary folate converting it into a form that can enter cellular metabolism. DHFR is also important for DNA synthesis and is known to play a major role in development in utero. A novel polymorphic 19 basepair deletion of the DHFR gene has been isolated which could be of functional significance because it affects potential transcription factor binding sites.

A second candidate is the MTHFR gene, coding for methylenetetrahydrofolate reductase, MTHFR, an important enzyme of folate metabolism. MTHFR was of particular interest because severe deficiency of enzyme activity has been associated with the "schizophrenia" phenotype [Freeman et al., *N. Engl. J. Med.*, 292:491-496 (1975); Regland et al., *J. Neural Transm. Gen. Sect.*, 98:143-152 (1994)] and because a common mutation, the nt677 C->T transition results in a mutated gene that encodes a heat-labile MTHFR, having decreased enzymatic activity, which in the presence of dietary folate deficiency, causes the plasma homocysteine of homozygotes to become elevated [van der Put et al., *Lancet.*, 346:1070-1071 (1995); Frosst et al., *Nature Genet.*, 10: 111-113 (1995)]. In adults, hyperhomocysteinemia is known to cause vascular disease and to be toxic [Frosst et al., *Nature Genet.*, 10:111-113 (1995)]. Therefore, homocysteine that crosses the placenta could act as a fetal teratogen during pregnancy. Maternal folate deficiency could also have a more direct teratogenic effect through fetal folate deprivation. These effects could be potentiated by abnormalities of other folate, cobalamin, or pyridoxine genes, even if these abnormalities were only minor.

Materials & Methods

1. Subjects and Sample Collection: Patients with schizophrenia and unaffected family members of schizophrenics, were ascertained from patient facilities, patient support groups, and family support group organizations. Nearly all schizophrenia families had only a single case of schizophrenia. The patients came from different schizophrenia families than the parents and sibs. The controls were unaffected and unrelated individuals not known to be schizophrenic or related to patients with schizophrenia or spina bifida. All subjects were of Caucasian background except two of the schizophrenia patients who were of African American background.

After informed consent was obtained, 20-40 ml of blood was collected into EDTA (purple-top) vacutainers, placed on ice immediately, and transported to the laboratory where plasma, packed red cells, and buffy coat were separated by centrifugation and frozen at −80° C.

2. Detection of Alleles: DNA was isolated using the QIAmp column DNA extraction procedure or the QIAGEN Genomic-tip method (QIAGEN, Chatsworth, Calif.). Alleles for a newly detected polymorphic 19 bp deletion in the dihydrofolate reductase (DHFR) gene were determined by polymerase chain reaction (PCR) amplification of the region surrounding the deletion using specific primers (FIG. 1) and direct detection of the PCR products after separation of products on a non-denaturing polyacrylamide gel. A Cetus—Perkin-Elmer 9600 thermocycler was used. Briefly, the PCR reaction contained 200 uM dNTPs, 1.5 mM $MgCl_2$, 10 pmols of each primer, in 10 ul reaction volume. The PCR conditions used were denaturation at 94° C. for 6 min. initially, followed by 35 cycles of 94° C. for 55 sec., 60° C. for 55 sec., and 72° C. for 55 sec. and a final extension at 72° C. for 12 min.

Alleles for the 677C->T transition of the methylenetetrahydrofolate reductase (MTHFR) gene were determined by cleavage with the restriction endonuclease, Hinf1, of PCR-amplified genomic DNA from blood and separation of the products by non-denaturing polyacrylamide gel electrophoresis [Frosst et al., *Nature Genet.*, 10:111-113 (1995)].

3. Sequencing the Region Around the DHFR Deletion: Using the same primers (FIG. 1), genomic DNA from individuals with 1,1 and 2,2 genotypes was amplified by PCR and the products sequenced using an ABI PRISM 377 automated sequencer. Restriction sites were identified using the MAP Program in the GCG Package. Potential transcription factor binding sites were detected with the TESS program (transcription element search software, URL:http://agave.humgen.upenn.edu/tess/index.html).

4. Data Analysis: Since the mode of inheritance of schizophrenia is unknown, binary logistic regression was used to test the DHFR deletion allele and the MTHFR heat-labile allele as genetic risk factors for schizophrenia. Either the DHFR deletion polymorphism or the MTHFR heat-labile allele could itself be a genetic risk factor for schizophrenia. The genotypes of the two folate gene polymorphisms were used as explanatory variables. Genotypes of schizophrenia patients, parents, or sibs were compared with those of controls.

Four files were constructed consisting of schizophrenia patients+controls, mothers of schizophrenia patients+controls, fathers of schizophrenia patients+controls, and sibs of schizophrenia patients+controls for input into the SAS System. Each dataset contained 6 variables. In order, these were:
1. six digit identification (ID) number;
2. response variable, i.e. affection status of the proband (0=unaffected, i.e. control individual; I=affected, i.e. schizophrenia patient);
3. DHFR mutation-single dose (Ds);
4. DHFR mutation-double dose (Dd);
5. MTHFR mutation-single dose (Ms); and
6. MTHFR mutation-double dose (Md).

For mutation data, 0=mutation absent, 1=mutation present.

Results

Alleles of the DHFR 19 bp Deletion Polymorphism: Amplification of the region of intron 1 of DHFR defined by the primers in FIG. 1 gave two polymorphic bands of 232 and 213 bp after separation on a non-denaturing polyacrylamide gel (FIG. 2). Sequencing the PCR products from the two homozygotes showed that they differed by 19 bp (FIG. 3). The upper and lower bands (FIG. 2), non-deletion allele and deletion allele respectively, were designated alleles 1 and 2 respectively. Comparison with two published sequences showed that allele 1 was identical with one of them [Yang et al. *J. Mol. Biol.* 176:169-187 (1984)] indicating that allele 2 resulted from a 19 bp deletion. The other published sequence [Chen et al. *J. Biol. Chem.* 259:3933-3943 (1984)] was lacking one base pair of allele 1, an A indicated by "*" in FIG. 3. It is possible that this shorter reference sequence [Chen et al. *J. Biol. Chem.* 259:3933-3943 (1984)] resulted from a sequencing artifact.

Sequences in the 19 bp Deleted Region of DHFR Intron 1: The 19 bp sequence in the deleted region (FIG. 3) of DHFR intron 1 contained sites for several restriction enzymes including RsaI and ScrFI, and potential binding sites for transcription factors including Sp1, NF-kappaB, CP1 (NF-Y), E2F, ETF and GCF in the 19 base pair region.

Binary Logistic Regression Analysis: The number of individuals with each genotype of the two polymorphisms among 38 unrelated schizophrenia probands, 35 unrelated mothers of schizophrenia probands, 15 unrelated fathers of schizophrenia probands, 13 unrelated unaffected sibs of schizophrenia probands, and 211 unrelated unaffected control probands is shown in Table 13.

TABLE 13

DISTRIBUTION OF DHFR AND MTHFR MUTATION GENOTYPES AND ALLELES AMONG CONTROLS, SCHIZOPHRENICS, AND SCHIZOPHRENIA FAMILY MEMBERS

| GenTyp | Schizophrenia | | | | |
|---|---|---|---|---|---|
| | P | M | F | S | Ctrl |
| DHFR 19 bp deletion polymorphism: | | | | | |
| 1/1 | 6 (.16) | 10 (.29) | 4 (.27) | 4 (.31) | 56 (.26) |
| 1/2 | 22 (.58) | 13 (.37) | 11 (.73) | 8 (.61) | 115 (.54) |
| 2/2 | 10 (.26) | 12 (.34) | 0 (0.0) | 1 (.08) | 40 (.19) |
| total | 38 (1.00) | 35 (1.00) | 15 (1.00) | 13 (1.00) | 211 (.99) |
| MTHFR 677C->T transition polymorphism: | | | | | |
| 1/1 | 14 (.37) | 16 (.46) | 11 (.73) | 4 (.31) | 103 (.49) |
| 1/2 | 18 (.47) | 18 (.51) | 3 (.20) | 8 (.61) | 78 (.37) |
| 2/2 | 6 (.16) | 1 (.03) | 1 (.07) | 1 (.08) | 30 (.14) |
| total | 38 (1.00) | 35 (1.00) | 15 (1.00) | 13 (1.00) | 211 (1.00) |

P = schizophrenia patients;
M = mothers of schizophrenia patients;
F = fathers of schizophrenia patients;
S = unaffected sibs of schizophrenia patients;
Ctrl = control individuals.

The four data files were analyzed using the logistic procedure of SAS (SAS Institute Inc., 1995) and the "descending" option, which modeled the probability that RESPONSE=1, that is, the probability that the proband was affected with schizophrenia. Note that the proband was not always the individual whose genotype data were used. For example, genotype data for mothers of schizophrenic probands were used to determine the probability that their children, the probands, were affected. Use of the "best" model selection options for logistic analysis in SAS gave the best models for two and three explanatory variables, (Table 14).

TABLE 14

BINARY LOGISTIC REGRESSION RESULTS

GENETIC RISK FACTOR
Odds Ratio (p value)    MODEL: Ds Dd Ms Md

| Schizophrenia Patients | |
|---|---|
| Ds OR(p) | 1.937 (.18) |
| Dd OR(p) | 1.263 (.59) |
| Ms OR(p) | 1.775 (.14) |
| Md OR(p) | 0.914 (.86) |
| Mothers of Schizophrenia Patients | |
| Ds OR(p) | 0.630 (.31) |
| Dd OR(p) | 2.653 (.028)* |
| Ms OR(p) | 1.439 (.34) |
| Md OR(p) | 0.143 (.065) |
| Fathers of Schizophrenia Patients | |
| Ds OR(p) | 1.178 (.79) |
| Dd OR(p) | 0.000 (.96) |
| Ms OR(p) | 0.366 (.14) |
| Md OR(p) | 0.841 (.88) |
| Unaffected Sibs of Schizophrenia Patients | |
| Ds OR(p) | 1.104 (.88) |
| Dd OR(p) | 0.337 (.31) |
| Ms OR(p) | 2.688 (.12) |
| Md OR(p) | 0.317 (.29) |

Notes For Table 14
DHFR 19 bp deletion: Ds = single dose; Dd = double dose
MTHFR 677C->T mutation: Ms = single dose; Md = double dose Logistic Regression Model Model with four explanatory variables (Ms, Md, Ds and Dd).
OR(p)=odds ratio and the corresponding p-value for that odds ratio determination *=significant at the $p \leq 0.05$ level.
0.000 odds ratios occurred since none of the fathers of schizophrenia patients had genotype Dd; there was a possibly quasi-complete separation in the sample points; the maximum likelihood estimate may not exist; and therefore validity of the model fit for these odds ratios was questionable.

The comparison of mothers of schizophrenia probands with control probands was statistically significant. Ds was not a significant genetic risk factor. Neither Ms nor Md in mothers was a significant genetic risk factor. However, the p-value for Md decreased and approached significance (p=0.065) at the p<0.05 level.

Predicted Probabilities of the Various Genotypes: The "probs predicted" modality of SAS, gave the predicted probability that the proband was affected with schizophrenia (response=1) given genotype data for control probands and schizophrenia patients (probands), mothers of schizophrenia probands, fathers of schizophrenia probands, or sibs of schizophrenia probands. The maximum probabilities obtained are shown in Table 15. The highest maximum predicted probability that the proband was affected was obtained for genotype data from mothers of schizophrenia probands, next for schizophrenia probands, next for fathers of schizophrenia probands, and lowest for sibs of schizophrenia probands.

TABLE 15

MAXIMUM PREDICTED PROBABILITY

| Model | P | M | F | S |
|---|---|---|---|---|
| Ds Dd Ms Md | 0.24 | 0.29 | 0.12 | 0.11 |

Model and explanatory variables are the same as in Table 14.

Determination of Genotypes Conferring the Highest Risk: The predicted probabilities that the proband was affected with schizophrenia given specific genotypes of control probands and schizophrenia probands, mothers of schizophrenia probands, fathers of schizophrenia probands, or sibs of schizophrenia probands were determined using the model containing all four explanatory variables (Table 16). The predicted probabilities that the proband was affected with schizophrenia were highest for maternal genotypes (Table 15). The maternal genotype with the highest risk was Dd Ms, conferring a probability of 0.29 of schizophrenia in the proband (Table 16). The Dd Ms genotype also gave the highest predicted probability, 0.24, for schizophrenia patients.

TABLE 16

PREDICTED PROBABILITIES FOR SPECIFIC GENOTYPES
Model: Ds Dd Ms Md

| Genotype | Predicted Probability | Genotype | Predicted Probability |
|---|---|---|---|
| Schizophrenia Patients: | | | |
| Dnull + Mnull | 0.07 | Ds + Ms | 0.20 |
| Dnull + Ms | 0.12 | Ds + Md | 0.19 |
| Dnull + Md | 0.11 | Dd + Ms | 0.24 |

TABLE 16-continued

PREDICTED PROBABILITIES FOR SPECIFIC GENOTYPES
Model: Ds Dd Ms Md

| Genotype | Predicted Probability | Genotype | Predicted Probability |
|---|---|---|---|
| Ds + Mnull | 0.12 | Dd + Md | 0.23 |
| Dd + Mnull | 0.15 | | |
| Mothers of Schizophrenia Patients: | | | |
| Dnull + Mnull | 0.16 | Ds + Ms | 0.13 |
| Dnull + Ms | 0.20 | Ds + Md | 0.02 |
| Dnull + Md | 0.03 | Dd + Ms | 0.29 |
| Dd + Mnull | 0.22 | Dd + Md | 0.06 |
| Ds + Mnull | 0.10 | | |
| Fathers of Schizophrenia Patients: | | | |
| Dnull + Mnull | 0.10 | Ds + Ms | 0.05 |
| Dnull + Ms | 0.04 | Ds + Md | 0.04 |
| Dnull + Md | 0.03 | Dd + Ms | 0.0 |
| Ds + Mnull | 0.12 | Dd + Md | 0.0 |
| Dd + Mnull | 0.0 | | |
| Unaffected Sibs of Schizophrenia Patients: | | | |
| Dnull + Mnull | 0.04 | Ds + Ms | 0.11 |
| Dnull + Ms | 0.10 | Ds + Md | 0.04 |
| Dnull + Md | 0.03 | Dd + Ms | 0.04 |
| Ds + Mnull | 0.04 | Dd + Md | 0.01 |
| Dd + Mnull | 0.02 | | |

Genotypes consist of the same explanatory variables described in Table 14 except that Dnull has no copy of the DHFR deletion and Mnull has no copy of the MTHFR 677C->T variant. Odds ratios of 0.0 were unsatisfactory as described in Table 14.

Discussion

Structure and Function of the DHFR 19 bp Deletion Polymorphism: DHFR polymorphisms have been reported previously [Feder et al., Nucl. Acids Res. 15:5906 (1987); Detera-Wadleigh et al., Nucl. Acids Res. 17:6432 (1989)]. It is known that introns are important for message regulation e.g., splicing, or as sites for binding transcription factors. Since the first intron is a relatively common location for regulatory elements, it is possible that the deleted region of DHFR intron 1 could play a role in regulation of DHFR or that the deletion could be a genetic risk factor for schizophrenia because it removes potential transcription factor binding sites. Abnormalities of transcription factors and their binding sites may play a role in disease. For example, a polymorphic Sp1 binding site in the collagen type 1 alpha 1 gene has been associated with reduced bone density and osteoporosis [Grant et al., Nature Genet. 14:203-205 (1996)].

The Nature of the Putative Folate Genetic Risk Factors for Schizophrenia: Dd in the mother of a schizophrenia proband conferred significantly increased risk of schizophrenia in her child (Table 14). The findings that Dd was a genetic risk factor in mothers but not fathers of schizophrenia probands (Table 15) and that Dd in mothers gave a higher predicted probability than in schizophrenia patients, fathers or sibs (Tables 15 and 16) was consistent with the role of DHFR as a teratogenic locus according to the gene-teratogen model (described above). The finding that a double dose but not a single dose of the DHFR deletion in mothers was a genetic risk factor (Table 16) supported a recessive mode of action in the mother. A teratogenic locus acting in the mother can also act as a modifying or specificity locus in the fetus.

Neither Ms nor Md in mothers of schizophrenia probands showed statistical significance as genetic risk factors for schizophrenia in probands (Table 14). However Md in mothers approached statistical significance (p=0.065) and appeared to be protective (odds ratio 0.14), while Ms in mothers appeared to increase risk modestly (odds ratio 1.44, p=0.34).

Role of Genetic and Environmental Factors in Schizophrenia: Since the probability that a schizophrenia co-twin is also affected is reported [Gottesman, Schizophrenia Genesis, Schizophrenia Genesis—The Origins of Madness, W.H. Freeman & Co. N.Y.(1991)] to be only 48%, a large part of the risk for schizophrenia would be anticipated to come from environmental factors. Therefore, some controls should have the genetic risk factors for schizophrenia but not be affected with schizophrenia. In the present data set, 6 of 35 schizophrenia mothers and 7 of 38 schizophrenia patients had Dd Ms, the genotype conferring the highest risk, compared with 15 of 211 controls. Since this genotype gave predicted probabilities of schizophrenia in probands of 0.29 and 0.24 respectively, polymorphisms of DHFR and MTHFR could account for a considerable portion of the genetic component of the risk of schizophrenia.

Relation of DHFR to Cytogenetic and Linkage Data for Schizophrenia: As discussed above, the DHFR gene has been located on chromosome 5 at 5q11.2-13.2. A schizophrenia translocation was reported (McGillivray et al. 1990; Bassett, 1992) affecting 5q11.2-5q13.3. Also two-point lod scores of 4.64 and 2.29 were found [Sherrington et al., Nature, 336: 164-167 (1988)] for the polymorphic markers D5S76 and D5S39 respectively on chromosome 5, in this region [McGillivray et al., Am. J. Med. Genet., 35:10-13 (1990); Bassett, Br. J. Psychiatry, 161:323-334 (1992)]. Two other linkage studies found small positive lod scores in this region [Coon et al., Biol. Psychiatry, 34:277-289 (1993); Kendler and Diehl, Schizophr. Bull., 19:261-285 (1993)], but numerous other studies excluded this region under the assumptions and models used [Kendler and Diehl, Schizophr. Bull., 19:261-285 (1993)]. Recently, new studies have found suggestive evidence for a potential susceptibility locus at a different region of 5q, 5q31 [Schwab et al., Nat. Genet. 11:325-327 (1997)] and 5q22-31 [Straub et al., Molec Psychiatr. 2:148-155 (1997)].

The case-control study presented herein illustrates the usefulness of the DNA polymorphism-Diet-Cofactor-Development and the gene-teratogen models described above. More importantly, the results presented herein, clearly fail to reject the specific models, i.e., that folate gene polymorphisms can play a role in the etiology of schizophrenia.

The present invention is not to be limited in scope by specific embodiments described herein. Indeed, various modifications of the invention in addition to those described herein will become apparent to those skilled in the art from the foregoing description and the accompanying figures. Such modifications are intended to fall within the scope of the appended claims.

Various publications in addition to the immediately foregoing are cited herein, the disclosures of which are incorporated by reference in their entireties.

We claim:

1. A method of estimating the genetic susceptibility of an individual to have or to develop a developmental disorder comprising:
   (a) collecting a biological sample from one or more participants; wherein a participant is either the individual or a blood relative of the individual; and wherein the biological sample contains nucleic acids and/or proteins of the participant;
   (b) analyzing the nucleic acids and/or proteins from the biological sample; wherein said analyzing results in a partial or full genotype for the alleles of the genes involved in folate, pyridoxine, and/or cobalamin metabolism; and wherein said partial or full genotype forms a dataset or datasets of genetic explanatory variables for the one or more participants;
   (c) adding the dataset or datasets of genetic explanatory variables obtained from step (b) to a genetic reference dataset therein forming a combined genetic dataset;
   (d) formulating a model comprising the genetic explanatory variables obtained from the one or more participants; and
   (e) analyzing the combined genetic dataset; wherein a predicted probability for the individual of having or developing a developmental disorder is determined; and wherein the genetic susceptibility of an individual to have or to develop a developmental disorder is estimated.

2. The method of claim 1 wherein said analyzing the combined genetic dataset is performed by binary linear regression.

3. The method of claim 2 further comprising the step of:
   (f) modifying the model by adding or subtracting a genetic explanatory variable; and re-analyzing the combined genetic dataset by binary logistic regression; wherein a model is chosen that best fits the data.

4. The method of claim 3 further comprising the step of:
   (g) testing the model for goodness of fit.

5. The method of claim 1 wherein the developmental disorder is selected from the group consisting of schizophrenia, spina bifida cystica, Tourette's syndrome, dyslexia, conduct disorder, attention-deficit hyperactivity disorder, bipolar illness, autism, chronic multiple tic syndrome and obsessive-compulsive disorder.

6. The method of claim 5 wherein the developmental disorder is schizophrenia and the individual is suspected of being genetically susceptible of having or for developing schizophrenia.

7. The method of claim 6 wherein the individual is suspected of being genetically susceptible for having or for developing schizophrenia because a blood relative has schizophrenia.

8. The method of claim 7 wherein the blood relative is a parent, a sibling, or a grandparent.

9. The method of claim 8 wherein the blood relative is a parent and wherein the parent is the mother of the individual.

10. The method of claim 1 wherein said analyzing the nucleic acids and/or proteins from the biological sample comprises determining if the biological sample contains a genetic variant of human dihydrofolate reductase having a nucleotide sequence with a 19 base-pair deletion spanning nucleotides 540 to 558 of the nucleotide sequence of SEQ ID NO:41; and wherein the genetic variant of human dihydrofolate reductase is an explanatory variable.

11. The method of claim 10 wherein said determining is performed by a method selected from the group consisting of PCR, special PCR, RT PCR, RFLP analysis, SSCP, and FISH.

* * * * *

SEQUENCE LISTING

<160> NUMBER OF SEQ ID NOS: 46

<210> SEQ ID NO 1
<211> LENGTH: 2187
<212> TYPE: DNA
<213> ORGANISM: Homo sapiens

<400> SEQUENCE: 1

| | | | | | |
|---|---|---|---|---|---|
| gccatggtga | acgaagccag | aggaaacagc | agcctcaacc | cctgcttgga | gggcagtgcc | 60 |
| agcagtggca | gtgagagctc | caaagatagt | tcgagatgtt | ccaccccggg | cctggaccct | 120 |
| gagcggcatg | agagactccg | ggagaagatg | aggcggcgat | tggaatctgg | tgacaagtgg | 180 |
| ttctccctgg | aattcttccc | tcctcgaact | gctgagggag | ctgtcaatct | catctcaagg | 240 |
| tttgaccgga | tggcagcagg | tggccccctc | tacatagacg | tgacctggca | cccagcaggt | 300 |
| gaccctggct | cagacaagga | gacctcctcc | atgatgatcg | ccagcaccgc | cgtgaactac | 360 |
| tgtggcctgg | agaccatcct | gcacatgacc | tgctgccgtc | agcgcctgga | ggagatcacg | 420 |
| ggccatctgc | acaaagctaa | gcagctgggc | ctgaagaaca | tcatgcgct | gcggggagac | 480 |
| ccaataggtg | accagtggga | agaggaggag | ggaggcttca | actacgcagt | ggacctggtg | 540 |
| aagcacatcc | gaagtgagtt | tggtgactac | tttgacatct | gtgtggcagg | ttaccccaaa | 600 |
| ggccaccccg | aagcagggag | ctttgaggct | gacctgaagc | acttgaagga | gaaggtgtct | 660 |
| gcggagccg | atttcatcat | cacgcagctt | tctttgagg | ctgacacatt | cttccgcttt | 720 |
| gtgaaggcat | gcaccgacat | gggcatcact | tgccccatcg | tccccgggat | ctttcccatc | 780 |
| cagggctacc | actcccttcg | gcagcttgtg | aagctgtcca | agctggaggt | gccacaggag | 840 |
| atcaaggacg | tgattgagcc | aatcaaagac | aacgatgctg | ccatccgcaa | ctatggcatc | 900 |
| gagctggccg | tgagcctgtg | ccaggagctt | ctggccagtg | gcttggtgcc | aggcctccac | 960 |
| ttctacaccc | tcaaccgcga | gatggctacc | acagaggtgc | tgaagcgcct | ggggatgtgg | 1020 |
| actgaggacc | ccaggcgtcc | cctaccctgg | gctctcagtg | cccaccccaa | gcgccgagag | 1080 |
| gaagatgtac | gtcccatctt | ctgggcctcc | agaccaaaga | gttacatcta | ccgtacccag | 1140 |
| gagtgggacg | agttccctaa | cggccgctgg | ggcaattcct | cttcccctgc | ctttggggag | 1200 |
| ctgaaggact | actacctctt | ctacctgaag | agcaagtccc | caaggagga | gctgctgaag | 1260 |
| atgtgggggg | aggagctgac | cagtgaagca | agtgtctttg | aagtctttgt | tctttacctc | 1320 |
| tcgggagaac | caaaccggaa | tggtcacaaa | gtgacttgcc | tgccctggaa | cgatgagccc | 1380 |
| ctggcggctg | agaccagcct | gctgaaggag | gagctgctgc | gggtgaaccg | ccagggcatc | 1440 |
| ctcaccatca | actcacagcc | caacatcaac | gggaagccgt | cctccgaccc | catcgtgggc | 1500 |
| tggggcccca | gcggggcta | tgtcttccag | aaggcctact | agagttttt | cacttcccgc | 1560 |
| gagacagcgg | aagcacttct | gcaagtgctg | aagaagtacg | agctccgggt | taattaccac | 1620 |
| cttgtcaatg | tgaagggtga | aaacatcacc | aatgcccctg | aactgcagcc | gaatgctgtc | 1680 |
| acttggggca | tcttccctgg | gcgagagatc | atccagccca | ccgtagtgga | tcccgtcagc | 1740 |
| ttcatgttct | ggaaggacga | ggcctttgcc | ctgtggattg | agcggtgggg | aaagctgtat | 1800 |
| gaggaggagt | ccccgtcccg | caccatcatc | cagtacatcc | acgacaacta | cttcctggtc | 1860 |
| aacctggtgg | acaatgactt | cccactggac | aactgcctct | ggcaggtggt | ggaagacaca | 1920 |
| ttggagcttc | tcaacaggcc | cacccagaat | gcgagagaaa | cggaggctcc | atgaccctgc | 1980 |
| gtcctgacgc | cctgcgttgg | agccactcct | gtcccgcctt | cctcctccac | agtgctgctt | 2040 |

| | |
|---|---:|
| ctcttgggaa ctccactctc cttcgtgtct ctcccacccc ggcctccact cccccacctg | 2100 |
| acaatggcag ctagactgga gtgaggcttc caggctcttc ctggacctga gtcggcccca | 2160 |
| catgggaacc tagtactctc tgctcta | 2187 |

<210> SEQ ID NO 2
<211> LENGTH: 7122
<212> TYPE: DNA
<213> ORGANISM: Homo sapiens

<400> SEQUENCE: 2

| | |
|---|---:|
| gcgcgtgtct ggctgctagg ccgacaccaa ggactggccg ggtacccggg aagaaagcac | 60 |
| gtgctccagc agttgccgcg cccagccccg agagaggccc tagggcgctg cgggctttcg | 120 |
| gggtccgcag tcccccgcg acgcgagcca acgggaggcg tcaaaagacc cgggccttgt | 180 |
| gtggcaggct cgcctggcgc tggctggcgt ggcccttggc cgtcgtcacc tgtggagagc | 240 |
| acgtcttctc tgccgcgccc tctgcgcaag gaggagactc acaacatgt cacccgcgct | 300 |
| ccaagacctg tcgcaacccg aaggtctgaa gaaaaccctg cgggatgaga tcaatgccat | 360 |
| tctgcagaag aggattatgg tgctggatgg agggatgggg accatgatcc agcgggagaa | 420 |
| gctaaacgaa gaacacttcc gaggtcagga atttaaagat catgccaggc cgctgaaagg | 480 |
| caacaatgac attttaagta taactcagcc tgatgtcatt taccaaatcc ataaggaata | 540 |
| cttgctggct ggggcagata tcattgaaac aaatactttt agcagcacta gtattgccca | 600 |
| agctgactat ggccttgaac acttggccta ccggatgaac atgtgctctg caggagtggc | 660 |
| cagaaaagct gccgaggagg taactctcca gacaggaatt aagaggtttg tggcaggggc | 720 |
| tctgggtccg actaataaga cactctctgt gtccccatct gtggaaaggc cggattatag | 780 |
| gaacatcaca tttgatgagc ttgttgaagc ataccaagag caggccaaag gacttctgga | 840 |
| tggcgggtt gatatcttac tcattgaaac tattttttgat actgccaatg ccaaggcagc | 900 |
| cttgtttgca ctccaaaatc tttttgagga gaaatatgct ccccggccta tctttatttc | 960 |
| agggacgatc gttgataaaa gtgggcggac tctttccgga cagacaggag agggatttgt | 1020 |
| catcagcgtg tctcatggag aaccactcta cattggatta aattgtgctt gggtgcagc | 1080 |
| tgaaatgaga ccttttattg aaataattgg aaaatgtaca acagcctatg tcctctgtta | 1140 |
| tcccaatgca ggtcttccca cacctttgg tgactatgat gaaacgcctt ctatgatggc | 1200 |
| caagcaccta aaggattttg ctatggatgg cttggtcaat atagttggag atgctgtgg | 1260 |
| gtcaacacca gatcatatca gggaaattgc tgaagctgtg aaaaattgta agcctagagt | 1320 |
| tccacctgcc actgcttttg aaggacatat gttactgtct ggtctagagc ccttcaggat | 1380 |
| tggaccgtac accaactttg ttaacattgg agagcgctgt aatgttgcag atcaaggaa | 1440 |
| gtttgctaaa ctcatcatgg caggaaacta tgaagaagcc ttgtgtgttg ccaaagtgca | 1500 |
| ggtggaaatg ggagcccagg tgttggatgt caacatggat gatggcatgc tagatggtcc | 1560 |
| aagtgcaatg accagatttt gcaacttaat tgcttccgag ccagacatcg caaaggtacc | 1620 |
| tttgtgcatc gactcctcca ttttgctgt gattgaagct gggttaaagt gctgccaagg | 1680 |
| gaagtgcatt gtcaatagca ttagtctgaa ggaaggagag gacgacttct ggagaaggc | 1740 |
| caggaagatt aaaaagtatg gagctgctat ggtggtcatg gcttttgatg aagaaggaca | 1800 |
| ggcaacagaa acagacacaa aaatcagagt gtgcacccgg gcctaccatc tgcttgtgaa | 1860 |
| aaaactgggc tttaatccaa atgacattat ttttgaccct aatatcctaa ccattgggac | 1920 |
| tggaatggag gaacacaact tgtatgccat taatttatc catgcaacaa aagtcattaa | 1980 |

```
agaaacatta cctggagcca gaataagtgg aggtctttcc aacttgtcct tctccttccg    2040
aggaatggaa gccattcgag aagcaatgca tggggttttc ctttaccatg caatcaagtc    2100
tggcatggac atggggatag tgaatgctgg aaacctccct gtgtatgatg atatccataa    2160
ggaacttctg cagctctgtg aagatctcat ctggaataaa gaccctgagg ccactgagaa    2220
gctcttacgt tatgcccaga ctcaaggcac aggagggaag aaagtcattc agactgatga    2280
gtggagaaat ggccctgtcg aagaacgcct tgagtatgcc cttgtgaagg gcattgaaaa    2340
acatattatt gaggatactg aggaagccag gttaaaccaa aaaaaatatc cccgacctct    2400
caatataatt gaaggacccc tgatgaatgg aatgaaaatt gttggtgatc tttttggagc    2460
tggaaaaatg tttctacctc aggttataaa gtcagcccgg gttatgaaga aggctgttgg    2520
ccaccttatc cctttcatgg aaaaagaaag agaagaaacc agagtgctta acggcacagt    2580
agaagaagag gacccttacc agggcaccat cgtgctggcc actgttaaag gcgacgtgca    2640
cgacataggc aagaacatag ttggagtagt ccttggctgc aataatttcc gagttattga    2700
tttaggagtc atgactccat gtgataagat actgaaagct gctcttgacc acaaagcaga    2760
tataattggc ctgtcaggac tcatcactcc ttccctggat gaaatgattt ttgttgccaa    2820
ggaaatggag agattagcta aaggattcc attgttgatt ggaggagcaa ccacttcaaa    2880
aacccacaca gcagttaaaa tagctccgag atacagtgca cctgtaatcc atgtcctgga    2940
cgcgtccaag agtgtggtgg tgtgttccca gctgttagat gaaaatctaa aggatgaata    3000
ctttgaggaa atcatggaag aatatgaaga tattagacag gaccattatg agtctctcaa    3060
ggagaggaga tacttaccct taagtcaagc cagaaaaagt ggtttccaaa tggattggct    3120
gtctgaacct cacccagtga agcccacgtt tattgggacc caggtctttg aagactatga    3180
cctgcagaag ctggtggact acattgactg gaagcctttc tttgatgtct ggcagctccg    3240
gggcaagtac ccgaatcgag gctttcccaa gatatttaac gacaaaacag taggtggaga    3300
ggccaggaag gtctacgatg atgcccacaa tatgctgaac acactgatta gtcaaaagaa    3360
actccgggcc cggggtgtgg ttgggttctg gccagcacag agtatccaag acgacattca    3420
cctgtacgca gaggctgctg tgccccaggc tgcagagccc atagccacct tctatgggtt    3480
aaggcaacag gctgagaagg actctgccag cacggagcca tactactgcc tctcagactt    3540
catcgctccc ttgcattctg gcatccgtga ctacctgggc ctgtttgccg ttgcctgctt    3600 tgggggtagaa gagctgagca aggcctatga ggatgatggt gacgactaca gcagcatcat    3660
ggtcaaggcg ctgggggacc ggctggcaga ggcctttgca gaagagctcc atgaaagagt    3720
tcgccgagaa ctgtgggcct actgtggcag tgagcagctg gacgtcgcag acctgcgcag    3780
gctgcggtac aagggcatcc gcccggctcc tggctacccc agccagcccg accacaccga    3840
gaagctcacc atgtggagac tcgcagacat cgagcagtct acaggcatta ggttaacaga    3900
atcattagca atggcacctg cttcagcagt ctcaggcctc tacttctcca atttgaagtc    3960
caaatatttt gctgtgggga agatttccaa ggatcaggtt gaggattatg cattgaggaa    4020
gaacatatct gtggctgagg ttgagaaatg gcttggaccc atttgggat atgatacaga    4080 ctaacttttt tttttttttgc cttttttatt cttgatgatc ctcaaggaaa tacaacctag    4140
ggtgccttaa aaataacaac aacaaaaaac ctgtgtgcat ctggctgaca cttacctgct    4200
tctggttttc gaagactatt tagtggaacc ttgtagagga gcagggtctt cctgcagtgc    4260
ctggaaaaca ggcgctgttt ttttgggacc ttgcgtgaag agcagtgagc agggttcctg    4320
tggtttccct ggtccctctg agatggggac agactgaaga cagaggtcgt ttgatttcaa    4380
```

```
agcaagtcaa cctgctttt tctgttttta cagtggaatc taggaggcca cttagtcgtc   4440
ttttttcct cttagaagaa aagcctgaaa ctgagttgaa tagagaagtg tgaccctgtg   4500
acaaaatgat actgtgaaaa atggggcatt ttaatctaag tggttataac agtggattct   4560
gacggggaag gtgtagctct gttctcttcg gaagacctcg ttttctaaag ctggactaa    4620
atggctgcag aactcccttt ggcaaaaggc atgcgctcac tgcttgcttg tcagaaacac   4680
tgaagccatt tgccccagtg tggtcaagca gccatgcttt ctgggcattt tcgtcctccc   4740
ataatttcat atttccgtac ccctgaggaa acaaaaagga aatgaggaga gaaagttact   4800
gttaagggtg gttaacattt ttttttgtttt gttttgtttt ggttttttttt ttttgagaca   4860
gagtctggct ctgtcgccca ggctggagtg caggggcgca atctcggctc atagcaagct   4920
ccgcctcctg ggttcatgcc attcctctgc ctcagcctcc agagtagctg ggactacagg   4980
tgcccaccac cacacccggc taattttttg tgttttttaca aaatacaaaa aagtagagac   5040
aggatttcac tgtgttagcc aggatggtct tgatctcccg acctcgtgat ctgcccacct   5100
cagcctccca aaatgctggg attacaggcg tgagccaccg agcctggccg gttaacatct   5160
tttaattgtt tccaggattg agcaggttct cagctgggct ctgatatccc gtgcggagtt   5220
ggacaagtgg gcagcataaa gtcactcatt tcttaccatt ttattcccct caattctcaa   5280
tatattcagt aatgaagaat ggtgccacca ctcaagcaac aagcctcaaa ctcaaccatg   5340
tcatcttttt cttggatgat gcagttatt tcaaaaattt gcatgcaaaa tatacactca    5400
tcctacttca agatggtggt ggcaatagtc aggagaaggt aacattggag tcctggtttg   5460
attcgaagga tgaagacgaa gaagcaaggg aggaacaaat gaagaaccat ctttgttcat   5520
gaataggaat attcaagatt ataaaggtat caggtctcct aaaattgatc tatggattta   5580
ataccatttt caatggaaat tccaacagat tttattgaat gaaacaagca ggtgtttata   5640
tggagtagca aaggacttaa aattaccaaa tgcttctaaa tatgaaggag aggttgggga   5700
cacgcaccct atgtgatacc aagttttatt gtcaagacag tgtcatggtg cagaggtagg   5760
cattctgagc aggggaacaa aataagggcc tagaaactca cccgtgcata tgttgacctt   5820
tgcaaaatga cctggtgaca tggcaagtca gtggggacag aaggaccac tccctaagta    5880
atcccagaac aatggctatt catgtgggaa aaaagaaat tttactttct ctcaccttac    5940
ctggtgataa gttccaaata tgttaagggc tttaatacaa aaagcaaaaa ttgtcagtgt   6000
ttggatgaaa aaagccttag ggcaggaaag aatctcttga gacataaagt agtaatcata   6060
aaggacaaga tggttaagtc aattctgtta aaactcaagg cttatattaa gcaaacactt   6120
gaagtgagaa gatgatccac aacttgagaa gacatttata atacaaataa ctgatgaagg   6180
attcataatc acaaatatag agaattccta tttaaaaaa tagaaaaata gtgaagacta   6240
cacaagagga ataggggctt ttaaataaat agatgttctg tagcattggt cagggaaata   6300
tgaattagga ccacaatgag attccatttt atatccataa gatttgcaaa ggtttgggtct  6360
gacagtacca gttgttagat ctgtagggac ttgtacaaca ttgtggatgt gtaaacaggc   6420
accactgctt taaaaaacaa ttatcccctta cagacttgaa catttgcaga cgttatgatc   6480
ttgcttccaa ctcccacctg tatgtccagc aaactcttgc atgtggccac taggaggaat   6540
gtgtaagaat gttcatagtt acatatttat aatagttaat aactgaaaa agtgaaatgt    6600
atgtctgtct acaggaaaat aggtgaataa ttagatatat atattcattc tacgggatat   6660
tattcagtag tggaaatgag tgaactacag ctataccctca caataagaat gaatctcaga   6720
aaatattaag gaaaaaagca agtttgaaga gaccacatgg ggcgtactat ttttattggg   6780
```

-continued

```
cccaaaaaca agcaaaacca aagaatatgt agtctaagca tacgtataca ataaaactat    6840
gctattaaaa aaaaaaggta actgataaac caaaattgag catagtaatt acccacagaa    6900
ggaggaagtg gaagggacag gagcacatag gtagatgcca agttatgcag ctgttctggt    6960
tcctcctggt aggcttacaa gtgtttacta tatgctatta atacattata ctttataact    7020
aatagataac agttttttac atattaaata tgttctactt aaatatatta taaaaaataa    7080
aggcaaagtg gaatgtttaa aaaaaaaaaa aaaaaaaaa aa                        7122

<210> SEQ ID NO 3
<211> LENGTH: 564
<212> TYPE: DNA
<213> ORGANISM: Homo sapiens

<400> SEQUENCE: 3
atggttggtt cgctaaactg catcgtcgct gtgtcccaga acatgggcat cggcaagaac      60
ggggacctgc cctggccacc gctcaggaat gaattcagat atttccagag aatgaccaca     120
acctcttcag tagaaggtaa acagaatctg gtgattatgg gtaagaagac ctggttctcc     180
attcctgaga gaatcgacc tttaaagggt agaattaatt tagttctcag cagagaactc     240
aaggaacctc cacaaggagc tcattttctt tccagaagtc tagatgatgc cttaaaactt     300
actgaacaac cagaattagc aaataaagta gacatggtct ggatagttgg tggcagttct     360
gtttataagg aagccatgaa tcacccaggc catcttaaac tatttgtgac aaggatcatg     420
caagactttg aaagtgacac gttttttcca gaaattgatt tggagaaata taaacttctg     480
ccagaatacc caggtgttct ctctgatgtc caggaggaga aggcattaa gtacaaattt     540 gaagtatatg agaagaatga ttaa                                           564

<210> SEQ ID NO 4
<211> LENGTH: 2158
<212> TYPE: DNA
<213> ORGANISM: Homo sapiens

<400> SEQUENCE: 4
gcgcggcata acgacccagg tcgcggcgcg gcggggcttg agcgcgtggc cggtgccgca      60
ggagccgagc atggagtacc aggatgccgt gcgcatgctc aatacccctg cagaccaatgc    120 cggctacctg gagcaggtga agcgccagcg gggtgaccct cagacacagt tggaagccat     180
ggaactgtac ctggcacgga gtgggctgca ggtggaggac ttggaccggc tgaacatcat     240
ccacgtcact gggacgaagg ggaagggctc cacctgtgcc ttcacggaat gtatcctccg     300
aagctatggc ctgaagacgg gattctttag ctctcccac ctggtgcagg ttcgggagcg     360
gatccgcatc aatgggcagc ccatcagtcc tgagctcttc accaagtact ctggcgcgct    420
ctaccaccgg ctggaggaga ccaaggatgg cagctgtgtc tccatgcccc cctacttccg     480
cttcctgaca ctcatggcct tccacgtctt cctccaagag aaggtggacc tggcagtggt     540
ggaggtgggc attggcgggg cttatgactg caccaacatc atcaggaagc ctgtggtgtg     600
cggagtctcc tctcttggca tcgaccacac cagcctcctg ggggatacgg tggagaagat     660
cgcatggcag aaaggggggca tctttaagca aggtgtccct gccttcactg tgctccaacc     720
tgaaggtccc ctggcagtgc tgagggaccg agcccagcag atctcatgtc ctctataccct    780 gtgtccgatg ctggaggccc tcgaggaagg ggggccgccg ctgaccctgg gcctggaggg     840
ggagcaccag cggtccaacg ccgccttggc cttgcagctg gccccactgc tggctgcagcg     900 gcaggaccgc catggtgctg gggagccaaa ggcatccagg ccagggctcc tgtggcagct     960
```

```
gcccctggca cctgtgttcc agcccacatc ccacatgcgg ctcgggcttc ggaacacgga    1020
gtggccgggc cggacgcagg tgctgcggcg cgggcccctc acctggtacc tggacggtgc    1080
gcacaccgcc agcagcgcgc aggcctgcgt gcgctggttc cgccaggcgc tgcagggccg    1140
cgagaggccg agcggtggcc ccgaggttcg agtcttgctc ttcaatgcta ccggggaccg    1200
ggacccggcg gccctgctga agctgctgca gccctgccag tttgactatg ccgtcttctg    1260
ccctaacctg acagaggtgt catccacagg caacgcagac caacagaact tcacagtgac    1320
actggaccag gtcctgctcc gctgcctgga acaccagcag cactggaacc acctggacga    1380
agagcaggcc agcccggacc tctggagtgc cccagcccca gagcccggtg ggtccgcatc    1440
cctgcttctg gcgccccacc caccccacac ctgcagtgcc agctccctcg tcttcagctg    1500
catttcacat gccttgcaat ggatcagcca aggccgagac ccatcttcc agccacctag     1560 tcccccaaag ggcctcctca cccaccctgt ggctcacagt ggggccagca tactccgtga    1620
ggctgctgcc atccatgtgc tagtcactgg cagcctgcac ctggtgggtg tgtcctgaa     1680 gctgctggag cccgcactgt cccagtagcc aaggcccggg gttggaggtg ggagcttccc    1740
acacctgcct gcgttctccc catgaactta catactaggt gccttttgtt tttggctttc    1800
ctggttctgt ctagactggc ctaggggcca gggctttggg atgggaggcc gggagaggat    1860 gtcttttta aggctctgtg ccttggtctc tccttcctct tggctgagat agcagagggg     1920
ctccccgggt ctctcactgt tgcagtggcc tggccgttca gcctgtctcc cccaacaccc    1980
cgcctgcctc ctggctcagg cccagcttat tgtgtgcgct gcctggccag gccctgggtc    2040
ttgccatgtg ctgggtggta gatttcctcc tcccagtgcc ttctgggaag ggagagggcc    2100
tctgcctggg acactgcggg acagagggtg gctggagtga attaaagcct tgttttt      2158
```

<210> SEQ ID NO 5
<211> LENGTH: 7720
<212> TYPE: DNA
<213> ORGANISM: Homo sapiens

<400> SEQUENCE: 5

```
taagttgaca cttctcaggt tgtcacaaga ttcaggtatg gctcactgtt gcaggacata      60
agctgggatc tcctgggaat tggtctgctt gcaggcccta gagagccttc cttcttggtt     120
gattttcctc tagagatcca actgtcttct caggctcccc tgcctgcctc ctccttgggt     180
cctttcttgt ggcattgcca gattactggg cccccatttt ccctacactt actgccactc     240
atagtctgat ggttcccaca tctgcatcca acctggactc ttccctgag ctttcccctc      300 tacaaccacc ttccccgggc caagggcaca caggcacctc gacaaaacag tgttctatgt     360
ttcttcctgc ccaaacctgc ccctcctct ccttttccc atctgtggta ccaccatggg      420
ctcagagaat aaaaaaaatg aaggcttctg tcattgactg gggtggagat ggagggaaga    480
gttagcccag aatcacaggt gctgtagaaa ggatacctga gttgccggga gaggggtcc     540 atgagttggg gatggaagga gagcttggcc cttcaaacaa ttgaagatct gatcaaaga      600 ttcagaacat ctgtgatttt gtggctggtg atgggtgaca cctgggctaa tggggttggg    660
ggagttggtg gctctacaat ttatggcctt gggagatcct tgctctctat agctgactgg    720
gaggttggaa gcctgggctc tagcccttgc cttgatcctc cggatctcat tttcctcatc    780
tgcctaacag gacagagggg ttggaaactg atgagattag ctcaaaggat cctggcagct    840
caggctgcaa gattttttc agacctcagt gtttgggaaa aaattgggta ggtgagctt     900 agggactggc cttaggcctg cactgttaat tcaccccctc ccactacccc atggaggcct    960
```

```
ggctggtgct cacatacaat aattaactgc tgagtggcct tcgcccaatc ccaggctcca    1020
ctcctgggct ccattcccac tccctgcctg tctcctaggc cactaaacca cagctgtccc    1080
ctggaataag gcaaggggga gtgtagagca gagcagaagc ctgagccaga cggagagcca    1140
cctcctctcc caggtatgtg acactcccca tcccccttca gaggccacac ccctatggc     1200 attcccacca tgtgttaagg attttctgaa ctggaagggc cctctgtttg cctgaaggcc    1260
agagaatctt gaagtggaga ctgaggccca gaccagagtg tggcctgctc aagattaaac    1320
gacaagttag tgttcatccc cctgaactag tacctgggct ctagcccttc agtccagagc    1380
tgagttctca gctcttctag tctggggccc caaggttggg tgtgggggtc atgattgttg    1440
gtggggaggg gtcacagctg gactaagacc tgaaggtgag actaggcagg tgggaaagga    1500
gcttgcagag tgatgctgct caaaaggaca ggaagagagc ctggcttcag aagcagccac    1560
agcaagagag actactgact gaacaggtgg gctccactgg gggctccgga aaggattttc    1620
tcagccccca tccccagcac tgtgtgttgg ccgcacccat gagagcctca gcactctgaa    1680
ggtgcagggg gcaaaggcca aaagagctct ggcctgaact tgggtggtcc ctactgtgtg    1740
acttggggca tggccctcat ctgtgctgaa atgattccac aaagattaaa ctggctatca    1800
tttgttgatt tccccttct  tacatttaat ccttgcagga gaaagctaag cctcaagata    1860
gtttgcttct ctttccccca aggccaagga gaaggtggag tgagggctgg ggtcgggaca    1920
ggttgaacgg gaaccctgtg ctctaaacag ttagggtttg ttcccgcagg aactgaaccc    1980
aaaggatcac ctggtattcc ctgagagtac agatttctcc ggcgtggccc tcaaggttag    2040
tgagtgagca ggtccacagg ggcatgattg gatcctggaa tgaatgaatc aaccatgaga    2100
gagtgaatga acactggaat caatagagta gcagagtaat ggattgtgga gcaggaaaga    2160
gagctgctgg gtgggaattc aattccaggc ttatatgagc cctgctgtgc agtcggcctg    2220
gagacagccc agctcaggcc ctgcctagac ccctgtcaag gaggccctgt caagaggaga    2280
ggaggggcag cacgggggca aggcaagctt gtgagcggga aaggcatgtc cacttttagcg    2340 actggtatgt ggaagatgag ttagaggaga cagatggaga gaagtcatag gaaataaatt    2400
ctgagcattt taggagggcc cagacacctg tgtccagtg  gagtgaagga aacagtcgcc    2460
tcccaaaatt cagtgtctga ggtcaaagga ttgaagttct gtgatgacca aggagaagcc    2520
agctctgtgg taggggcac  aggagctccc caaggcccca gggctgtcca gctggctgtc    2580
ccctgccagc acccatgtcc tgtgacccca ccccaccaag atcccatggt tccgggaag    2640 ggcctactaa actagcttga gtgatgaggc tagaaagggg ctgggaccaa ggtttaaaaa    2700
gcaaaacaaa ctaacaaaaa ccacactgca gccccccaa  ctaaaacatt tttataaact    2760 ttttttttt  ttttgagatg gagtctcgct ctgtcaccca ggctagagtg caatggcaca    2820
atcttggctc actgtaacct ccacctcctg gattcaagtg attctcctgc ctcagcctcc    2880
cacgtagctg ggactacagg cacacgacac cgcacccagc tcattttgta ttttagtag    2940 agacagggtt tcactatgtt ggccaggctg gtctcaaact tctgacctca ggtgatccac    3000
ccacctcagc cttccaaagt gctgggatta caggcatgag ccaccgcgcc cagcccattt    3060
ttgtaaactt ttacaatgaa gtaatttggt gtcaaaatct gacctgaaaa ttaatgtgag    3120
tttatgtata gttttaattt atcccactag tgtaactgtt tcaccccaga atatacactt    3180
gattattggg tatatgaaaa aaatattttc tttgaatcac ctttgatgaa atcctaaaaa    3240
atttaacccc tgaaacattt gaataaggca ttgtggacct atggcaaact cctggctatt    3300
tctgcatttt gcccaaatcc atccttgaat tatatcacct gaacctcgtg accacctgga    3360
```

```
gaaggcaatg aggctcaagc cagggagggg tggtgtctaa tcctaccttt cattggatct      3420
gggaaaactg agggagatgg gggcagggct ctatctgccc caggcttccg tccaggcccc      3480
accctcctgg agccctgcac acaacttaag gccccacctc cgcattcctt ggtgccactg      3540
accacagctc tttcttcagg gacagacatg gctcagcgga tgacaacaca gctgctgctc      3600
cttctagtgt gggtggctgt agtagggag gctcagacaa ggattgcatg gccaggact       3660 gagcttctca atgtctgcat gaacgccaag caccacaagg aaaagccagg ccccgaggac      3720
aagttgcatg agcaggtggg ccaggggtg atctggggtg gtgagggact ggctcaggaa      3780
gaggaaacga ggacatggaa atgccaaacc ccattggcac tggtgaactg aagtggagga      3840
gcccttcagt ttgcattaat atgggtgact tatttcagag acactgtgcc aaatgtcggt      3900
acaatgccaa cagttcacct tcttggttgt tgagtttccg cattacagaa ataaggaagc      3960
aggcccaaag gagagcctgg gaaatgaagt tggagtgacc catcctgggg ttgcttgatt      4020
tagggattta gactgggaat gactcctcca aagatctgag ggaagaaact gcacactgtg      4080
catagtggcc tctttctgc cagccctaaa cagctcaaga agggagagtc tctcacatta      4140
tgaggctgtg tgcaaagcat tctttttttt ttttcctgag acaaagtctc catatgttgc      4200
ccaggctggt ctcaaattcc tggactcaag tgatcctccc acctcagccc tcccaaagtg      4260
tgggattaca gaaatgagcc gtacgccctc ctgaagcatc ttggttcatg catctcgcaa      4320
aactttgggc tgtgtctctc gaccacattg gacctgaggt ctccctataa catttatttt      4380
gctaccaccc ctttaatatc ctgaacatga tgatataact aaagaaaaag cagaggaaaa      4440
gtaatttgta ggccaggtgt tacggctcac gcctgtaatc ccaacactgt gggatgtcga      4500
gatgggcaga tcacttgagc tcaggagttc gagaccagcc tggcaagat ggcaaaaccc       4560 catctctact aaaaaataaa aaaattagt caggtgtggt ggcacatgcc tgcagtccca      4620
gctactcagg aggctgaggt gggcaggtca gttgagccca ggaggcagag attgtagatc      4680
gtgccactgc actccagcct gggcaacaga gtgagacctt gtcaaaagaa agaaagaacg      4740
aaaaaaagaa agaaaggaag gaaggaaggg gaggaaggaa agggagggag gaaagggagg      4800
gaggaaaggg agggaggcaa gggagagaaa cttgtaatac gcatttcttt ttttttttct      4860
tgagatagag ttttgctctt gttgcccagg gtggatggca gtggcacaat ctcagctcac      4920
tgcaacctcc acctcccagg ttcaagtgat tctcctgcct cagcctcctg agtaggcaca      4980
cgccaccaca cccagctaat ttttttgtttg tttgtttgtt ttgtttgttg gtatttttag     5040
tagagatggg ggtttcacca tgttggccag gctggtctcg aactcctcac ctcataatcc      5100
gcccctcttg gcctcccaaa gtgctgagat tacaggtgtg agccactgcg cccggcctta      5160
agtgcacatt ttatttattt atttatttat ttatttattg agatggagtc ttgctctgtt      5220
gcccaggctg gagtgcagtg gcacaatctc agctcactgc aacctccacc tcccaggttc      5280
aagcaattct tctgccttgg cctccagagt agctgggact ataggcacct gccaccatgc      5340
ctagctaatt tttgtatttt tagtagaaat ggggttttgc catgttggcc aggctggtct      5400
ccattcttga cctaagtga tctgtccacc tccacctccc aaagtgctgg gattacaggc      5460
actatgtgag ccactgtgcc ggcccacatt ttaatattta gcttgtcagc cttaagtaat      5520
gagattcagg aagcttgagg ataggcacac aggagcatag tttcaagttg tcctgaattt      5580
tgcagccatc acaagttagt ttttaaggaa aaagattagt tcctaagttg tttctcaata      5640
acttataata aaataacatc cacaattgat tggctataca ttgttttttt gtatcacaaa      5700
ttccacaaac agataatggg tgaggcagct agtcagggac aaaacacttc ccaagtagct      5760
```

```
gggattacag gtgtccgcca ccacacttgg ctagttttttt gtttgtttat ttttgagat    5820
ggagtcttgc tctgtcgccc aggctggagt gcagtggcat gatctcggct cactgcaagc   5880
tccacctgcc gggttcacac cattctcctg cctcagcctc ccaagtagct gggactacag   5940
gtgccagcca ccacgcccgg ctaatttttt gtattttttag tagagacggg gtttcaccat   6000
gttggccagg atggtcttga tctcttagcc tcgtgatcca cccgcctcgg cctcccaaaa   6060
tgctgggatt acaggcgtga gccaccgcac ccggcctaat ttttatattt ttagtagaga   6120
cggggtttca ccatgttggc caggctggtc tcaaactctt gatctcaggt gatccacctg   6180
ccttggcctc ccaaagtgct gggattacac aagtaagcca ctgcacccag cctggggtta   6240
caatttaaat tgcttttttta ccttcaaatc tttgacacct cagtgaggct taatctgacc   6300
gcactattac actacaagtc cccatccgtc tctgcttaat ttttgtccaa agcaaaaatc   6360
aggtgatgtg ttcattgttg taaccccagt ttctacaaaa gtacctgggt gagagtaagt   6420
aggatctcaa taaaggttga attaacaaat tttgtaatga ctgcaactcc agcaggagct   6480
cccttttggg ctcccactgt ctctgacggc cctctcccct aaagaggtcc caatagcaag   6540
tattttcctg ggtgacttcc agtgggctgg ggaatcaagg actaagaggg gagacactgc   6600
atgtggaata ttctggctgt gctggctgtg ctggctgtgg actgagtcct ctgtcttccc   6660
ccatccagtg tcgaccctgg aggaagaatg cctgctgttc taccaacacc agccaggaag   6720
cccataagga tgtttcctac ctatatagat tcaactggaa ccactgtgga gagatggcac   6780
ctgcctgcaa acggcatttc atccaggaca cctgcctcta cgagtgctcc cccaacttgg   6840
ggccctggat ccagcaggta tgcatggctt cctgcaggta caagacctag cggagcagct   6900
gagcttttcca ggcatctctg caggctgcaa ccccagctcc agttctattc ggggctgagt   6960
tgctgggatt cttgaacctg agcccttctt ttgtatcaaa atcacccagg tggatcagag   7020
ctggcgcaaa gagcgggtac tgaacgtgcc cctgtgcaaa gaggactgtg agcaatggtg   7080
ggaagattgt cgcacctcct acacctgcaa gagcaactgg cacaagggct ggaactggac   7140
ttcaggtgag ggctggggtg ggcaggaatg gagggatttg gaagtggagg tgtgtgggtg   7200
tggaacaggt atgtgacaat ttggagttgt agggctggca gacctcaaga tagttccggg   7260
cccagtggct aaaggtcttc cctcctctct acagggttta acaagtgcgc agtgggagct   7320
gcctgccaac ctttccattt ctacttcccc acacccactg ttctgtgcaa tgaaatctgg   7380
actcactcct acaaggtcag caactacagc cgagggagtg gccgctgcat ccagatgtgg   7440
ttcgacccag cccagggcaa ccccaatgag gaggtggcga ggttctatgc tgcagccatg   7500
agtggggctg ggccctgggc agcctggcct ttcctgctta gcctggccct aatgctgctg   7560
tggctgctca gctgacctcc ttttaccttc tgatacctgg aaatccctgc cctgttcagc   7620
cccacagctc ccaactattt ggttcctgct ccatggtcgg gcctctgaca gccactttga   7680
ataaaccaga caccgcacat gtgtcttgag aattatttgg                         7720
```

<210> SEQ ID NO 6
<211> LENGTH: 255
<212> TYPE: PRT
<213> ORGANISM: Homo sapiens

<400> SEQUENCE: 6

Met Val Trp Lys Trp Met Pro Leu Leu Leu Leu Val Cys Val Ala
1               5                   10                  15

Thr Met Cys Ser Ala Gln Asp Arg Thr Asp Leu Leu Asn Val Cys Met
            20                  25                  30

```
Asp Ala Lys His His Lys Thr Lys Pro Gly Pro Glu Asp Lys Leu His
            35                  40                  45

Asp Gln Cys Ser Pro Trp Lys Lys Asn Ala Cys Cys Thr Ala Ser Thr
        50                  55                  60

Ser Gln Glu Leu His Lys Asp Thr Ser Arg Leu Tyr Asn Phe Asn Trp
 65                 70                  75                  80

Asp His Cys Gly Lys Met Glu Pro Ala Cys Lys Arg His Phe Ile Gln
                85                  90                  95

Asp Thr Cys Leu Tyr Glu Cys Ser Pro Asn Leu Gly Pro Trp Ile Gln
            100                 105                 110

Gln Val Asn Gln Thr Trp Arg Lys Glu Arg Phe Leu Asp Val Pro Leu
        115                 120                 125

Cys Lys Glu Asp Cys Gln Arg Trp Trp Glu Asp Cys His Thr Ser His
130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Arg Cys Ile Gln Met Trp Phe
        195                 200                 205

Asp Ser Ala Gln Gly Asn Pro Asn Glu Glu Val Ala Arg Phe Tyr Ala
210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255

<210> SEQ ID NO 7
<211> LENGTH: 817
<212> TYPE: DNA
<213> ORGANISM: Homo sapiens

<400> SEQUENCE: 7
cgcaggaata gatggacatg gcctggcaga tgatgcagct gctgcttctg gctttggtga      60
ctgctgcggg gagtgcccag cccaggagtg cgcgggccag gacggacctg ctcaatgtct     120
gcatgaacgc caagcaccac aagacacagc ccagccccga ggacgagctg tatggccagt     180
gcagtccctg gaagaagaat gcctgctgca cggccagcac cagccaggag ctgcacaagg     240
acacctcccg cctgtacaac tttaactggg atcactgtgg taagatggaa cccacctgca     300
agcgccactt tatccaggac agctgtctct gagtgctcac caacctgggc cctggatc      360
cggcaggtca accagagctg cgcaaagag cgcattctga acgtgcccct gtgcaaagag     420
gactgtgagc gctggtggga ggactgtcgc acctcctaca cctgcaaaag caactggcac     480
aaaggctgga attggacctc aggattaat gagtgtccgg ccggggccct ctgcagcacc     540
tttgagtcct acttccccac tccagccgcc ctttgtgaag gctctggag ccactccttc     600
aaggtcagca actatagtcg agggagcggc cgctgcatcc agatgtggtt tgactcagcc     660
cagggcaacc ccaatgagga ggtggccaag ttctatgctg cggccatgaa tgctggggcc     720
ccgtctcgtg ggattattga ttcctgatcc aagaagggtc tctgggggtt cttccaacaa     780
cctattctaa tagacaaatc cacatgaaaa aaaaaaa                             817

<210> SEQ ID NO 8
```

<211> LENGTH: 1669
<212> TYPE: DNA
<213> ORGANISM: Homo sapiens

<400> SEQUENCE: 8

```
gctaggcagc ttcgaaccag tgcaatgacg atgccagtca acggggccca caaggatgct      60
gacctgtggt cctcacatga caagatgctg gcacaacccc tcaaagacag tgatgttgag     120
gtttacaaca tcattaagaa ggagagtaac cggcagaggg ttggattgga gctgattgcc     180
tcggagaatt tcgccagccg agcagttttg gaggccctag gctcttgctt aaataacaaa     240
tactctgagg ggtacccggg ccagagatac tatggcggga ctgagtttat tgatgaactg     300
gagaccctct gtcagaagcg agccctgcag gcctataagc tggacccaca gtgctggggg     360
gtcaacgtcc agccctactc aggctcccct gcaaactttg ctgtgtacac tgccctggtg     420
gaaccccatg ggcgcatcat gggcctggac cttccggatg ggggccacct gacccatggg     480
ttcatgacag acaagaagaa aatctctgcc acgtccatct tctttgaatc tatgccctac     540
aaggtgaacc cagatactgg ctacatcaac tatgaccagc tggaggagaa cgcacgcctc     600
ttccacccga agctgatcat cgcaggaacc agctgctact cccgaaacct ggaatatgcc     660
cggctacgga agattgcaga tgagaacggg gcgtatctca tggcggacat ggctcacatc     720
agcgggctgg tggcggctgg cgtggtgccc tccccatttg aacactgcca tgtggtgacc     780
accaccactc acaagaccct gcgaggctgc cgagctggca tgatcttcta caggaaagga     840
gtgaaagtg tggatcccaa gactggcaaa gagattctgt acaacctgga gtctcttatc     900
aattctgctg tgttccctgg cctgcaggga ggtccccaca ccacgccat tgctggggtt      960
gctgtggcac tgaagcaagc tatgactctg gaatttaaag tttatcaaca ccaggtggtg    1020
gccaactgca gggctctgtc tgaggccctg acggagctgg gctacaaaat agtcacaggt    1080
ggttctgaca ccatttgat ccttgtggat ctccgttcca aaggcacaga tggtggaagg    1140
gctgagaagg tgctagaagc ctgttctatt gcctgcaaca gaacacctg tccaggtgac    1200
agaagcgctc tgcggcccag tggactgcgg ctggggaccc cagcactgac gtcccgtgga    1260
cttttggaaa aagacttcca aaaagtagcc cactttattc acagagggat agagctgacc    1320
ctgcagatcc agagcgacac tggtgtcaga gccaccctga aagagttcaa ggagagactg    1380
gcagggata agtaccaggc ggccgtgcag gctctccggg aggaggttga gagcttcgcc    1440
tctctcttcc ctctgcctgg cctgcctgac ttctaaagga gcgggcccac tctggaccca    1500
cctggcgcca cagaggaagc tgcctgccgg agaccccac ctgagagatg gatgagctgc    1560
tccaaaggga actgttgaca ctcgggccct tgagggggt ttcttttgga cttttttcat    1620
gttttcttca caaatcaaaa tttgtttaag tctcattgtt agtaattct                 1669
```

<210> SEQ ID NO 9
<211> LENGTH: 3112
<212> TYPE: DNA
<213> ORGANISM: Homo sapiens

<400> SEQUENCE: 9

```
gtggaacctc gatattggtg gtgtccatcg tgggcagcgg actaataaag gccatggcgc      60
cagcagaaat cctgaacggg aaggagatct ccgcgcaaat aagggcgaga ctgaaaaatc     120
aagtcactca gttgaaggag caagtacctg gtttcacacc acgcctggca atattacagg     180
ttggcaacag agatgattcc aatctttata taaatgtgaa gctgaaggct gctgaagaga     240
ttgggatcaa agccactcac attaagttac caagaacaac cacagaatct gaggtgatga     300
```

```
agtacattac atctttgaat gaagactcta ctgtacatgg gttcttagtg cagctacctt    360
tagattcaga gaattccatt aacactgaag aagtgatcaa tgctattgca cccgagaagg    420
atgtggatgg attgactagc atcaatgctg ggagacttgc tagaggtgac ctcaatgact    480
gtttcattcc ttgtacgcct aagggatgct tggaactcat caaagagaca ggggtgccga    540
ttgccggaag gcatgctgtg gtggttgggc gcagtaaaat agttggggcc ccgatgcatg    600
acttgcttct gtggaacaat gccacagtga ccacctgcca ctccaagact gcccatctgg    660
atgaggaggt aaataaaggt gacatcctgg tggttgcaac tggtcagcct gaaatggtta    720
aaggggagtg gatcaaacct ggggcaatag tcatcgactg tggaatcaat tatgtcccag    780
atgataaaaa accaaatggg agaaaagttg tgggtgatgt ggcatacgac gaggccaaag    840
agagggcgag cttcatcact cctgttcctg gcggcgtagg gcccatgaca gttgcaatgc    900
tcatgcagag cacagtagag agtgccaagc gtttcctgga gaaatttaag ccaggaaagt    960
ggatgattca gtataacaac cttaacctca agacacctgt tccaagtgac attgatatat   1020
cacgatcttg taaaccgaag cccattggta agctggctcg agaaattggt ctgctgtctg   1080
aagaggtaga attatatggt gaaacaaagg ccaaagttct gctgtcagca ctagaacgcc   1140
tgaagcaccg gcctgatggg aaatacgtgg tggtgactgg aataactcca cacccctgg   1200 gagaagggaa aagcacaact acaatcgggc tagtgcaagc ccttggtgcc catctctacc   1260
agaatgtctt tgcgtgtgtg cgacagcctt ctcagggccc cacctttgga ataaaaggtg   1320
gcgctgcagg aggcggctac tcccaggtca ttcctatgga agagtttaat ctccacctca   1380
caggtgacat ccatgccatc actgcagcta ataacctcgt tgctgcggcc attgatgctc   1440
ggatatttca tgaactgacc cagacagaca aggctctctt taatcgtttg gtgccatcag   1500
taaatggagt gagaaggttc tctgacatcc aaatccgaag gttaaagaga ctaggcattg   1560
aaaagactga ccctaccaca ctgacagatg aagagataaa cagatttgca agattggaca   1620
ttgatccaga aaccataact tggcaaagag tgttggatac caatgataga ttcctgagga   1680
agatcacgat tggacaggct ccaacggaga agggtcacac acggacggcc cagtttgata   1740
tctctgtggc cagtgaaatt atggctgtcc tggctctcac cacttctcta gaagacatga   1800
gagagagact gggcaaaatg gtggtggcat ccagtaagaa aggagagccc gtcagtgccg   1860
aagatctggg ggtgagtggt gcactgacag tgcttatgaa ggacgcaatc aagcccaatc   1920
tcatgcagac actggagggc actccagtgt tgtccatgc tggcccgttt gccaacatcg   1980
cacatggcaa ttcctccatc attgcagacc ggatcgcact caagcttgtt ggcccagaag   2040
ggtttgtagt gacggaagca ggatttggag cagacattgg aatggaaaag tttttttaaca   2100 tcaaatgccg gtattccggc ctctgccccc acgtggtggt gcttgttgcc actgtcaggg   2160
ctctcaagat gcacgggggc ggccccacgg tcactgctgg actgcctctt cccaaggctt   2220
acatacagga gaacctggag ctggttgaaa aaggcttcag taacttgaag aaacaaattg   2280
aaaatgccag aatgtttgga attccagtag tagtggccgt gaatgcattc aagacggata   2340
cagagtctga gctggacctc atcagccgcc tttccagaga acatgggct tttgatgccg   2400 tgaagtgcac tcactgggca gaaggggca agggtgcctt agccctggct caggccgtcc   2460
agagagcagc acaagcaccc agcagcttcc agctcctttta tgacctcaag ctcccagttg   2520
aggataaaat caggatcatt gcacagaaga tctatggagc agatgacatt gaattacttc   2580
ccgaagctca acacaaagct gaagtctaca cgaagcaggg cttttgggaat ctccccatct   2640 gcatggctaa aacacacttg tctttgtctc acaacccaga gcaaaaaggt gtccctacag   2700
```

```
gcttcattct gcccattcgc gacatccgcg ccagcgttgg ggctggtttt ctgtacccct   2760
tagtaggaac gatgagcaca atgcctggac tccccacccg gccctgtttt tatgatattg   2820
atttggaccc tgaaacagaa caggtgaatg gattattcta aacagatcac catccatctt   2880
caagaagcta ctttgaaagt ctggccagtg tctattcagg cccactggga gttaggaagt   2940
ataagtaagc caagagaagt cagcccctgc ccagaagatc tgaaactaat agtaggagtt   3000
tccccagaag tcattttcag ccttaattct catcatgtat aaattaacat aaatcatgca   3060
tgtctgttta ctttagtgac gttccacaga ataaaaggaa acaagtttgc ca           3112

<210> SEQ ID NO 10
<211> LENGTH: 1792
<212> TYPE: DNA
<213> ORGANISM: Homo sapiens

<400> SEQUENCE: 10
cgcagcccag actcagactg gggaagcaaa caggggctgg acaggccagg agagcctgtc     60
ggacagtgat cctgagatgt gggagttgct gcagagggag aaggacaggc agtgtcgtgg    120
cctggagctc attgcctcag agaacttctg cagccgagct gcgctggagg ccctggggtc    180
ctgtctgaac aacaagtact cggagggtta tcctggcaag agatactatg ggggagcaga    240
ggtggtggat gaaattgagc tgctgtgcca gcgccgggcc ttggaagcct ttgacctgga    300
tcctgcacag tggggagtca atgtccagcc ctactccggg tccccagcca acctggccgt    360
ctacacagcc cttctgcaac ctcacgaccg gatcatgggg ctggacctgc ccgatggggg    420
ccatctcacc cacggctaca tgtctgacgt caagcggata tcagccacgt ccatcttctt    480
cgagtctatg ccctataagc tcaaccccaa aactggcctc attgactaca accagctggc    540
actgactgct cgacttttcc ggccacggct catcatagct ggcaccagcg cctatgctcg    600
cctcattgac tacgcccgca tgagagaggt gtgtgatgaa gtcaaagcac acctgctggc    660
agacatggcc cacatcagtg gcctggtggc tgccaaggtg attccctcgc ctttcaagca    720
cgcggacatc gtcaccacca ctactcacaa gactcttcga ggggccaggt cagggctcat    780
cttctaccgg aaaggggtga aggctgtgga ccccaagact ggccgggaga tcctttacac    840
atttgaggac cgaatcaact tgccgtgtt cccatccctt caggggggcc cccacaatca    900
tgccattgct gcagtagctg tggccctaaa gcaggcctgc accccatgt tccgggagta    960 ctccctgcag gttctgaaga atgctcgggc catggcagat gccctgctag agcgaggcta   1020
ctcactggta tcaggtggta ctgacaacca cctggtgctg gtggacctgc ggcccaaggg   1080
cctggatgga gctcgggctg agcgggtgct agagcttgta tccatcactg ccaacaagaa   1140
cacctgtcct ggagaccgaa gtgccatcac accgggcggc ctgcggcttg ggccccagc   1200 cttaacttct cgacagttcc gtgaggatga cttccggaga gttgtggact ttatagatga   1260
aggggtcaac attggcttag aggtgaagag caagactgcc aagctccagg atttcaaatc   1320
cttcctgctt aaggactcag aaacaagtca gcgtctggcc aacctcaggc aacgggtgga   1380
gcagtttgcc agggccttcc ccatgcctgg ttttgatgag cattgaaggc acctgggaaa   1440
tgaggcccac agactcaaag ttactctcct tcccctacc tgggccagtg aaatagaaag   1500
cctttctatt ttttggtgcg ggagggaaga cctctcactt agggcaagag ccaggtatag   1560
tctcccttcc cagaatttgt aactgagaag atcttttctt tttccttttt ttggtaacaa   1620
gacttagaag gagggcccag gcactttctg tttgaacccc tgtcatgatc acagtgtcag   1680
agacgcgtcc tctttcttgg ggaagttgag gagtgccctc cagagccagt agcaggcagg   1740
```

-continued ggtgggtagg cacccteectt cctgttttta tctaataaaa tgctaacctg ca        1792

<210> SEQ ID NO 11
<211> LENGTH: 18596
<212> TYPE: DNA
<213> ORGANISM: Homo sapiens

<400> SEQUENCE: 11
cctgtagtcc cagctacgcg agaggctgag gcagcagaat tacttgaacc caggaggcgg        60
aggttgcagt gagccgagat cgcgccactg cactccagcc tgggtgagag agcgagactc       120
tgtctcaaaa aaaaaaaaaa aagaccgcca gggctcaaac aaaaaacctc ggaaaagccc       180
tggcggtctt ttttttttt tttttttttt tttttggga cagtcttgct ctgtcgccca       240
ggctggagta caatggtcgg atcttggctc actgcaacct ctgcctccca ggttcaagca       300
attcttctgc ctcagcctcc caagtagcca ccacgcccag ctaatttttg tacttttagt       360
agagacgggg gtttcaccat gttgtccagg ctggtcttga actcctgacc tcaggtgatc       420
cacccgcctc ggcccccaa agtactagga ttacaggcgt gagccaccgc gtccagcgcc       480
ctggcggttt ttaatcaagt agaaaagctg cattatacca cttgcttcgg ttgcttcagt       540
gagaacgaag aaatggaaat gcaaatccct tattagttgt aggaaacaga tctcaaacag       600
cagttttgtt gacaagaccg caggaaaacg tgggaactgt gctgctggct tagagaaggc       660
gcggtcgacc agacggttcc caaagggcgc agtccttccc agccaccgca cctgcatcca       720
ggttcccggg tttcctaaga ctctcagctg tggccctggg ctccgttctg tgccacaccc       780
gtggctcctg cgtttccccc tggcgcacgc tctctagagc gggggccgcc gcgacccgc       840
cgagcaggaa gaggcggagc gcgggacggc cgcgggaaaa ggcgcgcgga agggtcctg       900
ccaccgcgcc acttggcctg cctccgtccc gccgcgccac ttggcctgcc tccgtcccgc       960
cgcgccactt cgcctgcctc cgtccccgc ccgccgcgcc atgcctgtgg ccggctcgga      1020
gctgccgcgc cggcccttgc ccccgccgc acaggagcgg gacgccgagc cgcgtccgcc      1080
gcacggggag ctgcagtacc tggggcagat ccaacacatc ctccgctgcg gcgtcaggaa      1140
ggacgaccgc acgggcaccg gcaccctgtc ggtattcggc atgcaggcgc gctacagcct      1200
gagaggtgac gccgcgggcc cctgcgggac gggtggcggg aaggaggag gcgcggctgg      1260
ggagagcgct cgggagctgc cgggcgctgc ggaccccgtt tagtcctaac ctcaatcctg      1320
ccagggaggg gacgcatcgt cctcctcgcc ttacagacgc cgaaacggag ggtcccatta      1380
gggacgtgac tggcgcgggc aacacacaca gcagcgacag ccgggaggta agccgcgtcc      1440
cagcggctcc gcggccgggc tcgcagtcgc cccagtgatg ccgtggcccc cgaggcgggc      1500
gtcatcgggc agcgtttgcc cagtgctgga gggttaggga gagctgcctg gcttgaccg      1560
cgcgccggtc tcaaagtcct ggctttggcc cctcctccgt tttccctgt ggaccattcc      1620
gcttcgcagc gttttcaaaa actgagcga aagtgatgtg ggcggggcaa aggcggcggg      1680
aagaggacag cactgaagct ggcgcgggaa cttggtttcc tggtggcctc ccatccaatc      1740
cccacgaacc agctttcctc ttaaaccttg aaaagagaaa ttcgggagtt cgagttctta      1800
gtcgtccttt cctctttcct ttccgacagg agcaccccag gcaaaaaatg tctcgcgggt      1860
cattggcgcc aggctttcag gggacagtgg ggcggggcgg ggtgggcaca ggacgttagg      1920
cagccgttgg ccctccctaa ggccacaccg tcctgccgtc ctggatcctg cgccagctgc      1980
gcggggagg ggactcgaag gtgtgtgagc caggggctga ccttgaccgc tcagataaat      2040
ggagcgcagc cttgacacag gggtggaggt ggttttgaat ggggaaaccc attcgtggtg      2100

```
aagcagattc actgtagcta gcggaaaagc cctccggccc acggacccat ctagagacga    2160
atacatagca gctgctgtgg ctgattggcg tgggacagcg tggggagttt tgtctgagga    2220
gagggatcca cttttctgca gctccaagcc caggggcctt tgatgagcca tagacctcat    2280
ttttaaccca cctttctgct tagacattga gcaagttact tctcatatag cttccctata    2340
tgttaaaaat ggagaaaata atgcttagta ggcaattctg ataaaagcag gtgcttgcaa    2400
aaatctctct gttgtctgaa tataaactgt accacaagcg agtgcggatg aacgaggact    2460
gcatttaaag ataagttttt acactttcat ttctctgtgg ctcgacactt ctgatgcctc    2520
cctttttgtt cctgggacac atgcttggtg ttgtcttcac acctttgtga caggattagc    2580
actagtgggc agtggatgat agctcctcct cccttttgcc acatgttcat ccctgccctc    2640
gccaccatct cactgtgtgg aattcctgtg tccactggtc accggggcac agaagtgctg    2700
tctcagcctg aatcgggcca ctgatgggac ttgcagcctg ggagctccac cgtgatctct    2760
ggcccacttt gcgggagtct aggctttctg gatgctccag gcctcacgtc cagggcagt    2820 tttcttccct gaagaaagtt ggatggcatg atctgtcttc ccatcttgaa accgtatggc    2880
aaattgtttt tcagatgaat tccctctgct gacaaccaaa cgtgtgttct ggaagggtgt    2940
tttggaggag ttgctgtggt ttatcaaggt aaagaagtcg ctgctattag aagtcagtag    3000
tctgttctca acacagcagc cagtgagatc ctttcaaaac tcaaagcagc caggtgtggt    3060
ggctcacgcc tgtaatccca ccgctttggg aggctgagtc agatcacctg aggttaggaa    3120
tttgggacca gcctggccaa catggcgaca ccccagtctc tactaataac acaaaaaatt    3180
agccaggtgt gctggtgcat gtctgtaatc ccagctactc aggaggctga ggcatgagaa    3240
ttgctcacga gcggaggtt gtagtgagct gagatcgtgg cactgtactc cagcctggcg    3300
acagagggag aacccatgtc aaaaacaaaa aaagacacca ccaaaggtca aagcatatca    3360
ttcctcaccc tcaagccctt agtggctcca tttcactcag taagagccac ggtccttatg    3420
gtgtccgttt ttcagctctg accttagctg ctgctctctg caccaccctg ctgttcttgt    3480 gagttttga gcacaccggg acatccccac tccctggaac cttcttcccc cacacttggc    3540
ttcttccttt gagtctctac tccactcggg caagccttcc tagacctcct gatttaaaac    3600
tgtgactctc ccccaacctc cttggtgttt ctccgtagac gaacatcacc atctgatgta    3660
tgtcagcctt tcccttcccc tgttagaagg gggacagcag gtagtaaaag tgaaatgtgc    3720
tgtaagcttt atgagggcag aggatttgtt tctcgtgttc actgttgtat cgccagggcc    3780
tcaaacacag cctgccacat agtaggagtc aacatatatt gatcactaaa tgtagatacc    3840
acctgtgttc ccatgttcat ataaattcta gaagagtctc ttcagtaaca aggtgaaccc    3900
cttccagagg gctgagtagg tacctcaggc cggggccaga gtgctgtgaa gacagcagca    3960
gcccagacca agcttctctg tgttccgtgt cctggtctag aaccagcgat gttctttctg    4020
accagtgctt tttggaaggt ggctgaggtc tgggctcagg tctgggccat actagaagct    4080
gggatccctt ctatagagca cttggtatgg cttgtatggt cttgggcaa gccagaccca    4140 agccctctta tcccatttta gaaagggctt caatttggat ccagcccag gtctgcctta    4200 gctctgtatt cttggggtat tttgttctgt attggcctat cttgactaac aatgagcctt    4260
ggatttgaaa catatcatca gaaacctcag aagcaacat tcttaaactg gctagagcct    4320
ggtctgaatg gatgaaaagg agagactttt gaagcaatat gtaaagatt gagaaatgat    4380 ttgttggaaa tttctcaatt ggagaaattt ctttgatttg ttggaaattt ctttgattct    4440
ttctcaatca aagaaaatcg ggacaaactc aacaatagaa agggaggaag caagatactc    4500
```

```
agaaataaaa tgcattcccc tgtttcaact taatgcttca attcaggatt ctaaggaatc    4560
cttgccagga atgtcagact caccttgata gttggagtta ctccattggt gactcgatca    4620
aatacaggag ttgaggcacc tgcactgtaa aatactgatt agtctgatca ttaggaatat    4680
cctgtatgcc aggtagaaga tacattgaac agattgcatg taggcattaa attcattttg    4740
gggtattaca tatagacaac acatttcatt aagaaacata aaactgtcag atcggtggaa    4800
tacttaaaag cacttggagg tgtttagcct aaaaagctta gttgagggga atggaagaaa    4860
agatctggga gggtggttcc aaagaaggga tcagactatc ctaaagccct caggaatctg    4920
ggctgggacc acctacttaa agataggatg ggcagctggg tgtggtggct cacgcctgta    4980
atcccagcac ttcgggaggc cgaagcgggc ggatcacctg aggtcaggag ttcgaggcca    5040
gcctgaccaa catggagaaa cgctgtctct actaaaaata caaaattagc tgggtgtagt    5100
ggcgcatgcc tgtaatccca gctactcggg aggctgaggc aggggaatcg cttgaacctg    5160
ggaggtggag ggtgccgtga gccacgatcg cgccattgca ctccagcctg gcaacaaga    5220 gcgaaactct caaaaaacaa aaaaaggat gggttccata tgggtggtgt caagtgccca    5280
cctcctagca agtcagcagg ggccagaggc ccttgtaagt ggtgtctcgg ggggatcaac    5340
tgagatggct taagatttac ctggatgcct gctctgctct ccccatctct tccagggatc    5400
cacaaatgct aaagagctgt cttccaaggg agtgaaaatc tgggatgcca atggatcccg    5460
agactttttg gacagcctgg gattctccac cagagaagaa ggggacttgg gcccagttta    5520
tggcttccag tggaggcatt tgggggcaga atacagagat atggaatcag gtgaggagat    5580
agaacaatgc cttccatttc cgggtgccct tcctagcacg tgtttgctcc gttgttttag    5640
ataaggtctg ggggatgagt caatgtcaca ggagctgatg tatagctttg accttgtgag    5700
gggtggtgcc aggttgaagc cacaattaac gcctactgaa ggccgtttca catcttttt    5760 tttttttttt ttttaattat tatactttaa gttttagggt acatgtgcac aatgtgcagg    5820
ttagttacat atgtatacat gtgccatgct ggtgcgctgc accactaact caccatctag    5880
catcaggtat atctcccaat gctatccctc cccctcctc ccaccccaca acatccccag    5940
agtgtgatgt tccccttcct gtgtccatat gttctcgttg ttcgattccc actatgagtg    6000
agaatatgcg gtgtttggtt ttttgttctt gcgatagttt actgagaatg atgatttcca    6060
tttcaccacg tccctacaga ggacatgaac tcatcatttt ttatggctgc atagtattcc    6120
atggtgtata tgtgccacat tttcttaatc cagtctatca tgttggacat ttgggttggt    6180
tccaagtctt tgcctattgt gaatagtgcc acaataaaca tacgtgtgca tgtgtcttta    6240
tagcagcatg atttaatagt cctttgggta tatacccagt aatgggatgg ctgggtcaaa    6300
tggtatttct agttctagat ccccgaggaa tcgccacact gacttccaca atggttgaac    6360
tagtttacag tcccaccaac agtgtcaaag tgtcctattt ctccacatcc tctccagcac    6420
ctgttgtttc ctgacttttt aatgattgcc attctaactg gtgtgagatg gtatctcatt    6480
gtggttttga tttgcgtttc tctgatggcc agtgatggtg agcatttttt catgtgtttt    6540
ttggctgcat aaatgtcttc ttttgagaag tgtctgttca tgtccttcgc ccactttttg    6600
atggggttgt ttttttctta taaatttgtt tgagttcatt gtagattctg gatattagcc    6660
ctttgtcaga tgagtaggtt gcaaaaatgt ctcccatttt tgtgggttgc ctgttcactc    6720
tgatggtagt ttcttttgct gtgcagaagc tctttagttt aattagatcc catttgtcaa    6780
ttttggcttt tgttgccatt gcttttggca taggcatgaa gtccttgccc atgcctatgt    6840
cctgaatggt aatgcctagg ttttcttcta gggttttat ggtttaggt ctaacgttta    6900
```

```
agtctttaat ccatcttgaa ttgattttg tataaggtgt aaggaaggga tccagtttca    6960
gcttttaca tatggctagc cagttttccc agcaccattt attacatagg gaatcctttc    7020
cccattgctt gttttctca ggtttgtcaa agatcagata gttgtagata tgcggcgtta    7080
tttctgaggg ctctgttctg ttccattgat ctatgtgtct gttttggtac cagtaccata    7140
ctgttttggt tactgtagcc ttgtagtata gtttgaagtc aggtagcgtg atgcctccag    7200
ctttgttctt ttggcttagg attgacttgg cgatgcgggc tcttttttgg ttccatatga    7260
actttaaagt agttttttcc aattctgtga agaaagtcat tggtagcttg atggggatgg    7320
cattgaatct ataaattacc ttgggcagta tggccatttt cacgatattg attcttccta    7380
cccatgagca tggaatggtc ttccatttct ttgtatcctc ttttatttca ttgagcagtg    7440
gtttgtagtt ctccttgaag aggtccttca catcccttt aaggtggatt cctaggtatt    7500
ttattctctt tgaagcaatt gtgagtggaa gttcactcat gatttggctc tctgtttgtc    7560
tgttattggt gtataagaat gcttgtgatt tttgcagatt gattttatat cctgagactt    7620
tgctgaagct gcttatcagc ttaaggagat tttgggctga gacaatgggg ttttctagat    7680
atacaatcat gtcgtctgca aacagggaca atttgacttc ctcttttcct aattgaatac    7740
cctttatttc cttctcctgc ctaattgccc tggccagaac ttccaacact atgttgaata    7800
ggagtggtga gagagggcat ccctgtcttg tgccagtttt caaagggaat gcttccagtt    7860
tttgcccatt cactatgata ttggctgtgg ctttgtcata gatagctctt attattttga    7920
aatatgttcc atcaatacct aatttattga gagttttag catgatgtgt tgttgaattt    7980
tgtcaaaggc ttttctgca tctattgaga taatcatgtg gttttgtct ttggatctgt    8040
ttatatgctg gattacattt attgatttgc gtatattgaa ccagccttgc atcctaggga    8100
tgaagcccac atgatcatgg tggataagct ttttgatgtg ctgctggatt cggtttgcca    8160
gtatttatt gaggattttt gcatcaatgt tcatcaagga tattggtcta aaattctctt    8220
ttttggtgtg tctctgccca gctttggtat caggatgatg ttggcttcat aaaatgagtt    8280
agggaggatt ccctcttttt ctattgattg gaatagtttc agaaggaatg gtaccagttc    8340
ctctttgtac ctctggagaa ttcggctgtg aatccatctg gtcctggact ctctttggtt    8400
ggtaagctat tgattattgc cacaatttca gctcctgtta ttggtctatt cagagattca    8460
acttcttcct ggtttagtct tgggagagtg tatgtgtcaa ggaatttatc catttcttct    8520
agatttccta gtttatttgc gtagaggtgt ttgtagtaat ctctgatggt agtttgtatt    8580
tctgtgggat cggtggtgat atccccttta tcattttta ttgcgtctat ttgattcttc    8640
tctttttctt tattagtctt gctagcggtc tataaattt gttgatcctt tcaaaaaacc    8700
agctcctgga ttcattaatt ttttgaaggg ttttttgtgt ctctatttcc ttcagttctg    8760
ctctgatttt agttatttct tgccttctgc tagcttttga atatgtttgc tcttgctttt    8820
ctagttcttt taattgtgat gttagggtgt caatttggga tctttcctgc tttctcttgt    8880
gggcatttag tgctataaat ttccctctac acactgcttt gaatgtgtcc cagaggttct    8940
ggtatgttgt gtctttgttc ttgttggttt caaagaacat ctttatttct gccttcattt    9000
cgttatgtac ccagtagtca ttcaggagca ggttgttcag tttccatgta gttgagcagt    9060
tttgagtgag attcttaatc ctgagttcta gtttgattgc actgtggtct gagagatagt    9120
ttgttataat ttctgttctt ttacatttgc tgaggagagc tttacttcca actatgtggt    9180
cggttttgga ataggtgtgg tgtggtgctg aaaaaaatgt atattctgtt gatttgggat    9240
ggagttctgt agatgtctat taggtctgct tggtgcagag ctgagttcaa ttcctgggta    9300
```

```
tccttgttga ctttctgtct cgttgatctg tgtactgttg acagtgggtg ttaaagtctc   9360
ccattattaa tgtgtggagt ctaagtctct ttgtaggtca ctcagatgat tggcacttac   9420
tgggcgcttg gcactttcca tactgtgtca tcggcagata gctgcatggt tggtgttcgt   9480
gctggggaat gggaagttca tcggtgggac aaggacaaaa tgcccccatt gctttgttgt   9540
ggctttaatc tcccttttcga ggctgagcca cagcgtgctg taggtggcgc tgctgtgaag   9600
cgcagtacca gggtcacact ccactcccag ctctgcagag gtggagaaag aatgaaacat   9660
ctcactcctg gacttccact ttcctgtcac tgttggtgtc acctcttact ggatgtcaca   9720
gagcccagcc cctcccacct gtgcctagga aaagcagatg ccaccttgga atgtgggatt   9780
tgtgtgtgca atttactagc tgggcagaga ccagcaacct ggagagcagg tgtctcgtct   9840
aaggggacag tcacatttca cctccagcca cctggaggaa tttgggcctg gtgatgtcag   9900
aattcttcaa taaaagccta aaatctatat tttatgtgcg gtcatgagat ctgttaaatg   9960
ttagcaactt caggaagttt aaaaatgctg tgtggaccta gaataggcaa gttcttaaag  10020
gcagaaagtg gaatgctagt ttccagggac tggggaacag ggaggaatgg ggagttcatg  10080
tttaatgggc acagaggttt tgttaggat gacgaaaaag ttcggagat ggtgatggtg  10140 atggagatgg tgatggtgat ggagatggtg atggtgatgg tgatgtgat gggtgatggt  10200 gatggtgatg gtgatggtga tggagatggt gatggtgatg gtgatggaga tggtgatggt  10260
gatggtgatg gtgatggaga tggtgatggt gatggagatg gtgatggtga tggtgatgga  10320
gatggtgatg gtgatggtga tggtgatggt gatggtgatg gtgatggaga tggagatggt  10380
gatggtgatg gttgcctaac atcaggaacg tgcttaatgc ttctgaattg cacacaaaaa  10440
tggcaagttt aatattatgt gtactttatc acaatgaaaa aagctgctgc gtgggccaag  10500
ttacttgtgc aggtaatgtt ctgcaggtgg ttgcctgcac ctcagttgta gggtgtccgt  10560
aggatgtgag gccagtcccc gggcttaatg atgctttaaa tcctgcctag tattcaatta  10620
tttcttgtcg cttaaaaggc ctaataaaat tatggtctta gtttacagtg gtatgaatgc  10680
ttagctgttg gattttagta ggaaagttcg tcccttttg ttttttaattt tgttttacag  10740 attcacagga attttttttt tttttttttt tttttttttt taatgcacag aaagtttccc  10800
tggactctct acccagtttc cccagtgata atatcttggg taacatcctg tatacattca  10860
cattggtgca ttcctcagag ttgtcagatt ttgctagttt tacgtgcact tgtgtatgtg  10920
tgtatttgca attttagcac gtgtagactc ttgtaaccac tacaatcaag ttacagaact  10980
acactaccaa ggttcatctt tttaaaatct ttgatgttac cttttttgga acagtgacca  11040
tgagaggact ttcctcccaa aattttgaaa actactgaac cagaatatag tctgacacta  11100
ataggtagaa atttaaccaa aggagattat gaagctctgc acttgagtta acaaaatcac  11160
ttctcagctt ccagttccat ctcagaagga aggaaaaggg attaaaaatc cagagaccag  11220
aaaatgggag caaagtacaa ggtggtgtaa tcattacaga ggtttcctga tgtttccaag  11280
tcagtcgtgt gttgagctgc taaactctaa agtaattta ggtggaatgt tggaaacatg  11340
ctgctgaggt gatagaaagg aatccatggt cctctgttag ttggaaagta tatgaatac  11400 tatattctac ataagataca atactctctg tgagacaagg ataaagtaga ttttgtcagt  11460
gaaattgtga caagaatcgc tgatgggttt agagcctaag tttgcgagga gcactggaag  11520
aaattaagat tgttgagatt ggaaagggtt agctatgggg gaacaggagg aggtgactcc  11580 atgcagacc aaatattcaa aggactgtgt agaagaggaa aaagactttg ttagggctcc  11640
agaggacaga gccaggagtc agacagggcc ttgaactcaa cccaccgaga tctgcaaact  11700
```

```
ttgcaggatg caccagatgt cttgtagcca tgggtcaagg ggggaccctg ggtaagagac   11760
tgtaatagat gacctctaag gccatctcat gacatgtgtg attaatgtat gtacctgtcc   11820 tctcttttg acaattctac agattattca ggacagggag ttgaccaact gcaaagagtg    11880
attgacacca tcaaaaccaa ccctgacgac agaagaatca tcatgtgcgc ttggaatcca   11940
agaggttgaa agaaccccgt cgtcttcatt tatactaacc atactcttag agggaagcaa   12000
tctggttttg tgcagaggca ctgagggagg caggaccctg gcaacttcc cccagccaca    12060 tggttgtgtg acgttgggca agtcacattt tgctgcactt tcaccttcag atcatgaggt   12120
tgggcccaga ggatttttt ttttttttt tttttgaga cagagttttg ctctgttgcc      12180
caggctggaa tgcaacggcg tgatcttggc tcactgtaac ctctgcctcc tgggttcgag   12240
tgattctcct gcctcagcct ccaagtagct gggattacag catgtgccac catgcctggc   12300
taattttgta ttttagtag acgggttc acatgttggt caggctggtc ttgactcctg      12360
accctcagat gatctgcctt gcctcagcct cccaaccgag tgatcttaag ttgtgtatta   12420
tactcattct tacacaaaaa gggctttaaa tgcctagaaa ctacatgaag atgttaacat   12480
tttaaatgga agcagatgaa gttccagctc gctgccacct cactaacatt tttaacaatt   12540
atattgtaaa attcaactct accagggtgt agagccaggt gtggtggctc acacctgtaa   12600
ttccaacaac tccagaggcc aaggcgagag gatcatttga acccacggaa tttgaggctg   12660
tagtgagtca tgatcacgcc attgcactcc atcctgggca acagagtgag accctgaata   12720
tttaaaaaca acaacaacaa caaaactcta tcaggatatc ataagtactt agagtgaaat   12780
acttgcatct gtaatagaga cttattttt tttttttga gacacagtct cacctgttg     12840 cccaggctgg agtgcagtgg tttgatctcc gctcacggca acctccatct cccaggttca   12900
agtgagttcc cattcctcag ccccagagct gggaccacag gcgcgcgaat ttttgtattt   12960
ttagcagaga cggggtttca ctatgttggc caggctagtc tcaaactcaa gttggcctca   13020
agtgatctgc ccaccctggc gtcccagtgt tgggatttca ggcatgagcc actgtgcctg   13080
gccatgtaat agagactttt aatataggag ggtgtaccag aagcaccagt ttcctgtggc   13140
aaacagaatt attcctgctg tatttgtaat ttggtgccac gaggtagccc agatcccttc   13200
agctctgatg gaagagcatt gcttcagccg taaatggaca cctgcagaaa ccttgcaccg   13260
atggatagtc tccctcagct ccgtgccatc gctgcagggg ctgttatgga catcactgca   13320
gcccagtggc tctctctcct ggtctccacc atatgagttg gcttctgttt ctctcctgtt   13380
ttactttgcc tttagctgtg gtctttcaaa ccaccatccc tccttatctt cctctgctgg   13440
ttcctcagat cttcctctga tggcgctgcc tccatgccat gccctctgcc agttctatgt   13500
ggtgaacagt gagctgtcct gccagctgta ccagagatcg ggagacatgg gcctcggtgt   13560
gcctttcaac atcgccagct acgccctgct cacgtacatg attgcgcaca tcacgggcct   13620
gaaggtgggc tgtctcggga agggtgactt gccagcctac cacatgagct cttcagttct   13680
ttaatatggg aaaacaaatt gcagagttta gtctctgatt agcttttaaa tttgatatgt   13740
gtaagtaaga catgaaccag cttttacttt gaaaccttcc ttttctggaa ggttttctgg   13800
ccctgtggta tatgcactaa cagatctata caggttgttt gtgatacagc ttctatggat   13860
cttctcaaaa gctatgctga ggttgggtat ggtggctcat gcctgtaatc ccagcacttt   13920
ggaagactga gacaggagca attgcttgag gtctggagtt caataccagc ctgggcaaca   13980
taacaagatg ctgttgctac aaaaaaatgg aaaagctaca ctaaattatt tttttaaaaa   14040
aagccttgcg gtgtctgcat attctaatgt ttttaaatga tgttttaaag aattgaaact   14100
```

```
aacatactgt tctgctttct cccggtttat agccaggtga ctttatacac actttgggag   14160
atgcacatat ttacctgaat cacatcgagc cactgaaaat tcaggtaaga attagatgtt   14220
atacttttgg gtttggtacc ttctcttgat aaaaggttga ctgtggaaca ggtatctgct   14280
caatgctgtg tccaagataa agatgactgc tccaaatgtg gggcttcagt ttagggagaa   14340
gtggtgggca ggtgggcagg acaaggcagg catctgcctc agcaaccatg gcacttaact   14400
tgtcaggtgc tgtgaggtac taagcaccag taccagagag ggaagagcca cattcaagcc   14460
aggggattgt ccaaaaggag gcattttaac tcattttaac ttgaaggaga attgaagtgc   14520
aaatgttttt cctttctttt tttttgaga tggagtcttt ctctgtcggc caggctggag    14580
tgtgccgtgg tgcgatctca gctcactgca acctccacct cccgggttca agcaattctt   14640
ctgcctcagc ctcccaggta gctgggatta caggcacatg ccaccacacc cagctaattt   14700
tttgtattat tagtagagat ggggtttcgt catgttggcc aggctgatct caaactcctg   14760
acttcaagtg taccacctgc ctcagcctcc gaaagttctg gaattacagg cataagccac   14820
caccctggcc ataaatattt tttgttaatt ttacattaag tacaatattt aggtccaaac   14880
ttcaaaagtc tgttgaaatc cctgaagtta tagcagccaa caattgatat gaaatggcaa   14940
taaaaatgta agttcatctg cttcatgagc cttaaggaaa aaaactcaga accagacact   15000
ttttagcccc ttccaggtta gatccaggtt ttaaaagtta ttcctttgag ggagtttggc   15060
tgcttttgag tggaggtgac ttcaggctta ttctctctgg ctctctgctc tggtcatttt   15120
tagacatagt aataggttgt gacctgtctt cacatcctaa ttgccactgt ctgttcatcc   15180
caggaatcct ggctttcatc cctttctgtt cactgtccat gcatgtcatc tttccttctt   15240
tctgccaggg accagatggg ttagggattg tgaattcaag taaacgtaga gctactatga   15300
gttacagatt gactgtgttc ctgtctttaa taaatttgcc aagagtggtt ataagaactt   15360
acacctgatg aggcaccagg ctcctgatgc tgtgtaatgt cacaaaatac ccctcactct   15420
cgatctgtgc aagagaacag ctggttgcgc tccaatcatg ttacataacc tacgcgaagg   15480
tatcgacagg atcatactcc tgtaaaatag aactttgttg atcacatcct gtgtacttgt   15540
ttcacggaca tgaggagcaa ttacaacagg tcgtacaatt atggcaaaat aatggcctta   15600
ttttgttttt agcttcagcg agaacccaga ccttttcccaa agctcaggat tcttcgaaaa   15660
gttgagaaaa ttgatgactt caaagctgaa gactttcaga ttgaagggta caatccgcat   15720
ccaactatta aaatggaaat ggctgtttag ggtgctttca aaggagctcg aaggatattg   15780
tcagtcttta gggggttgggc tggatgccga ggtaaaagtt cttttttgctc taaaagaaaa  15840 aggaactagg tcaaaaatct gtccgtgacc tatcagttat taatttttaa ggatgttgcc   15900
actggcaaat gtaactgtgc cagttctttc cataataaaa ggctttgagt taactcactg   15960
agggtatctg acaatgctga ggttatgaac aaagtgagga gaatgaaatg tatgtgctct   16020
tagcaaaaac atgtatgtgc atttcaatcc cacgtactta aaagaaggt tggtgaattt    16080 cacaagctat ttttggaata tttttagaat attttaagaa tttcacaagc tattccctca   16140
aatctgaggg agctgagtaa caccatcgat catgatgtag agtgtggtta tgaactttaa   16200
agttatagtt gttttatatg ttgctataat aaagaagtgt tctgcattcg tccacgcttt   16260
gttcattctg tactgccact tatctgctca gttccttcct aaaatagatt aaagaactct   16320
ccttaagtaa acatgtgctg tattctggtt tggatgctac ttaaaagagt atattttaga   16380
aataatagtg aatatatttt gccctatttt tctcatttta actgcatctt atcctcaaaa   16440
tataatgacc atttaggata gagttttttt tttttttttt taaactttta taaccttaaa   16500
```

```
gggttatttt aaaataatct atggactacc attttgccct cattagcttc agcatggtgt      16560
gacttctcta ataatatgct tagattaagc aaggaaaaga tgcaaaacca cttcgggggtt    16620 aatcagtgaa atatttttcc cttcgttgca taccagatac ccccggtgtt gcacgactat     16680
ttttattctg ctaatttatg acaagtgtta aacagaacaa ggaattattc caacaagtta     16740
tgcaacatgt tgcttatttt caaattacag tttaatgtct aggtgccagc ccttgatata     16800 gctattttg taagaacatc ctcctggact ttgggttagt taaatctaaa cttatttaag      16860
gattaagtag gataacgtgc attgatttgc taaaagaatc aagtaataat tacttagctg     16920
attcctgagg gtggtatgac ttctagctga actcatcttg atcggtagga ttttttaaat     16980 ccattttgt aaaactattt ccaagaaatt ttaagccctt tcacttcaga aagaaaaaag      17040
ttgttggggc tgagcactta attttcttga gcaggaagga gtttcttcca aacttcacca    17100
tctggagact ggtgtttctt tacagattcc tccttcattt ctgttgagta gccgggatcc    17160
tatcaaagac caaaaaatg agtcctgtta acaaccacct ggaacaaaaa cagattttat     17220
gcatttatgc tgctccaaga aatgctttta cgtctaagcc agaggcaatt aattaatttt    17280 ttttttttg acatggagtc actgtccgtt gcccaggctg cagtgcagtg gcgcaatctt     17340
ggctcactgc aacctccacc tcccaggttc aagtgattct cctgcctcag cctcccatgt    17400
agctgggatc acaggcacct gccaccatgc ccggctaatt ttttgtattt tttgtagaga    17460
cagggtttca ccatgttggc caggctggtc tcaaacacct gaccctcaaat gatccacctg    17520 cctcagcctc ccaaagtgtt gggattacag gcgtaagcca ccatgcccag ccctgaatta    17580
atatttttaa aataagtttg gagactgttg gaaataatag ggcagaggaa catatttac    17640 tggctacttg ccagagttag ttaactcatc aaactctttg ataatagttt gacctctgtt   17700
ggtgaaaatg agccatgatc tcttgaacat gatcagaata aatgccccag ccacacaatt  17760
gtagtccaaa cttttaggt cactaacttg ctagatggtg ccaggttttt ttgcacaagg   17820
agtgcaaatg ttaagatctc cactagtgag gaaaggctag tattacagaa gccttgtcag  17880
aggcaattga acctccaagc cctggcctc aggcctgagg attttgatac agacaaactg   17940
aagaaccgtt tgttagtgga tattgcaaac aaacaggagt caaagcttgg tgctccacag  18000
tctagttcac gagacaggcg tggcagtggc tggcagcatc tcttctcaca ggggccctca   18060
ggcacagctt accttgggag gcatgtagga agcccgctgg atcatcacgg gatacttgaa  18120
atgctcatgc aggtggtcaa catactcaca caccctagga ggagggaatc agatcggggc  18180
aatgatgcct gaagtcagat tattcacgtg gtgctaactt aaagcagaag gagcgagtac   18240
cactcaattg acagtgttgg ccaaggctta gctgtgttac catgcgtttc taggcaagtc   18300
cctaaacctc tgtgcctcag gtccttttct tctaaaatat agcaatgtga ggtgggggact  18360 ttgatgacat gaacacacga agtccctctg agaggttttg tggtgccctt taaaagggat   18420
caattcagac tctgtaaata tccagaatta tttgggttcc tctggtcaaa agtcagatga  18480
atagattaaa atcaccacat tttgtgatct attttttcaag aagcgtttgt atttttttcat 18540 atggctgcag cagctgccag gggcttgggg ttttttttggc aggtagggtt gggagg       18596
```

<210> SEQ ID NO 12
<211> LENGTH: 3291
<212> TYPE: DNA
<213> ORGANISM: Homo sapiens

<400> SEQUENCE: 12

```
accgggcaag cgggaaccag gtggccaccc ggtgtcggtt tcattttcct ttggaatttc    60
```

```
tgctttacag acagaacaat ggcagcccga gtacttataa ttggcagtgg aggaagggaa      120
catacgctgg cctggaaact tgcacagtct catcatgtca aacaagtgtt ggttgcccca      180
ggaaacgcag gcactgcctg ctctgaaaag atttcaaata ccgccatctc aatcagtgac      240
cacactgccc ttgctcaatt ctgcaaagag aagaaaattg aatttgtagt tgttggacca      300
gaagcacctc tggctgctgg gattgttggg aacctgaggt ctgcaggagt gcaatgcttt      360
ggcccaacag cagaagcggc tcagttagag tccagcaaaa ggtttgccaa agagtttatg      420
gacagacatg gaatcccaac cgcacaatgg aaggctttca ccaaacctga gaagcctgc       480 agcttcattt tgagtgcaga cttccctgct ttggttgtga aggccagtgg tcttgcagct      540
ggaaaagggg tgattgttgc aaagagcaaa gaagaggcct gcaaagctgt acaagagatc      600
atgcaggaga aagcctttgg ggcagctgga gaaacaattg tcattgaaga acttcttgac      660
ggagaagagg tgtcgtgtct gtgtttcact gatggcaaga ctgtggcccc catgccccca      720
gcacaggacc ataagcgatt actggaggga gatggtggcc taacacaggg ggaatggga      780 gcctattgtc cagcccctca ggtttctaat gatctattac taaaaattaa agatactgtt      840
cttcagagga cagtggatgg catgcagcaa gagggtactc catatacagg tattctctat      900
gctggaataa tgctgaccaa gaatggccca aaagttctag agtttaattg ccgttttggt      960
gatccagagt gccaagtaat cctcccactt cttaaaagtg atctttatga agtgattcag     1020
tccaccttag atggactgct ctgcacatct ctgcctgttt ggctagaaaa ccacaccgcc     1080
ctaactgttg tcatggcaag taaaggttat cctggagact acaccaaggg tgtagagata     1140
acagggtttc ctgaggctca agctctagga ctggaggtgt ccatgcagg cactgccctc     1200 aaaaatggca agtagtaac tcatgggggt agagttcttg cagtcacagc catccgggaa     1260
aatctcatat cagcccttga ggaagccaag aaaggactag ctgctataaa gtttgaggga     1320
gcaatttata ggaaagacgt cggctttcgt gccatagctt tcctccagca gcccaggagt     1380
ttgacttaca aggaatctgg agtagatatc gcagctggaa atatgctggt caagaaaatt     1440 cagccttag caaaagccac ttccagatca ggctgtaaag ttgatcttgg aggttttgct      1500 ggtcttttg atttaaaagc agctggtttc aaagatcccc ttctggcctc tggaacagat     1560
ggcgttggaa ctaaactaaa gattgcccag ctatgcaata acatgatac cattggtcaa     1620 gatttggtag caatgtgtgt taatgatatt ctggcacaag gagcagagcc cctcttcttc     1680
cttgattact tttcctgtgg aaaacttgac ctcagtgtaa ctgaagctgt tgttgctgga     1740
attgctaaag cttgtggaaa agctggatgt gctctccttg gaggtgaaac agcagaaatg     1800
cctgacatgt atccccctgg agagtatgac ctagctgggt tgccgttgg tgccatggag     1860 cgagatcaga aactccctca cctggaaaga atcactgagg gtgatgttgt tgttggaata     1920
gcttcatctg gtcttcatag caatggattt agccttgtga ggaaaatcgt tgcaaaatct     1980
tccctccagt actcctctcc agcacctgat ggttgtggtg accagacttt aggggactta     2040
cttctcacgc ctaccagaat ctacagccat tcactgttac ctgtcctacg ttcaggacat     2100
gtcaaagcct ttgcccatat tactggtgga ggattactag agaacatccc cagagtcctc     2160
cctgagaaac ttggggtaga tttagatgcc cagacctgga ggatccccag ggttttctca     2220
tggttgcagc aggaaggaca cctctctgag gaagagatgg ccagaacatt taactgtggg     2280
gttggcgctg tccttgtggt atcaaaggag cagacagagc agattctgag ggatatccag     2340
cagcacaagg aagaagcctg ggtgattggc agtgtggttg cacgagctga aggttcccca     2400
cgtgtgaaag tcaagaatct gattgaaagc atgcaaaataa atgggtcagt gttgaagaat     2460
```

-continued

| | |
|---|---|
| ggctccctga caaatcattt ctcttttgaa aaaaaaaagg ccagagtggc tgtcttaata | 2520 |
| tctggaacag gatcgaacct gcaagcactt atagacagta ctcgggaacc aaatagctct | 2580 |
| gcacaaattg atattgttat ctccaacaaa gccgcagtag ctgggttaga taaagcggaa | 2640 |
| agagctggta ttcccactag agtaattaat cataaactgt ataaaaatcg tgtagaattt | 2700 |
| gacagtgcaa ttgacctagt ccttgaagag ttctccatag acatagtctg tcttgcagga | 2760 |
| ttcatgagaa ttctttctgg cccctttgtc caaaagtgga atggaaaaat gctcaatatc | 2820 |
| cacccatcct tgctcccttc ttttaagggt tcaaatgccc atgagcaagc cctggaaacc | 2880 |
| ggagtcacag ttactgggtg cactgtacac tttgtagctg aagatgtgga tgctggacag | 2940 |
| attattttgc aagaagctgt tcccgtgaag aggggtgata ctgtcgcaac tctttctgaa | 3000 |
| agagtaaaat tagcagaaca taaaatattt cctgcagccc ttcagctggt ggccagtgga | 3060 |
| actgtacagc ttgagaaaaa tggcaagatc tgtttgggtta agaggaatg aagccttta | 3120 |
| attcagaaat ggggccagtt tagaaagaat tatttgctgt ttgcatggtg gttttttatc | 3180 |
| atggacttgg cccaaaagaa aaactgctaa aagacaaaaa agacctcacc cttacttcat | 3240 |
| ctatttttt aataaataga gactcactaa aaaaaaaaaa aaaaaaaaa a | 3291 |

<210> SEQ ID NO 13
<211> LENGTH: 1776
<212> TYPE: DNA
<213> ORGANISM: Homo sapiens

<400> SEQUENCE: 13

| | |
|---|---|
| atggtgccct ccagcccagc ggtggagaag caggtgcccg tggaacctgg gcctgacccc | 60 |
| gagctccggt cctggcggcg cctcgtgtgc tacctttgct tctacggctt catggcgcag | 120 |
| atacggccag gggagagctt catcaccccc tacctcctgg ggcccgacaa gaacttcacg | 180 |
| cgggacgagg tcacgaacga gatcacgccg gtgctgtcgt actcctacct ggccgtgctg | 240 |
| gtgcccgtgt tcctgctcac cgactacctg cgctacacgc cggtgctgct gctgcagggg | 300 |
| ctcagcttcg tgtcggtgtg gctgctgctg ctgctgggcc actcggtggc gcacatgcag | 360 |
| ctcatggagc tcttctacag cgtcaccatg gccgcgcgca tcgcctattc ctcctacatc | 420 |
| ttctctctcg tgcggcccgc gcgctaccag cgtgtggccg gctactcgcg cgctgcggtg | 480 |
| ctgctgggcg tgttcaccag ctccgtgctg ggccagctgc tggtcactgt gggccgagtc | 540 |
| tccttctcca cgctcaacta catctcgctg gccttcctca ccttcagcgt ggtcctcgcc | 600 |
| ctcttcctga agcgcccaa gcgcagcctc ttcttcaacc gcgacgaccg ggggcggtgc | 660 |
| gaaacctcgg cttcggagct ggagcgcatg aatcctggcc caggcgggaa gctgggacac | 720 |
| gccctgcggg tggcctgtgg ggactcagtg ctggcgcgga tgctgcggga gctggggac | 780 |
| agcctgcggc ggccgcagct gcgcctgtgg tccctctggt gggtcttcaa ctcggccggc | 840 |
| tactacctgt tggtctacta cgtgcacatc ctgtggaacg aggtggaccc caccaccaac | 900 |
| agtgcgcggg tctacaacgg cgcggcagat gctgcctcca cgctgctggg cgccatcacg | 960 |
| tccttcgccg cgggcttcgt gaagatccgc tgggcgcgct ggtccaagct gctcatcgcg | 1020 |
| ggcgtcacgg ccacgcaggc ggggctggtc ttccttctgg cgcacacgcg ccacccgagc | 1080 |
| agcatctggc tgtgctatgc ggccttcgtg ctgttccgcg ctcctaccag gttcctcgtg | 1140 |
| cccatcgcca ccttcagat tgcatcttct ctgtctaaag agctctgtgc cctggtcttc | 1200 |
| ggggtcaaca cgttctttgc caccatcgtc aagaccatca tcactttcat tgtctcggac | 1260 |
| gtgcggggcc tgggcctccc ggtccgcaag cagttccagt tatactccgt gtacttcctg | 1320 |

-continued

| | |
|---|---|
| atcctgtcca tcatctactt cttgggggcc atgctggatg gcctgcgcga ctgccagcgg | 1380 |
| ggccaccacc cgcggcagcc cccggcccag ggcctgagga gtgccgcgga ggagaaggca | 1440 |
| gcacagcgac tgagcgtgca ggacaagggc ctcggaggcc tgcagccagc ccagagcccg | 1500 |
| ccgctttccc cagaagacag cctggggggct gtggggccag cctccctgga gcagagacag | 1560 |
| agcgacccat acctggccca ggccccggcc ccgcaggcag ctgaattcct gagcccagtg | 1620 |
| acaaccccctt ccccctgcac tctgtcgtcc gcccaagcct caggccctga ggctgcagat | 1680 |
| gagacttgtc cccagctggc tgtccatcct cctggtgtca gcaagctggg tttgcagtgt | 1740 |
| cttccaagcg acggtgttca gaatgtgaac cagtga | 1776 |

<210> SEQ ID NO 14
<211> LENGTH: 2500
<212> TYPE: DNA
<213> ORGANISM: Homo sapiens

<400> SEQUENCE: 14

| | |
|---|---|
| tgaatcgccc ggggtcgccg tctccgcctc gccgcagtcg gggcagccgc tgccctcttt | 60 |
| tccatgtatc gtccaggatc ccatgacaga ttctgttgtc acgtctcctt acagagtttg | 120 |
| agcggtgctg aactgtcagc acatctgtcc ggtccagcat gccttctgag acccccagg | 180 |
| cagaagtggg gccacaggc tgcccccacc gctcagggcc acactcggcg aaggggagcc | 240 |
| tggagaaggg gtccccagag gataaggaag ccaaggagcc cctgtggatc cggcccgatg | 300 |
| ctccgagcag gtgcacctgg cagctgggcc ggcctgcctc cgagtcccca catcaccaca | 360 |
| ctgccccggc aaaatctcca aaaatcttgc cagatattct gaagaaaatc ggggacaccc | 420 |
| ctatggtcag aatcaacaag attgggaaga agttcggcct gaagtgtgag ctcttggcca | 480 |
| agtgtgagtt cttcaacgcg ggcgggagcg tgaaggaccg catcagcctg cggatgattg | 540 |
| aggatgctga gcgcgacggg acgctgaagc ccggggacac gattatcgag ccgacatccg | 600 |
| ggaacaccgg gatcgggctg gccctggctg cggcagtgag gggctatcgc tgcatcatcg | 660 |
| tgatgccaga aagatgagc tccgagaagg tggacgtgct gcgggcactg ggggctgaga | 720 |
| ttgtgaggac gcccaccaat gccaggttcg actccccgga gtcacacgtg ggggtggcct | 780 |
| ggcggctgaa gaacgaaatc cccaattctc acatcctaga ccagtaccgc aacgccagca | 840 |
| acccctggc tcactacgac accaccgctg atgagatcct gcagcagtgt gatgggaagc | 900 |
| tggacatgct ggtggcttca gtgggcacgg gcggcaccat cacgggcatt gccaggaagc | 960 |
| tgaaggagaa gtgtcctgga tgcaggatca ttggggtgga tcccgaaggg tccatcctcg | 1020 |
| cagagccgga ggagctgaac cagacggagc agacaaccta cgaggtggaa gggatcggct | 1080 |
| acgacttcat ccccacggtg ctggacagga cggtggtgga caagtggttc aagagcaacg | 1140 |
| atgaggaggc gttcacctt gcccgcatgc tgatcgcgca agaggggctg ctgtgcggtg | 1200 |
| gcagtgctgg cagcacggtg gcggtggccg tgaaggctgc gcaggagctg caggagggcc | 1260 |
| agcgctgcgt ggtcattctg cccgactcag tgcggaacta catgaccaag ttcctgagcg | 1320 |
| acaggtggat gctgcagaag ggctttctga aggaggagga cctcacggag aagaagccct | 1380 |
| ggtggtggca cctccgtgtt caggagctgg gcctgtcagc cccgctgacc gtgctcccga | 1440 |
| ccatcacctg tgggcacacc atcgagatcc tccgggagaa gggcttcgac caggcgcccg | 1500 |
| tggtggatga ggcgggggta atcctgggaa tggtgacgct tgggaacatg ctctcgtccc | 1560 |
| tgcttgccgg gaaggtgcag ccgtcagacc aagttggcaa agtcatctac aagcagttca | 1620 |
| aacagatccg cctcacggac acgctgggca ggctctcgca catcctggag atggaccact | 1680 |

| | |
|---|---|
| tcgccctggt ggtgcacgag cagatccagt accacagcac cgggaagtcc agtcagcggc | 1740 |
| agatggtgtt cggggtggtc accgccattg acttgctgaa cttcgtggcc gcccaggagc | 1800 |
| gggaccagaa gtgaagtccg gagcgctggg cggtgcggag cgggcccgcc acccttgccc | 1860 |
| acttctcctt cgctttcctg agccctaaac acacgcgtga ttggtaactg cctggcctgg | 1920 |
| caccgttatc cctgcagacg gcacagagca tccgtctccc ctcgttaaca catggcttcc | 1980 |
| taaatggccc tgtttacggc ctatgagatg aaatatgtga ttttctctaa tgtaacttcc | 2040 |
| tcttaggatg tttcaccaag gaaatattga gagagaagtc ggccaggtag gatgaacaca | 2100 |
| ggcaatgact gcgcagagtg gattaaaggc aaaagagaga agagtccagg aaggggcggg | 2160 |
| gagaagcctg ggtggctcag catcctccac gggctgcgcg tctgctcggg gctgagctgg | 2220 |
| cgggagcagt ttgcgtgttt gggtttttta attgagatga aattcaaata acctaaaaat | 2280 |
| caatcacttg aaagtgaaca atcagcggca tttagtacat ccagaaagtt gtgtaggcac | 2340 |
| cacctctgtc acgttctgga acattctgtc atcaccccgt gaagcaatca tttcccctcc | 2400 |
| cgtcttcctc ctcccctggc aactgctgat cgactttgtg tctctgttgt ctaaaatagg | 2460 |
| ttttccctgt tctggacatt tcatataaat ggaatcacac | 2500 |

<210> SEQ ID NO 15
<211> LENGTH: 2068
<212> TYPE: DNA
<213> ORGANISM: Homo sapiens

<400> SEQUENCE: 15

| | |
|---|---|
| cggcagccct cctacctgcg cacgtggtgc cgctgctgct gcctcccgct cgccctgaac | 60 |
| ccagtgcctg cagccatggc tcccggccag ctcgccttat ttagtgtctc tgacaaaacc | 120 |
| ggccttgtgg aatttgcaag aaacctgacc gctcttggtt tgaatctggt cgcttccgga | 180 |
| gggactgcaa aagctctcag ggatgctggt ctggcagtca gagatgtctc tgagttgacg | 240 |
| ggatttcctg aaatgttggg gggacgtgtg aaaactttgc atcctgcagt ccatgctgga | 300 |
| atcctagctc gtaatattcc agaagataat gctgacatgg ccagacttga tttcaatctt | 360 |
| ataagagttg ttgcctgcaa tctctatccc tttgtaaaga cagtggcttc tccaggtgta | 420 |
| actgttgagg aggctgtgga gcaaattgac attggtggag taaccttact gagagctgca | 480 |
| gccaaaaaacc acgctcgagt gacagtggtg tgtgaaccag aggactatgt ggtggtgtcc | 540 |
| acggagatgc agagctccga gagtaaggac acctccttgg agactagacg ccagttagcc | 600 |
| ttgaaggcat tcactcatac ggcacaatat gatgaagcaa tttcagatta tttcaggaaa | 660 |
| cagtacagca aaggcgtatc tcagatgccc ttgagatatg gaatgaaccc acatcagacc | 720 |
| cctgcccagc tgtacacact gcagcccaag cttcccatca cagttctaaa tggagcccct | 780 |
| ggatttataa acttgtgcga tgctttgaac gcctggcagc tggtgaagga actcaaggag | 840 |
| gctttaggta ttccagccgc tgcctctttc aaacatgtca gcccagcagg tgctgctgtt | 900 |
| ggaattccac tcagtgaaga tgaggccaaa gtctgcatgg tttatgatct ctataaaacc | 960 |
| ctcacaccca tctcagcggc atatgcaaga gcaagagggg ctgataggat gtcttcatt | 1020 |
| ggtgattttg ttgcattgtc cgatgtttgt gatgtaccaa ctgcaaaaat tatttccaga | 1080 |
| gaagtatctg atggtataat tgccccagga tatgaagaag aagccttgac aatactttcc | 1140 |
| aaaaagaaaa atgaaaacta ttgtgtcctt cagatggacc aatcttacaa accagatgaa | 1200 |
| aatgaagttc gaactctctt tggtcttcat ttaagccaga agagaaataa tggtgtcgtc | 1260 |
| gacaagtcat tatttagcaa tgttgttacc aaaaataaag atttgccaga gtctgccctc | 1320 |

| | |
|---|---:|
| cgagacctca tcgtagccac cattgctgtc aagtacactc agtctaactc tgtgtgctac | 1380 |
| gccaagaacg ggcaggttat cggcattgga gcaggacagc agtctcgtat acactgcact | 1440 |
| cgccttgcag gagataaggc aaactattgg tggcttagac accatccaca agtgctttcg | 1500 |
| atgaagttta aaacaggagt gaagagagca gaaatctcca atgccatcga tcaatatgtg | 1560 |
| actggaacca ttggcgagga tgaagatttg ataaagtgga aggcactgtt tgaggaagtc | 1620 |
| cctgagttac tcactgaggc agagaagaag gaatgggttg agaaactgac tgaagttttct | 1680 |
| atcagctctg atgccttctt ccctttccga gataacgtag acagagctaa aaggagtggt | 1740 |
| gtggcgtaca ttgcggctcc ctccggttct gctgctgaca aagttgtgat tgaggcctgc | 1800 |
| gacgaactgg gaatcatcct cgctcatacg aaccttcggc tcttccacca ctgattttac | 1860 |
| cacacactgt tttttggctt gcttatgtgt aggtgaacag tcacgcctga aactttgagg | 1920 |
| ataactttt aaaaaaataa aacagtatct cttaaaacaa tgttttgatc tacataaaca | 1980 |
| ttgtaaaaat tttcaatcac gcttttttaac tttcttacca caaaaaaatg ataagtgggt | 2040 |
| gaagtgatgg ttatgttaat tagcgtgc | 2068 |

<210> SEQ ID NO 16
<211> LENGTH: 857
<212> TYPE: DNA
<213> ORGANISM: Homo sapiens

<400> SEQUENCE: 16

| | |
|---|---:|
| gcgtgggcgt gagatggcgg cggcagcggt gagcagcgcc aagcggagcc tgcggggaga | 60 |
| gctgaagcag cgtctgcggg cgatgagtgc cgaggagcgg ctacgccagt cccgcgtact | 120 |
| gagccagaag gtgattgccc acagtgagta tcaaaagtcc aaaagaattt ccatcttttct | 180 |
| gagcatgcaa gatgaaattg agacagaaga gatcatcaag gacattttcc aacgaggcaa | 240 |
| aatctgcttc atccctcggt accggttcca gagcaatcac atggatatgg tgagaataga | 300 |
| atcaccagag gaaatttctt tacttcccaa aacatcctgg aatatccctc agcctggtga | 360 |
| gggtgatgtt cgggaggagg ccttgtccac aggggactt gatctcatct tcatgccagg | 420 |
| ccttgggttt gacaaacatg gcaaccgact ggggagggc aagggctact atgatgccta | 480 |
| tctgaagcgc tgtttgcagc atcaggaagt gaagccctac accctggcgt tggctttcaa | 540 |
| agaacagatt tgcctccagg tcccagtgaa tgaaaacgac atgaaggtag atgaagtcct | 600 |
| ttacgaagac tcgtcaacag cttaaatctg gattactaca gccaaataat cagtgtttta | 660 |
| tatgagagta aagcaaagta tgtgtatttt tcccttgtca aaaattagtt gaaattgttc | 720 |
| attaatgtga atacagactg cattttaaaa ttgtaattat gaaatacctt atataaaacc | 780 |
| atctttaaaa accaatagaa gtgtgaatag tagaatatta attaaaatgg aggctatcag | 840 |
| cctgtgattt tcagctt | 857 |

<210> SEQ ID NO 17
<211> LENGTH: 3762
<212> TYPE: DNA
<213> ORGANISM: Homo sapiens

<400> SEQUENCE: 17

| | |
|---|---:|
| cccgcgagcg tccatccatc tgtccggccg actgtccagc gaaaggggct ccaggccggg | 60 |
| cgcacgtcga cccgggggac cgaggccagg agaggggcca agagcgcggc tgacccttgc | 120 |
| gggccggggc aggggacggt ggccgcggcc atgcagtcct gtgccagggc gtggggctg | 180 |
| cgcctgggcc gcgggtcgg gggcggccgc cgcctggctg ggggatcggg gccgtgctgg | 240 |

-continued

| | |
|---|---|
| gcgccgcgga gccgggacag cagcagtggc ggcggggaca cgccgcggc tggggcctcg | 300 |
| cgcctcctgg agcgccttct gcccagacac gacgacttcg ctcggaggca catcggccct | 360 |
| ggggacaaag accagagaga gatgctgcag accttggggc tggcgagcat tgatgaattg | 420 |
| atcgagaaga cggtccctgc caacatccgt ttgaaaagac ccttgaaaat ggaagaccct | 480 |
| gtttgtgaaa atgaaatcct tgcaactctg catgccattt caagcaaaaa ccagatctgg | 540 |
| agatcgtata ttggcatggg ctattataac tgctcagtgc cacagacgat tttgcggaac | 600 |
| ttactggaga actcaggatg gatcacccag tatactccat accagcctga ggtgtctcag | 660 |
| gggaggctgg agagtttact caactaccag accatggtgt gtgacatcac aggcctggac | 720 |
| atggccaatg catccctgct ggatgagggg actgcagccg cagaggcact gcagctgtgc | 780 |
| tacagacaca acaagaggag gaaatttctc gttgatcccc gttgccaccc acagacaata | 840 |
| gctgttgtcc agactcgagc caaatatact ggagtcctca ctgagctgaa gttaccctgt | 900 |
| gaaatggact tcagtggaaa agatgtcagt ggagtgttgt tccagtaccc agacacggag | 960 |
| gggaaggtgg aagactttac ggaactcgtg agagagctc atcagagtgg gagcctggcc | 1020 |
| tgctgtgcta ctgacctttt agctttgtgc atcttgaggc cacctggaga atttggggta | 1080 |
| gacatcgccc tggcagctc ccagagattt ggagtgccac tgggctatgg gggacccat | 1140 |
| gcagcatttt ttgctgtccg agaaagcttg gtgagaatga tgcctggaag aatggtgggg | 1200 |
| gtaacaagag atgccactgg gaaagaagtg tatcgtcttg ctcttcaaac cagggagcaa | 1260 |
| cacattcgga gagacaaggc taccagcaac atctgtacag ctcaggccct cttggcgaat | 1320 |
| atggctgcca tgtttcgaat ctaccatggt tcccatgggc tggagcatat tgctaggagg | 1380 |
| gtacataatg ccactttgat tttgtcagaa ggtctcaagc gagcagggca tcaactccag | 1440 |
| catgacctgt tctttgatac cttgaagatt cattgtggct gctcagtgaa ggaggtcttg | 1500 |
| ggcagggcgg ctcagcggca gatcaatttt cggcttttg aggatggcac acttggtatt | 1560 |
| tctcttgatg aaacagtcaa tgaaaaagat ctggacgatt tgttgtggat cttggttgt | 1620 |
| gagtcatctg cagaactggt tgctgaaagc atgggagagg agtgcagagg tattccaggg | 1680 |
| tctgtgttca agaggaccag cccgttcctc acccatcaag tgttcaacag ctaccactct | 1740 |
| gaaacaaaca ttgtccggta catgaagaaa ctggaaaata agacatttc ccttgttcac | 1800 |
| agcatgattc cactgggatc ctgcaccatg aaactgaaca gttcgtctga actcgcacct | 1860 |
| atcacatgga aagaatttgc aaacatccac ccctttgtgc ctctggatca agctcaagga | 1920 |
| tatcagcagc ttttccgaga gcttgagaag gatttgtgtg aactcacagg ttatgaccag | 1980 |
| gtctgtttcc agccaaacag cggagcccag ggagaatatg ctggactggc cactatccga | 2040 |
| gcctacttaa accagaaagg agaggggcac agaacggttt gcctcattcc gaaatcagca | 2100 |
| catgggacca acccagcaag tgcccacatg gcaggcatga agattcagcc tgtggaggtg | 2160 |
| gataaatatg gaatatcga tgcagttcac ctcaaggcca tggtggataa gcacaaggag | 2220 |
| aacctagcag ctatcatgat tacatacccca tccaccaatg gggtgtttga agagaacatc | 2280 |
| agtgacgtgt gtgacctcat ccatcaacat ggaggacagg tctacctaga cggggcaaat | 2340 |
| atgaatgctc aggtgggaat ctgtcgccct ggagacttcg gtctgatgt ctcgcaccta | 2400 |
| aatcttcaca agaccttctg cattcccccac ggaggaggtg gtcctggcat ggggcccatc | 2460 |
| ggagtgaaga acatctcgc cccgttttg cccaatcatc ccgtcatttc actaaagcgg | 2520 |
| aatgaggatg cctgtcctgt gggaaccgtc agtgcggccc catggggctc cagttccatc | 2580 |
| ttgcccattt cctgggctta tatcaagatg atgggaggca agggtcttaa acaagccacg | 2640 |

-continued

| | |
|---|---|
| gaaactgcga tattaaatgc caactacatg ccaagcgat tagaaacaca ctacagaatt | 2700 |
| cttttcaggg gtgcaagagg ttatgtgggt catgaatttta ttttggacac gagacccttc | 2760 |
| aaaaagtctg caaatattga ggctgtggat gtggccaaga gactccagga ttatggattt | 2820 |
| cacgccccta ccatgtcctg gcctgtggca gggaccctca tggtggagcc cactgagtcg | 2880 |
| gaggacaagg cagagctgga cagattctgt gatgccatga tcagcattcg gcaggaaatt | 2940 |
| gctgacattg aggagggccg catcgacccc agggtcaatc cgctgaagat gtctccacac | 3000 |
| tccctgacct gcgttacatc ttcccactgg gaccggcctt attcagaga ggtggcagca | 3060 |
| ttcccactcc ccttcatgaa accagagaac aaattctggc caacgattgc ccggattgat | 3120 |
| gacatatatg gagatcagca cctggtttgt acctgcccac ccatggaagt ttatgagtct | 3180 |
| ccattttctg aacaaaagag ggcgtcttct tagtcctctc tccctaagtt taaaggactg | 3240 |
| atttgatgcc tctccccaga gcatttgata agcaagaaag atttcatctc caccccagc | 3300 |
| ctcaagtagg agttttatat actgtgtata tctctgtaat ctctgtcaag gtaaatgtaa | 3360 |
| atacagtagc tggagggagt cgaagctgat ggttggaaga cggatttgct ttggtattct | 3420 |
| gcttccacat gtgccagttg cctggattgg gagccatttt gtgttttgcg tagaaagttt | 3480 |
| taggaacttt aactttaat gtggcaagtt tgcagatgtc atagaggcta tcctggagac | 3540 |
| ttaatagaca tttttttgtt ccaaaagagt ccatgtggac tgtgccatct gtgggaaatc | 3600 |
| ccagggcaaa tgtttacatt ttgtataccc tgaagaactc ttttcctct aatatgccta | 3660 |
| atctgtaatc acatttctga gtgtttcct cttttctgt gtgaggtttt ttttttttt | 3720 |
| aatctgcatt tattagtatt ctaataaaag cattttgatc gg | 3762 |

<210> SEQ ID NO 18
<211> LENGTH: 1192
<212> TYPE: DNA
<213> ORGANISM: Homo sapiens

<400> SEQUENCE: 18

| | |
|---|---|
| ggctccctcc ggccgcgaac tgcccctccc cgccccgcct cccggcgcgg gtggccgagg | 60 |
| cgtagcgccg cgaccccgc acccctgcga acatggcgct gcgagtggtg cggagcgtgc | 120 |
| gggccctgct ctgcaccctg cgcgcggtcc cgttacccgc cgcgccctgc ccgccgaggc | 180 |
| cctggcagct gggggtgggc gccgtccgta cgctgcgcac tggaccccgct ctgctctcgg | 240 |
| tgcgtaaatt cacagagaaa cacgaatggg taacaacaga aaatggcatt ggaacagtgg | 300 |
| gaatcagcaa ttttgcacag gaagcgttgg gagatgttgt ttattgtagt ctccctgaag | 360 |
| ttgggacaaa attgaacaaa caagatgagt ttggtgcttt ggaaagtgtg aaagctgcta | 420 |
| gtgaactata ttctccttta tcaggagaag taactgaaat taatgaagct cttgcagaaa | 480 |
| atccaggact tgtaaacaaa tcttgttatg aagatggttg gctgatcaag atgacactga | 540 |
| gtaacccttc agaactagat gaacttatga gtgaagaagc atatgagaaa tacataaaat | 600 |
| ctattgagga gtgaaaatgg aactcctaaa taaactagta tgaaataacg aagccagcag | 660 |
| agttgtctta aattagtggt ggatagagac ttagaataga aacttttagt attaccgatg | 720 |
| gggcaaaaaa aaactactgt taacactgct aatgaaagaa aatgcccttt aactttgtaa | 780 |
| tgattataga taaatataat atgcgtcttt ttcacaatat cctatgattt ttagactagg | 840 |
| ctctagtgtt cagaattcat gaaattatcc atggtaaaaa ctagttataa aaattacata | 900 |
| attcaaagat aacattgtta ttcttaagcc ttatataata ttgtaacttg catgtatcca | 960 |
| tacctggatt tgggatgaaa tacttaatga tctttccatt ggaaataact ggaagtgaag | 1020 |

| | |
|---|---|
| aggttttgtt gcttgtacag tgtcagatga ggaacaccac tatcttaatt ttgcgataca | 1080 |
| ctgcatttgc tggtgctatt tttatacagt gaagcaacag ctttgcagca aaataataaa | 1140 |
| atacttcttc gttaaaaaaa aaaaaaaaaa aaaaaaaaaa aaaaaaaaaa aa | 1192 |

<210> SEQ ID NO 19
<211> LENGTH: 2102
<212> TYPE: DNA
<213> ORGANISM: Homo sapiens

<400> SEQUENCE: 19

| | |
|---|---|
| tgcccacgcc cccttcagat cctttgctcc ggagagagac ctgtccgagc agaggcctgg | 60 |
| actacatctc ccggcgtgcc tggcagtgtg gtggcctctg tgcgccgtct gcactcgttg | 120 |
| caggcgacga tgcagagggc tgtaagtgtg gtggcccgtc tgggcttttcg cctgcaggca | 180 |
| ttccccccgg ccttgtgtcg tccacttagt tgcgcacagg aggtgctccg caggacaccg | 240 |
| ctctatgact tccacctggc ccacggcggg aaaatggtgg cgtttgcggg ttggagtctg | 300 |
| ccagtgcagt accgggacag tcacactgac tcgcacctgc acacacgcca gcactgctcg | 360 |
| ctctttgacg tgtctcatat gctgcagacc aagatacttg gtagtgaccg ggtgaagctg | 420 |
| atggagagtc tagtggttgg agacattgca gagctaagac caaaccaggg gacactgtcg | 480 |
| ctgtttacca acgaggctgg aggcatctta tgatgacttga ttgtaaccaa tacttctgag | 540 |
| ggccacctgt atgtggtgtc caacgctggc tgctgggaga agatttggc cctcatgcag | 600 |
| gacaaggtca gggagcttca gaaccagggc agagatgtgg gcctggaggt gttggataat | 660 |
| gccctgctag ctctgcaagg ccccactgca gcccaggtac tacaggccgg cgtggcagat | 720 |
| gacctgagga aactgccctt catgaccagt gctgtgatgg aggtgttttgg cgtgtctggc | 780 |
| tgccgcgtga cccgctgtgg ctacacagga gaggatggtg tggagatctc ggtgccggta | 840 |
| gcggggcag ttcacctggc aacagctatt ctgaaaaacc cagaggtgaa gctggcaggg | 900 |
| ctggcagcca gggacagcct gcgcctggag gcaggcctct gcctgtatgg gaatgacatt | 960 |
| gatgaacaca ctacacctgt ggagggcagc ctcagttgga cactggggaa gcgccgccga | 1020 |
| gctgctatgg acttccctgg agccaaggtc attgttcccc agctgaaggg cagggtgcag | 1080 |
| cggaggcgtg tggggttgat gtgtgagggg gccccccatgc gggcacacag tcccatcctg | 1140 |
| aacatggagg taccaagat tggtactgtg actagtggct gccctccccc ctctctgaag | 1200 |
| aagaatgtgg cgatgggtta tgtgccctgc gagtacagtc gtccagggac aatgctgctg | 1260 |
| gtagaggtgc ggcggaagca gcagatggct gtagtcagca agatgccctt gtgcccaca | 1320 |
| aactactata ccctcaagtg aagctggctc agggtggggc tgtcccttcc aggagttttg | 1380 |
| cccctacaag gggttagtca agaagctgag gcagaactca ctgggggtgg gcagttaagg | 1440 |
| tggaggctga ttctaattgt ctggttgagg ggccacacca cctattcccc ccacctaact | 1500 |
| catgccattc cagcttcctt caggaccctg cttctgagtg acggaccagc tcacacaatg | 1560 |
| tcttgtttca gtccatgatc ccactgacct actcttgcct gctggagggt aatgagaagc | 1620 |
| tttggttctg ccatctctcc cactctgcca ggtgctggct gtggagcaaa ggctcacctt | 1680 |
| tgtggagagg ataaaacctg cccaacctac ctcaccatgg ttttcacat gcaaagggt | 1740 |
| aataacatgg gcagtgcgga cttaggctac cccctccagt ttgctttccg taaatgcaaa | 1800 |
| ttgtccttac tgcaagtcag gaatgattgc tgactcacag tagggctgct atgcctgtgt | 1860 |
| gtaaacttgg ggatggctga gggaacatag actcactctt ccacattccc aagttggtct | 1920 |
| agtgtgctgc ccagtagcaa accatggcag actcaccacc tattctgagt tccagggctg | 1980 |

```
ctgtagggca gggtgggctt cctcccagac ttgccttacc ctgggctgat ctttgcccct    2040
ggtatgcatt aatggactcc actgaatcct gaaaaaaaaa ttaaacttcc ttcttacttg    2100
cc                                                                   2102
```

<210> SEQ ID NO 20
<211> LENGTH: 3228
<212> TYPE: DNA
<213> ORGANISM: Homo sapiens

<400> SEQUENCE: 20

```
aaaaaactca ggcaaagtca cagcctcaaa attgttcact gaaagaacgc tgagtggaga      60
agtgtgagaa gatgaatgga ccggtggatg gcttgtgtga ccactctcta agtgaaggag     120
tcttcatgtt cacatcggag tctgtgggag agggacaccc ggataagatc tgtgaccaga     180
tcagtgatgc agtgctggat gcccatctca agcaagaccc caatgccaag gtggcctgtg     240
agacagtgtg caagaccggc atggtgctgc tgtgtggtga gatcacctca atggccatgg     300
tggactacca gcgggtggtg agggacacca tcaagcacat cggctacgat gactcagcca     360
agggctttga cttcaagact tgcaacgtgc tggtggcttt ggagcagcaa tccccagata     420
ttgcccagtg cgtccatctg gacagaaatg aggaggatgt gggggcagga gatcagggtt     480
tgatgttcgg ctatgctacc gacgagacag gaagtgcat gccctcacc atcatccttg     540 ctcacaagct caacgcccgg atggcagacc tcaggcgctc cggcctcctc ccctggctgc     600
ggcctgactc taagactcag gtgacagttc agtacatgca ggacaatggc gcagtcatcc     660
ctgtgcgcat ccacaccatc gtcatctctg tgcagcacaa cgaagacatc acgctggagg     720
agatgcgcag ggccctgaag gagcaagtca tcagggccgt ggtgccggcc aagtacctgg     780
acgaagacac cgtctaccac ctgcagccca gtgggcggtt tgtcatcgga ggtccccagg     840
gggatgcggg tgtcactggc cgtaagatta ttgtggacac ctatggcggc tgggggggctc     900 atggtggtgg ggccttctct gggaaggact acaccaaggt agaccgctca gctgcatatg     960
ctgcccgctg ggtggccaag tctctggtga aagcagggct ctgccggaga gtgcttgtcc    1020
aggtttccta tgccattggt gtggccgagc cgctgtccat ttccatcttc acctacggaa    1080
cctctcagaa cagagcga gagctgctgg atgtggtgca taagaacttc gacctccggc     1140
cgggcgtcat tgtcagggat ttggacttga agaagcccat ctaccagaag acagcatgct    1200
acggccattt cggaagaagc gagttcccat gggaggttcc caggaagctt gtattttaga    1260 gccagggga gctgggcctg gtctcaccct ggaggcacct ggtggccatg ctcctcttcc    1320
ccagacgcct ggctgctgat cgccttcccc acccaccaac cctcagggca aagccaggtc    1380
cctctcattt agcctgtcct gtcatcatca tggccagctg gaggcagggg cttcctggtg    1440
ctggaggttg gatcttgatg taaggatggg catggtgttc tcctgctgct ccctcagact    1500
ggggcaatgt taatttagtg gaaaaggcac ccccgtcaag agtgaattcc ctcactcgtc    1560
tcccccaaca gctggaccct gaccagctcc ccctccctcc ccttgcctgt gccaggtgag    1620
gtcagcacat ctcaacaggc ctcagggctc cttgtgggcc tggctcctg gaccccctt     1680 tcacaggcag ccagtgccct gagccagggt ctccagaaag ccccacccag gccaggcatg    1740 tggcagggggt tagagcagga ctgatgtctc ctaagcacct gtaatgtgcg agggaccag    1800 ctaataactg atctcgtttt ttcttcactg caacatgatg aggtagtacc ttttatatcc    1860
catttataga tgggggaaag caaagcacag agagtctgga taacttccac agggtcccac    1920
agccacgtgt ttagacctag atgtataact aggagctttg actcaggagc ctgtgacata    1980
```

-continued

```
cccccttccc caccgttgtc tcatgccagt aacaggctca acaatgaca aagcagattc    2040 agaaatgagg ccatggactc tgtcctgaag gcctgaggtt actggaaatt aggggattaa    2100
cccactagct cttgttgagc cgtgggcaat tgtctgaaaa gtgaagacag aaccacaggg    2160
ctattttgtt tgcttcatgt gtcccagaag atgactgagg gtgagttggc ttacctggcc    2220
catcagggta ggctggagtt agggactgac cagcagcttt agaatcccag cccctgacc    2280 actcagagac atgcagagat tgggttttg gacttctggg gtaagtggtc taagtccagt    2340
ccagtcctat gtgggcttcc tggagcagaa gcagcaactt gtcctagcac agatggccag    2400 cccttagac agaggccctc aagtctttct ctttccctgg tcccttgtat cccctgcagg    2460
ctgagtgcat ttggagggag tgagtggccc tttcggatcc agggaggctg gtcctatggc    2520
ctcatgttaa ataggcgggg cttgccttct ggtgttggac aagcttctga gacgtcatga    2580
ggagattctg cctttgccag gtgactgtct ggggagcggg tctgctccca aggggcctga    2640
gcagtccttg gcctgctaag gtcttggaac ttgcctgcct ttccatccat ggccagcagc    2700
acctgcccta cctgcccac ttgtccttag cctggacctc tgacagcagc atctctacct    2760
tctccccagc tcccaggacc acaggctcag gcagggcctc catggccccc aggggaacac    2820
tggggacttg gcctctctct agggtacatg gtgctgggag aggcagccca ggaagtctca    2880
tctggggagc aggcagccag catctgggcc ttggcctgga gcacaaagac cctggctttc    2940
attttctctc aggtgaaagg aaattaaggc aacaaagaa gcccggctcc tggtcaccta    3000
ggaagcctca gattccttcc catggaggga gggagtggtt tgcaggtggc caagttcctc    3060
taacttggct cacactcgac atgaaaattc agaattttat actttcccta ccctctagag    3120
aaataagatc ttttttgtca gtttgtttgt atgaaactaa agctttattt gttaatagtt    3180
cctgctaaaa caatgaataa aaactcaagg agcaactaaa aaaaaaaa    3228
```

<210> SEQ ID NO 21
<211> LENGTH: 344
<212> TYPE: PRT
<213> ORGANISM: Homo sapiens

<400> SEQUENCE: 21

```
Met Ser Ala Leu Ala Ala Arg Leu Leu Gln Pro Ala His Ser Cys Ser
 1               5                  10                  15

Leu Arg Leu Arg Pro Phe His Leu Ala Ala Val Arg Asn Glu Ala Val
            20                  25                  30

Val Ile Ser Gly Arg Lys Leu Ala Gln Gln Ile Lys Gln Glu Val Arg
        35                  40                  45

Gln Glu Val Glu Glu Trp Val Ala Ser Gly Asn Lys Arg Pro His Leu
    50                  55                  60

Ser Val Ile Leu Val Gly Glu Asn Pro Ala Ser His Ser Tyr Val Leu
65                  70                  75                  80

Asn Lys Thr Arg Ala Ala Ala Val Val Gly Ile Asn Ser Glu Thr Ile
                85                  90                  95

Met Lys Pro Ala Ser Ile Ser Glu Glu Leu Leu Asn Leu Ile Asn
            100                 105                 110

Lys Leu Asn Asn Asp Asn Val Asp Gly Leu Leu Val Gln Leu Pro
        115                 120                 125

Leu Pro Glu His Ile Asp Glu Arg Arg Ile Cys Asn Ala Val Ser Pro
    130                 135                 140

Asp Lys Asp Val Asp Gly Phe His Val Ile Asn Val Gly Arg Met Cys
145                 150                 155                 160
```

Leu Asp Gln Tyr Ser Met Leu Pro Ala Thr Pro Trp Gly Val Trp Glu
                165                 170                 175

Ile Ile Lys Arg Thr Gly Ile Pro Thr Leu Gly Lys Asn Val Val
        180                 185                 190

Ala Gly Arg Ser Lys Asn Val Gly Met Pro Ile Ala Met Leu Leu His
            195                 200                 205

Thr Asp Gly Ala His Glu Arg Pro Gly Gly Asp Ala Thr Val Thr Ile
        210                 215                 220

Ser His Arg Tyr Thr Pro Lys Glu Gln Leu Lys His Thr Ile Leu
225                 230                 235                 240

Ala Asp Ile Val Ile Ser Ala Ala Gly Ile Pro Asn Leu Ile Thr Ala
            245                 250                 255

Asp Met Ile Lys Glu Gly Ala Ala Val Ile Asp Val Gly Ile Asn Arg
        260                 265                 270

Val His Asp Pro Val Thr Ala Lys Pro Lys Leu Val Gly Asp Val Asp
    275                 280                 285

Phe Glu Gly Val Arg Gln Lys Ala Gly Tyr Ile Thr Pro Val Pro Gly
    290                 295                 300

Gly Val Gly Pro Met Thr Val Ala Met Leu Met Lys Asn Thr Ile Ile
305                 310                 315                 320

Ala Ala Lys Lys Val Leu Arg Leu Glu Glu Arg Glu Val Leu Lys Ser
            325                 330                 335

Lys Glu Leu Gly Val Ala Thr Asn
            340

<210> SEQ ID NO 22
<211> LENGTH: 1283
<212> TYPE: DNA
<213> ORGANISM: Homo sapiens

<400> SEQUENCE: 22
tttcgcagcc gctgccgcct cgccgctgct ccttcgtaag gccacttccg cacaccgaca      60
ccaacatgaa cggacagctc aacggcttcc acgaggcgtt catcgaggag ggcacattcc     120
ttttcacctc agagtcggtc ggggaaggcc acccagataa gatttgtgac caaatcagtg     180
atgctgtcct tgatgcccac cttcagcagg atcctgatgc caaagtagct tgtgaaactg     240
ttgctaaaac tggaatgatc cttcttgctg gggaaattac atccagagct gctgttgact     300
accagaaagt ggttcgtgaa ctgttaaac acattggata tgatgattct tccaaaggtt     360
ttgactacaa gacttgtaac gtgctggtag ccttggagca acagtcacca gatattgctc     420
aaggtgttca tcttgacaga aatgaagaag acattggtgc tggagaccag ggcttaatgt     480
ttggctatgc cactgatgaa actgaggagt gtatgccttt aaccattgtc ttggcacaca     540
agctaaatgc caaactggca gaactacgcc gtaatggcac tttgccttgg ttacgccctg     600
attctaaaac tcaagttact gtgcagtata tgcaggatcg aggtgctgtg cttcccatca     660
gagtccacac aattgttata tctgttcagc atgatgaaga ggtttgtctt gatgaaatga     720
gggatgccct aaaggagaaa gtcatcaaag cagttgtgcc tgcgaaatac cttgatgagg     780
atacaatcta ccacctacag ccaagtggca gatttgttat tggtgggcct cagggtgatg     840
ctggtttgac tggacggaaa atcattgtgg acacttatgg cggttggggt gctcatggag     900
gaggtgcctt ttcaggaaag gattatacca aggtcgaccg ttcagctgct tatgctgctc     960
gttgggtggc aaaatccctt gttaaaggag gtctgtgccg gagggttctt gttcaggtct    1020
cttatgctat tggagtttct catccattat ctatctccat tttccattat ggtacctctc    1080

-continued

| | |
|---|---|
| agaagagtga gagagagcta ttagagattg tgaagaagaa tttcgatctc cgccctgggg | 1140 |
| tcattgtcag ggatctggat ctgaagaagc caatttatca gaggactgca gcctatggcc | 1200 |
| actttggtag ggacagcttc ccatgggaag tgcccaaaaa gcttaaatat tgaaagtgtt | 1260 |
| agccttttt ccccagactt gtt | 1283 |

<210> SEQ ID NO 23
<211> LENGTH: 3259
<212> TYPE: DNA
<213> ORGANISM: Homo sapiens

<400> SEQUENCE: 23

| | |
|---|---|
| caaggttggt ggaagtcgcg ttgtgcaggt tcgtgcccgg ctggcgcggc gtggtttcac | 60 |
| tgttacatgc cttgaagtga tgaggaggtt tctgttacta tatgctacac agcagggaca | 120 |
| ggcaaaggcc atcgcagaag aaatgtgtga gcaagctgtg gtacatggat tttctgcaga | 180 |
| tcttcactgt attagtgaat ccgataagta tgacctaaaa accgaaacag ctcctcttgt | 240 |
| tgttgtggtt tctaccacgg gcaccggaga cccacccgac acagcccgca gtttgttaa | 300 |
| ggaaatacag aaccaaacac tgccggttga tttctttgct cacctgcggt atgggttact | 360 |
| gggtctcggt gattcagaat acacctactt tgcaatgggg gggaagataa ttgataaacg | 420 |
| acttcaagag cttggagccc ggcatttcta tgacactgga catgcagatg actgtgtagg | 480 |
| tttagaactt gtggttgagc cgtggattgc tggactctgg ccagccctca gaaagcattt | 540 |
| taggtcaagc agaggacaag aggagataag tggcgcactc ccggtggcat cacctgcatc | 600 |
| cttgaggaca gaccttgtga agtcagagct gctacacatt gaatctcaag tcgagcttct | 660 |
| gagattcgat gattcaggaa gaaggattc tgaggttttg aagcaaaatg cagtgaacag | 720 |
| caaccaatcc aatgttgtaa ttgaagactt tgagtcctca cttacccgtt cggtaccccc | 780 |
| actctcacaa gcctctctga atattcctgg tttacccca gaatatttac aggtacatct | 840 |
| gcaggagtct cttggccagg aggaaagcca agtatctgtg acttcagcag atccagtttt | 900 |
| tcaagtgcca atttcaaagg cagttcaact tactacgaat gatgccataa aaaccactct | 960 |
| gctggtagaa ttggacattt caaatacaga cttttcctat cagcctggag atgccttcag | 1020 |
| cgtgatctgc cctaacagtg attctgaggt acaaagccta ctccaaagac tgcagcttga | 1080 |
| agataaaaga gagcactgcg tccttttgaa aataaaggca gacacaaaga agaaaggagc | 1140 |
| taccttaccc cagcatatac ctgcgggatg ttctctccag ttcatttta cctggtgtct | 1200 |
| tgaaatccga gcaattccta aaaaggcatt tttgcgagcc cttgtggact ataccagtga | 1260 |
| cagtgctgaa aagcgcaggc tacaggagct gtgcagtaaa caaggggcag ccgattatag | 1320 |
| ccgctttgta cgagatgcct gtgcctgctt gttggatctc ctcctcgctt tcccttcttg | 1380 |
| ccagccacca ctcagtctcc tgctcgaaca tcttcctaaa cttcaaccca gaccatattc | 1440 |
| gtgtgcaagc tcaagtttat ttcacccagg aaagctccat tttgtcttca acattgtgga | 1500 |
| atttctgtct actgccacaa cagaggttct gcggaaggga gtatgtacag gctggctggc | 1560 |
| cttgttggtt gcttcagttc ttcagccaaa catacatgca tcccatgaag acagcgggaa | 1620 |
| agccctggct cctaagatat ccatctctcc tcgaacaaca aattctttcc acttaccaga | 1680 |
| tgaccctca atcccatca taatggtggg tccaggaacc ggcatagccc cgttattgg | 1740 |
| gttcctacaa catagagaga aactccaaga acaacaccca gatggaaatt ttggagcaat | 1800 |
| gtggttgttt tttggctgca ggcataagga tagggattat ctattcagaa aagagctcag | 1860 |
| acatttcctt aagcatggga tcttaactca tctaaaggtt tccttctcaa gagatgctcc | 1920 |

```
tgttggggag gaggaagccc cagcaaagta tgtacaagac aacatccagc ttcatggcca    1980
gcaggtggcg agaatcctcc tccaggagaa cggccatatt tatgtgtgtg agatgcaaa     2040 gaatatggcc aaggatgtac atgatgccct tgtgcaaata ataagcaaag aggttggagt    2100
tgaaaaacta gaagcaatga aaaccctggc cactttaaaa aagaaaaac gctaccttca     2160 ggatatttgg tcataaaacc agaaattaaa gaaagaggat taagcttttt tgactgaaag    2220
tactaaaagt cagctttact agtgccaaac ctttaaattt tcaaaagaaa attttcttt     2280 aacatttctt gaaggacatg gagtggagat tggatcattt aacaatataa caaaacttcc    2340
tgatttgatt ttacgtatct tctatctacg cccttcctgt gcctgtgact ctccccaaat    2400
tgccctgttg ccttgagctc ttctgagcta aaggcagcct tcagtcccta tcagcgcctc    2460
ctttacttcc cagagaactt cacagagact ctgtccttcc atgcaaaggc ttcctgaaat    2520
aggggagact gactgagtag ctcattcttg tgacttacag tgccaacatt taaaaaagta    2580
tgaaaatgat ttatttttat atgatgtata cccataaaga atgctcatat taatgtactt    2640
aaattacaca tgtagagcat atctgttata tgtttatgta actatcaaat ggttatttgt    2700
tactaaagct atatttctga taaaaaatat tttaggataa ttgcctacag agggattat     2760 ttttatgatg ctgggaaata tgaaatgtat tttaaaattt cactctgggc atatggattt    2820
atctatcacc attactttt ttaagtcac aatttcagaa ttttgggaca tttgcattca      2880
atttacaggt accagtacgt acatatttta atagaaagat acaaccttt tattttcact     2940 ccttttattt ctgctgcttg gcacatttt gagttttccc acattatttg tctccatgat     3000
accactcaag cagtgtgctg gacctaaaat actgacttta gttagtatcc ttggatttt     3060 agattcccca gtgtctaatt ccctgttata atttgcacaa acaaaacaaa atgttatgat    3120
aatctttctc cactgttcta atatatattg tatttttatt tgatagcttg ggatttaaaa    3180
catctctgtt gaaggctttt gatccttttg agaaataaag atctgaaaga aatggcataa    3240
tcttaaaaaa aaaaaaaaa                                                 3259
```

<210> SEQ ID NO 24
<211> LENGTH: 1805
<212> TYPE: DNA
<213> ORGANISM: Homo sapiens

<400> SEQUENCE: 24

```
aagagactga actgtatctg cctctatttc caaaagactc acgttcaact ttcgctcaca     60
caaagccggg aaaattttat tagtcctttt tttaaaaaaa gttaatataa aattatagca    120
aaaaaaaaaa ggaacctgaa ctttagtaac acagctggaa caatcgcagc ggcggcggca    180
gcggcgggag aagaggttta atttagttga ttttctgtgg ttgttggttg ttcgctagtc    240
tcacggtgat ggaagctgca ctttttttcg aagggaccga aagctgctg gaggtttggt     300 tctcccggca gcagcccgac gcaaaccaag gatctgggga tcttcgcact atcccaagat    360
ctgagtggga catactttg aaggatgtgc aatgttcaat cataagtgtg acaaaaactg      420
acaagcagga agcttatgta ctcagtgaga gtagcatgtt tgtctccaag agacgtttca    480
ttttgaagac atgtggtacc accctcttgc tgaaagcact ggttcccctg ttgaagcttg    540
ctagggatta cagtgggttt gactcaattc aaagcttctt ttattctcgt aagaatttca    600
tgaagccttc tcaccaaggg tacccacacc ggaatttcca ggaagaaata gagtttctta    660
atgcaatttt cccaaatgga gcaggatatt gtatgggacg tatgaattct gactgttggt    720
acttatatac tctggatttc ccagagagtc gggtaatcag tcagccagat caaaccttgg    780
```

-continued

```
aaattctgat gagtgagctt gacccagcag ttatggacca gttctacatg aaagatggtg    840
ttactgcaaa ggatgtcact cgtgagagtg gaattcgtga cctgatacca ggttctgtca    900
ttgatgccac aatgttcaat ccttgtgggt attcgatgaa tggaatgaaa tcggatggaa    960
cttattggac tattcacatc actccagaac cagaattttc ttatgttagc tttgaaacaa   1020
acttaagtca gacctcctat gatgacctga tcaggaaagt tgtagaagtc ttcaagccag   1080
gaaaatttgt gaccaccttg tttgttaatc agagttctaa atgtcgcaca gtgcttgctt   1140
cgccccagaa gattgaaggt tttaagcgtc ttgattgcca gagtgctatg ttcaatgatt   1200
acaattttgt ttttaccagt tttgctaaga agcagcaaca acagcagagt tgattaagaa   1260
aaatgaagaa aaaacgcaaa agagaacac  atgtagaagg tggtggatgc tttctagatg   1320
tcgatgctgg gggcagtgct ttccataacc accactgtgt agttgcagaa agccctagat   1380
gtaatgatag tgtaatcatt ttgaattgta tgcattatta tatcaaggag ttagatatct   1440
tgcatgaatc ctctcttctg tgtttaggta ttctctgcca ctcttgctgt gaaattgaag   1500
tggatgtaga aaaaaccttt tactatatga aactttacaa cacttgtgaa agcaactcaa   1560
tttggtttat gcacagtgta atatttctcc aagtatcatc caaaattccc cacagacaag   1620
gctttcgtcc tcattaggtg ttggcctcag cctaaccctc taggactgtt ctattaaatt   1680
gctgccagaa ttttacatcc agttacctcc actttctaga acatattctt tactaatgtt   1740
attgaaacca atttctactt catactgatg tttttggaaa cagcaattaa agttttctctt   1800 ccatg                                                                1805
```

<210> SEQ ID NO 25
<211> LENGTH: 254
<212> TYPE: PRT
<213> ORGANISM: Homo sapiens

<400> SEQUENCE: 25

```
Gln Asp Ile Leu Val Phe Arg Ser Lys Thr Tyr Gly Asn Val Leu Val
  1               5                  10                  15

Leu Asp Gly Val Ile Gln Cys Thr Glu Arg Asp Glu Phe Ser Tyr Gln
             20                  25                  30

Glu Met Ile Ala Asn Leu Pro Leu Cys Ser His Pro Asn Pro Arg Lys
         35                  40                  45

Val Leu Ile Ile Gly Gly Asp Gly Gly Val Leu Arg Glu Val Val
     50                  55                  60

Lys His Pro Ser Val Glu Ser Val Val Gln Cys Glu Ile Asp Glu Asp
 65                  70                  75                  80

Val Ile Gln Val Ser Lys Lys Phe Leu Pro Gly Met Ala Ile Gly Tyr
                 85                  90                  95

Ser Ser Ser Lys Leu Thr Leu His Val Gly Asp Gly Phe Glu Phe Met
            100                 105                 110

Lys Gln Asn Gln Asp Ala Phe Asp Val Ile Ile Thr Asp Ser Ser Asp
        115                 120                 125

Pro Met Gly Pro Ala Glu Ser Leu Phe Lys Glu Ser Tyr Tyr Gln Leu
    130                 135                 140

Met Lys Thr Ala Leu Lys Glu Asp Gly Val Leu Cys Cys Gln Gly Glu
145                 150                 155                 160

Cys Gln Trp Leu His Leu Asp Leu Ile Lys Glu Met Arg Gln Phe Cys
                165                 170                 175

Gln Ser Leu Phe Pro Val Val Ala Tyr Ala Tyr Cys Thr Ile Pro Thr
            180                 185                 190
```

```
        Tyr Pro Ser Gly Gln Ile Gly Phe Met Leu Cys Ser Lys Asn Pro Ser
                195                 200                 205

Thr Asn Phe Gln Glu Pro Val Gln Pro Leu Thr Gln Gln Gln Val Ala
            210                 215                 220

Gln Met Gln Leu Lys Tyr Tyr Asn Ser Asp Val His Arg Ala Ala Phe
        225                 230                 235                 240

Val Leu Pro Glu Phe Ala Arg Lys Ala Leu Asn Asp Val Ser
                        245                 250

<210> SEQ ID NO 26
<211> LENGTH: 2211
<212> TYPE: DNA
<213> ORGANISM: Homo sapiens

<400> SEQUENCE: 26
ctgaggccca gccccttcg cccgtttcca tcacgagtgc cgccagcatg tctgacaaac      60
tgccctacaa agtcgccgac atcggcctgg ctgcctgggg acgcaaggcc ctggacattg     120
ctgagaacga gatgccgggc ctgatgcgta tgcgggagcg gtactcggcc tccaagccac     180
tgaagggcgc ccgcatcgct ggctgcctgc acatgaccgt ggagacggcc gtcctcattg     240
agaccctcgt cacctggt gctgaggtgc agtggtccag ctgcaacatc ttctccaccc      300
agaaccatgc ggcggctgcc attgccaagg ctggcattcc ggtgtatgcc tggaagggcg     360
aaacggacga ggagtacctg tggtgcattg agcagaccct gtacttcaag gacgggcccc     420
tcaacatgat tctggacgac ggggggcgacc tcaccaacct catccacacc aagtacccgc     480
agcttctgcc aggcatccga ggcatctctg aggagaccac gactggggtc cacaacctct     540
acaagatgat ggccaatggg atcctcaagg tgcctgccat caatgtcaat gactccgtca     600
ccaagagcaa gtttgacaac ctctatggct gccgggagtc cctcatagat ggcatcaagc     660
gggccacaga tgtgatgatt gccggcaagg tagcggtggt agcaggctat ggtgatgtgg     720
gcaagggctg tgcccaggcc ctgcgggt tcggagcccg cgtcatcatc accgagattg     780 acccccatcaa cgcactgcag gctgccatgg agggctatga ggtgaccacc atggatgagg     840
cctgtcagga gggcaacatc tttgtcacca ccacaggctg tattgacatc atccttggcc     900
ggtaggtgcc agatgggggg tcccggggag tgagggagga gggcagagtt gggacagctt     960
tctgtccctg acaatctccc acggtcttgg gctgcctgac aggcactttg agcagatgaa    1020
ggatgatgcc attgtgtgta acattggaca ctttgacgtg gagatcgatg tcaagtggct    1080
caacgagaac gccgtggaga aggtgaacat caagccgcag gtggaccggg tcggttgaa    1140 gaatgggcgc cgcatcatcc tgctggccga gggtcggctg gtcaacctgg gttgtgccat    1200 gggccaccc agcttcgtga tgagtaactc cttcaccaac caggtgatgg cgcagatcga    1260
gctgtggacc catccagaca agtaccccgt tggggttcat ttcctgccca agaagctgga    1320
tgaggcagtg gctgaagccc acctgggcaa gctgaatgtg aagttgacca agctaactga    1380
gaagcaagcc cagtacctgg gcatgtcctg tgatggcccc ttcaagccgg atcactaccg    1440
ctactgagag ccaggtctgc gtttcaccct ccagctgctg tccttgccca ggccccacct    1500
ctcctcccta agagctaatg gcaccaactt gtgattggt ttgtcagtgt ccccatcga    1560 ctctctgggg ctgatcactt agttttggc ctctgctgca gccgtcatac tgttccaaat    1620
gtggcagcgg gaacagagta ccctcttcaa gccccggtca tgatggaggt cccagccaca    1680
gggaaccatg agctcagtgg tcttggaaca gctcactaag tcagtccttc cttagcctgg    1740
aagtcagtag tggagtcaca aagcccatgt gttttgccat ctaggccttc acctggtctg    1800
```

-continued

| | |
|---|---|
| tggacttata cctgtgtgct tggtttacag gtccagtggt tcttcagccc atgacagatg | 1860 |
| agaagggggct atattgaagg gcaaagagga actgttgttt gaattttcct gagagcctgg | 1920 |
| cttagtgctg ggccttctct taaacctcat tacaatgagg ttagtacttt tagtccctgt | 1980 |
| tttacagggg ttagaataga ctgttaaggg gcaactgaga aagaacagag aagtgacagc | 2040 |
| tagggggttga gaggggccag aaaaacatga atgcaggcag atttcgtgaa atctgccacc | 2100 |
| actttataac cagatggttc cttttcacaac cctgggtcaa aaagagaata atttggccta | 2160 |
| taatgttaaa agaaagcagg aaggtgggta aataaaaatc ttggtgcctg g | 2211 |

<210> SEQ ID NO 27
<211> LENGTH: 2436
<212> TYPE: DNA
<213> ORGANISM: Homo sapiens

<400> SEQUENCE: 27

| | |
|---|---|
| cgaccacctg tctggacacc acaaagatgc caccgtggg gggcaaaaag gccaagaagg | 60 |
| gcatcctaga acgtttaaat gctggagaga ttgtgattgg agatggaggg tttgtctttg | 120 |
| cactggagaa gagggggctac gtaaaggcag gaccctggac tcctgaagct gctgtggagc | 180 |
| acccagaagc agttcgccag cttcatcgag agttcctcag agctggctca aacgtcatgc | 240 |
| agaccttcac cttctatgcg agtgaagaca agctggagaa caggggcaac tatgtcttag | 300 |
| agaagatatc tgggcaggaa gtcaatgaag ctgcttgcga catcgcccga caagtggctg | 360 |
| atgaaggaga tgctttggta gcaggaggag tgagtcagac accttcatac cttagctgca | 420 |
| agagtgaaac tgaagtcaaa aaagtatttc tgcaacagtt agaggtcttt atgaagaaga | 480 |
| acgtggactt cttgattgca gagtattttg aacacgttga agaagctgtg tgggcagttg | 540 |
| aaaccttgat agcatccggt aaacctgtgg cagcaaccat gtgcattggc ccagaaggag | 600 |
| atttgcatgg cgtgcccccc ggcgagtgtg cagtgcgcct ggtgaaagca ggagcatcca | 660 |
| tcattggtgt gaactgccac tttgacccca ccattagttt aaaaacagtg aagctcatga | 720 |
| aggagggctt ggaggctgcc caactgaaag ctcacctgat gagccagccc ttggcttacc | 780 |
| acactcctga ctgcaacaag cagggattca tcgatctccc agaattccca tttggactgg | 840 |
| aacccagagt tgccaccaga tgggatattc aaaaatacgc cagagaggcc tacaacctgg | 900 |
| gggtcaggta cattggcggg tgctgtggat ttgagcccta ccacatcagg gcaattgcag | 960 |
| aggagctggc cccagaaagg ggcttttttgc caccagcttc agaaaaacat ggcagctggg | 1020 |
| gaagtggttt ggacatgcac accaaaccct gggttagagc aagggccagg aaggaatact | 1080 |
| gggagaatct tcggatagcc tcaggccggc catacaaccc ttcaatgtca agccagatg | 1140 |
| gctggggagt gaccaaagga acagccgagc tgatgcagca gaaagaagcc acaactgagc | 1200 |
| agcagctgaa agagctcttt gaaaaacaaa aattcaaatc acagtagcct cgatagaagc | 1260 |
| tatttttgat gaatttctag gtgtttgggt cacagttcct acaaatacgg aaaaggggggt | 1320 |
| taaaaagcag tgctttcatg aatgccatcc tacacatatt attgctatta cctgaacaaa | 1380 |
| atagaattac aaatagcact tgataatttt aaagtatgtt ttagaaattt tcttaggagc | 1440 |
| aaaataagta caaagtaaat cttgaacagg ttcactaagc acccacctg tgaaaagtat | 1500 |
| tatgaaaatc actgcagcac aggaaaagta attcagatgt taatgccact tgaagaagtt | 1560 |
| ggtaggctag caaagaggat gagacatgaa ctgtcataaa ggactcagca accagccagg | 1620 |
| gacagataaa gcgctatgga aaggggcttc caagttcttt tgaacatgac ccttagtaac | 1680 |
| aaacacaatt tatataatga cccagcaaaa cacatcacat cttactgtcg aaattaaatg | 1740 |

```
tgtgatccat cctagtattt tctgttccat tccttttcat tctatttcat ttataaaaca     1800
tgctagttga gacttttcaa atggatttt atgacccact actgggtttg gatccacagt     1860
ttgaaaaata ttgctacaag acacttaagg agaccatcct gtttaagttt attcttataa     1920
gtaggtcagt catatgagac ctgatcaata aatatccaat acccagagtc ctgctctcag     1980
agttcttctg tttcgtgacc cacttttcta ccagtaaaag acatagacca atggggagga     2040
ggggaggaga gatggatatt tcagccctct ccatcctagt caacactgga tccacctagt     2100
gcctctgggc cataaggctg agcagagtga gcttgtatta gttggtagct tttaaaaaat     2160
ataataaaaa aaaagtagag attctccaaa ctctagcctg gtttcctaga ttgagaacta     2220
tgatattttt ctctgataat ttaatatcta ctctcctaca aaagctcaag cctgaagata     2280
caagactatt agaagaaaca tgactaccct cagtgtatta gaaagaggt catgcagctt     2340 tctaaacatt attgaattgt ttgagctgtt ttgaaattgt aattctttc agctattaaa     2400 aagaagagca atgagaaaaa aaaaaaaaaa aaaaaa                               2436

<210> SEQ ID NO 28
<211> LENGTH: 1326
<212> TYPE: DNA
<213> ORGANISM: Homo sapiens

<400> SEQUENCE: 28 ttctttcct ctcttcttct ttcgcggttc agcatgcagg aaaaagacgc ctcctcacaa      60
ggtttcctgc cacacttcca acatttcgcc acgcaggcga tccatgtggg ccaggatccg    120
gagcaatgga cctccagggc tgtagtgccc cccatctcac tgtccaccac gttcaagcaa    180
ggggcgcctg ccagcactc gggttttgaa tatagccgtt ctggaaatcc cactaggaat    240
tgccttgaaa aagcagtggc agcactggat ggggctaagt actgtttggc ctttgcttca    300
ggtttagcag ccactgtaac tattacccat cttttaaaag caggagacca aattatttgt    360
atggatgatg tgtatggagg tacaaacagg tacttcaggc aagtggcatc tgaatttgga    420
ttaaagattt cttttgttga ttgttccaaa atcaaattac tagaggcagc aattaccaca    480
gaaaccaagc ttgtttggat cgaaaccccc acaaacccca cccagaaggt gattgacatt    540
gaaggctgtg cacatattgt ccataagcat ggagacatta ttttggtcgt ggataacact    600
tttatgtcac catatttcca gcgcccttg gctctgggag ctgatatttc tatgtattct    660
gcaacaaaat acatgaatgg ccacagtgat gttgtaatgg gcctggtgtc tgttaattgt    720
gaaagccttc ataatagact tcgtttcttg caaaactctc ttggagcagt tccatctcct    780
attgattgtt acctctgcaa tcgaggtctg aagactctac atgtccgaat ggaaaagcat    840
ttcaaaaacg gaatggcagt tgcccagttc ctggaatcta atccttgggt agaaaaggtt    900
atttatcctg ggctgcccctc tcatccacag catgagttgg tgaagcgtca gtgtacaggt    960
tgtacaggga tggtcacctt ttatattaag ggcactcttc agcatgctga gattttcctc   1020
aagaacctaa agctatttac tctggccgag agcttgggag gattcgaaag ccttgctgag   1080
cttccggcaa tcatgactca tgcatcagtt cttaagaatg acagagatgt ccttggaatt   1140
agtgacacac tgattcgact ttctgtgggc ttagaggatg aggaagacct actggaagat   1200
ctagatcaag ctttgaaggc agcacaccct ccaagtggaa ttcacagcta gtattccaga   1260
gctgctatta gaagctgctt cctgtgaaga tcaatcttcc tgagtaatta atggaccaac   1320
aatgag                                                               1326

<210> SEQ ID NO 29
```

```
<211> LENGTH: 49
<212> TYPE: DNA
<213> ORGANISM: Artificial Sequence
<220> FEATURE:
<223> OTHER INFORMATION: Description of Artificial Sequence: PCR product

<400> SEQUENCE: 29
cccacggtcg gggtacctgg gcgggacgcg ccaggccgac tcccggcga          49

<210> SEQ ID NO 30
<211> LENGTH: 3464
<212> TYPE: DNA
<213> ORGANISM: Homo sapiens

<400> SEQUENCE: 30
tttaatggac acataattta attatatatt ttttcttaca gatacccagg tgttctctct    60
gatgtccagg aggagaaagg cattaagtac aaatttgaag tatatgagaa gaatgattaa   120
tatgaaggtg ttttctagtt taagttgttc ccctccctc tgaaaaaagt atgtattttt    180
acattagaaa aggttttttg ttgactttag atctataatt atttctaagc aactagtttt   240
tattccccac tactcttgtc tctatcagat accatttatg agacattctt gctataacta   300
agtgcttctc caagaccca actgagtccc cagcacctgc tacagtgagc tgccattcca    360
cacccatcac atgtggcact cttgccagtc cttgacattg tcgggctttt cacatgttgg   420
taatatttat taaagatgaa gatccacata cccttcaact gagcagtttc actagtggaa   480
ataccaaaag cttcctacgt gtatatccag aggtttgtag ataaatgttg ccaccttgtt   540
tgtaacagtg aaaaattgaa acaacctggg aagtccagtg atgggaaaat gagtatgttt   600
ctgtcttaga ttggggaacc caaagcagat tgcaagactg aaatttcagt gaaagcagtg   660
tatttgctag gtcataccag aaatcatcaa ttgaggtacg gagaaactga actgagaagg   720
taagaaaagc aatttaaagt cagcgagcag gttctcattg ataacaagct ccatactgct   780
gagatacagg gaaatggagg ggggaaagct ggagtattga tcccgccccc ctccttggtt   840
gtcagctccc tgtcctgtgt gtgggcggaa catagtccag ctgctctata gcaagtctca   900
ggtgtttgca gtaagaagct gctggcatgc acgggaacga tgaatgccaa acacttaaag   960
caattcgatg tttaagtatg taagttcttt tttttttaga cagcgtttcg ctcttgttgc  1020
ccaggctagc atgcaatggt gtgacctcgg cttactgcaa cctccgcctt cccagattca  1080
agcgattctc ctgcctcagg ctcccaagta gctaggacca ggtgcgcgcc accacgcccg  1140
gctaattttt gtattttgta ttttagtag agatgggggtt tcaccatgtt ggtcaggcta  1200
gtctcgaact cgtgaccgca agcgattcac ccacctcagc ctcccaaagt gctgggatta  1260
ccggcttgag ccaccacacc cggcacatct tcattctttt tatgtagtaa aaagtataag  1320
gccacacatg gtttatttga agtattttat aatttaaaaa aatacagaag caggaaaacc  1380
aattataagt tcaagtgagg gatgatggtt gcttgaacca aagggttgca tgtagtaaga  1440
aattgtgatt taagatatat tttaaagtta taagtagcag gatattctga tggagtttga  1500
ctttggtttt gggcccaggg agtttcagat gcctttgaga aatgaatgaa gtagagagaa  1560
aataaaagaa aaaccagcca ggcacagtgg ctcacacctg taatcccagc gctttgggag  1620
gctaaggcag gcagatcact tgagaccagc ttgggcaaca tggcaaagcc ccatctctac  1680
aaaaaacaca aaaattagct gggcattgtg gcgcacacct gtattcccat ctagtcagga  1740
agctgagatg gaagaattaa ttgagcccac gagttcaagg ctgcagtgag tcgtgattgt  1800
gccactgcac tccagccggg gtgacagaag agaccttgtc tcgaaaacga atctgaaaac  1860
```

-continued

| | |
|---|---|
| aatggaacca tgccttcata attctagaaa gttattttca actgataaat ctatattcac | 1920 |
| ccaaataatc aagggtgaag gtaaaataat acatttttag acaagcaaag actcaggggt | 1980 |
| tacctccatg tgccctttt agggaagctg ttggagaaaa tactccagca aaatgaagga | 2040 |
| gtacacaaac cagagaatga catgaatcca gcaaatagga tccaacacag gcaatattcc | 2100 |
| agctatggag ctagctttaa aaaggaacag taaaaatatt aatcggttag ctgggtggaa | 2160 |
| tggcccatgc ctgtagtccc agctactcag gaggctcagc agcaggacga cttgagccca | 2220 |
| agagttccag accagcctgg ccaccttagt gagatccctt ctcttaaaaa taataactta | 2280 |
| ttgccagatt tggggcattt ggaaagaagt tcattgaaga taaagcaaaa gtaaaaaaaa | 2340 |
| aaaaaaaaaa aacaagggga aagggttggt taggcaatca ttctagggca gaaagaagta | 2400 |
| caggatagga agagcataat acactgtttt tctcaacaag gagcagtatg tacacagtca | 2460 |
| taatgatgtg actgcttagc ccctaaatat ggtaactact ctgggacaat atgggaggaa | 2520 |
| aagtgaagat tgtgatggtg taagagctaa tcctcatctg tcatatccag aaatcactat | 2580 |
| ataatatata ataatgaaat gactaagtta tgtgaggaaa aaaacagaag acattgctaa | 2640 |
| aagagttaaa agtcattgct ctggagaatt aggaggatg gggcagggga ctgttaggat | 2700 |
| gcattataaa ctgaaaagcc ttttaaaat tttatgtatt aatatatgca ttcacttgaa | 2760 |
| aaactaaaaa aaacaataa tttgaaaaaa cccatgaagg taactaacgg aaggaaaaac | 2820 |
| taagagaatg aaaagtattt gcctctggaa agaacaactg gcaggactgt tgttttcatt | 2880 |
| gtaagacttt tggagccatt taattgtact taaccatttt catctatttc tttaataaga | 2940 |
| acaattccat cttaataaag agttacactt gttaataagt gctggcctcc tgttgttctt | 3000 |
| tgtacacccc acacaaaatt tcaaagaaac tttgatggca atatatctcc atggtcagct | 3060 |
| taaaaataga gaaaggaaaa catagaatta gccaagagtc acacaaaaca aagatcagtt | 3120 |
| gtttgttagg aaacaatcaa aatcaagtct cactttttcc agattggctt atggaacagc | 3180 |
| actgtaaggt gataacttgg ggcaaacatg taaaataataa acatatgtt ttaaatattc | 3240 |
| aggttagcac attttatgtt tctgtgagat taaaattgtg tgtgacatac ccgcttcctt | 3300 |
| aaaggcaatg tttctgaaaa tgttgtacct gctattcctg aatcagggat gggtcccaga | 3360 |
| atctgccttt taaacatctc agataatctg aagcctgctt aagtttgtaa ggcactgctt | 3420 |
| ttgcactcta aggaagaaaa aaacaagttt taattcccgt ctct | 3464 |

<210> SEQ ID NO 31
<211> LENGTH: 1584
<212> TYPE: DNA
<213> ORGANISM: Homo sapiens

<400> SEQUENCE: 31

| | |
|---|---|
| cggggcagct ctgaggaaca aggtggaagc tcagagcgct ggtctccacc ctggtgcccc | 60 |
| tgggctggtg ctggcagtgg gagccgtggc tgtggatgag agacatagac gagagagtga | 120 |
| gatggcctgg tttgccctct acctcctgag ccttctctgg gctacagctg ggactagtac | 180 |
| ccagacccag agttcatgct ccgttccctc agcacaggag cccttggtca atggaataca | 240 |
| agtactcatg gagaactcgg tgacttcatc agcctaccca aaccccagca tcctgattgc | 300 |
| catgaatctg gccggagcct acaacttgaa ggcccagaag ctcctgactt accagctcat | 360 |
| gtccagcgac aacaacgatc taaccattgg gcacctcggc ctcaccatca tggccctcac | 420 |
| ctcctcctgc cgagaccctg gggataaagt atccattcta caaagacaaa tggagaactg | 480 |
| ggcaccttcc agccccaacg ctgaagcatc agccttctat gggcccagtc tagcgatctt | 540 |

```
ggcactgtgc cagaagaact ctgaggcgac cttgccgata gccgtccgct ttgccaagac    600
cctgctggcc aactcctctc ccttcaatgt agacacagga gcaatggcaa ccttggctct    660
gacctgtatg tacaacaaga tccctgtagg ttcagaggaa ggttacagat ccctgtttgg    720
tcaggtacta aaggatattg tggagaaaat cagcatgaag atcaaagata atggcatcat    780
tggagacatc tacagtactg gcctcgccat gcaggctctc tctgtaacac ctgagccatc    840
taaaaaggaa tggaactgca agaagactac ggatatgata ctcaatgaga ttaagcaggg    900
gaaattccac aaccccatgt ccattgctca aatcctccct tccctgaaag gcaagacata    960
cctagatgtg ccccaggtca cttgtagtcc tgatcatgag gtacaaccaa ctctacccag   1020
caaccctggc cctggcccca cctctgcatc taacatcact gtcatataca ccataaataa   1080
ccagctgagg ggggttgagc tgctcttcaa cgagaccatc aatgttagtg tgaaaagtgg   1140
gtcagtgtta cttgttgtcc tagaggaagc acagcgcaaa aatcctatgt tcaaatttga   1200
aaccacaatg acatcttggg gccttgtcgt ctcttctatc aacaatatcg cggaaaatgt   1260
taatcacaag acatactggc agtttcttag tggtgtaaca ccttttgaatg aagggggttgc   1320 tgactacata cccttcaacc acgagcacat cacagccaat ttcacacagt actaacgaag   1380
aggtgggttc agcttctatc aaacatctcc aaaggatggg tgaaattttt tccacttcat   1440
tttaaatcta tgcaaaaaag cgaatgcctg tgatgctacc atattcctgg taaaaacatg   1500
gagaaccact atgtagaata aaaatgcaaa gttcactgga gtctcaacat ctatgactca   1560
tgaaaataaa attttcatct tctc   1584

<210> SEQ ID NO 32
<211> LENGTH: 1537
<212> TYPE: DNA
<213> ORGANISM: Homo sapiens

<400> SEQUENCE: 32
gctctcatta ccttctgccc atcacttaat aaatagccag ccaattcatc aacattctgg     60
tacactgttg gagagatgag acagtcacac cagctgcccc tagtggggct cttactgttt    120
tcttttattc caagccaact atgcgagatt tgtgaggtaa gtgaagaaaa ctacatccgc    180
ctaaaacctc tgttgaatac aatgatccag tcaaactata acaggggaac cagcgctgtc    240
aatgttgtgt tgtccctcaa acttgttgga atccagatcc aaaccctgat gcaaaagatg    300
atccaacaaa tcaaatacaa tgtgaaaagc agattgtcag atgtaagctc gggagagctt    360
gccttgatta tactggcttt gggagtatgt cgtaacgctg aggaaaactt aatatatgat    420
taccacctga ctgacaagct agaaaataaa ttccaagcag aaattgaaaa tatggaagca    480
cacaatggca ctcccctgac taactactac cagctcagcc tggacgtttt ggccttgtgt    540
ctgttcaatg ggaactactc aaccgccgaa gttgtcaacc acttcactcc tgaaaataaa    600
aactattatt ttggtagcca gttctcagta gatactggtg caatggctgt cctggctctg    660
acctgtgtga agaagagtct aataaatggg cagatcaaag cagatgaagg cagtttaaag    720
aacatcagta tttatacaaa gtcactggta gaaaagattc tgtctgagaa aaagaaaaat    780
ggtctcattg gaaacacatt tagcacagga gaagccatgc aggccctctt tgtatcatca    840
gactattata tgaaaatga ctggaattgc aacaaactc tgaatacagt gctcacggaa     900
atttctcaag gagcattcag taatccaaac gctgcagccc aggtcttacc tgccctgatg    960
ggaaagacct tcttggatat taacaaagac tcttcttgcg tctctgcttc aggtaacttc   1020
aacatctccg ctgatgagcc tataactgtg acacctcctg actcacaatc atatatctcc   1080
```

| | |
|---|---|
| gtcaattact ctgtgagaat caatgaaaca tatttcacca atgtcactgt gctaaatggt | 1140 |
| tctgtcttcc tcagtgtgat ggagaaagcc cagaaaatga atgatactat atttggtttc | 1200 |
| acaatggagg agcgctcatg ggggccctat atcacctgta ttcagggcct atgtgccaac | 1260 |
| aataatgaca gaacctactg ggaacttctg agtggaggcg aaccactgag ccaaggagct | 1320 |
| ggtagttacg ttgtccgcaa tggagaaaac ttggaggttc gctggagcaa atactaataa | 1380 |
| gcccaaactt tcctcagctg cataaaatcc atttgcagtg gagttccatg tttattgtcc | 1440 |
| ttatgccttc ttcttcattt atcccagtac gagcaggaga gttaataacc tccccttctc | 1500 |
| tctctacatg ttcaataaaa gttgttgaaa gattaac | 1537 |

<210> SEQ ID NO 33
<211> LENGTH: 1866
<212> TYPE: DNA
<213> ORGANISM: Homo sapiens

<400> SEQUENCE: 33

| | |
|---|---|
| ccgattcttg ctcactgctc acccacctgc tgctgccatg aggcaccttg gggccttcct | 60 |
| cttccttctg ggggtcctgg gggccctcac tgagatgtgt gaaataccag agatggacag | 120 |
| ccatctggta gagaagttgg gccagcacct cttaccttgg atggaccggc tttccctgga | 180 |
| gcacttgaac cccagcatct atgtgggcct acgcctctcc agtctgcagg ctgggaccaa | 240 |
| ggaagacctc tacctgcaca gcctcaagct tggttaccag cagtgcctcc tagggtctgc | 300 |
| cttcagcgag gatgacggtg actgccaggg caagccttcc atgggccagc tggccctcta | 360 |
| cctgctcgct ctcagagcca actgtgagtt tgtcaggggc cacaaggggg acaggctggt | 420 |
| ctcacagctc aaatggttcc tgaggatgga agagagcc attgggcatg atcacaaggg | 480 |
| ccaccccac actagctact accagtatgg cctgggcatt ctggccctgt gtctccacca | 540 |
| gaagcgggtc catgacagcg tggtggacaa acttctgtat gctgtggaac ctttccacca | 600 |
| gggccaccat tctgtggaca cagcagccat ggcaggcttg gcattcacct gtctgaagcg | 660 |
| ctcaaacttc aaccctggtc ggagacaacg gatcaccatg gccatcagaa cagtgcgaga | 720 |
| ggagatcttg aaggcccaga cccccgaggg ccactttggg aatgtctaca gcaccccatt | 780 |
| ggcattacag ttcctcatga cttcccccat gcctggggca gaactgggaa cagcatgtct | 840 |
| caaggcgagg gttgctttgc tggccagtct gcaggatgga gccttccaga atgctctcat | 900 |
| gatttcccag ctgctgcccg ttctgaacca caagacctac attgatctga tcttcccaga | 960 |
| ctgtctggca ccacgagtca tgttggaacc agctgctgag accattcctc agacccaaga | 1020 |
| gatcatcagt gtcacgctgc aggtgcttag tctcttgccg ccgtacagac agtccatctc | 1080 |
| tgttctggcc gggtccaccg tggaagatgt cctgaagaag gcccatgagt taggaggatt | 1140 |
| cacatatgaa acacaggcct cctcgtcagg cccctactta acctccgtga tggggaaagc | 1200 |
| ggccggagaa agggagttct ggcagcttct ccgagacccc aacacccac tgttgcaagg | 1260 |
| tattgctgac tacagaccca aggatggaga aaccattgag ctgaggctgg ttagctggta | 1320 |
| gccctgagc tccctcatcc cagcagcctc gcacactccc taggcttcta ccctccctcc | 1380 |
| tgatgtccct ggaacaggaa ctcgcctgac cctgctgcca cctcctgtgc actttgagca | 1440 |
| atgcccctg ggatcacccc agccacaagc ccttcgaggg ccctatacca tggcccacct | 1500 |
| tggagcagag agccaagcat cttccctggg aagtctttct ggccaagtct ggccagcctg | 1560 |
| gccctgcagg tctcccatga aggccacccc atggtctgat gggcatgaag catctcagac | 1620 |
| tccttggcaa aaaacggagt ccgcaggccg caggtgttgt gaagaccact cgttctgtgg | 1680 |

```
ttggggtcct gcaagaaggc ctcctcagcc cgggggctat ggccctgacc ccagctctcc   1740
actctgctgt tagagtggca gctctgagct ggttgtggca cagtagctgg ggagacctca   1800
gcagggctgc tcagtgcctg cctctgacaa aattaaagca ttgatggcct gtggacctgc   1860
aaaaaa                                                              1866

<210> SEQ ID NO 34
<211> LENGTH: 2798
<212> TYPE: DNA
<213> ORGANISM: Homo sapiens

<400> SEQUENCE: 34
gccctctccc acagcggagt ccaaaacagg cctaccagtc agttcttatt tctattgggt     60
gtttccatgc tccaccatgt taagagctaa gaatcagctt tttttacttt cacctcatta    120
cctgaggcag gtaaaagaat catcaggctc caggctcata cagcaacgac ttctacacca    180
gcaacagccc cttcacccag aatgggctgc cctggctaaa aagcagctga aaggcaaaaa    240
cccagaagac ctaatatggc acaccccgga agggatctct ataaaaccct tgtattccaa    300
gagagatact atggacttac ctgaagaact tccaggagtg aagccattca cacgtggacc    360
atatcctacc atgtatacct ttaggccctg gaccatccgc cagtatgctg gtttttagtac   420 tgtggaagaa agcaataagt tctataagga caacattaag gctggtcagc agggattatc    480
agttgccttt gatctggcga cacatcgtgg ctatgattca gacaaccctc gagttcgtgg    540
tgatgttgga atggctggag ttgctattga cactgtggaa gataccaaaa ttcttttttga   600 tggaattcct ttagaaaaaa tgtcagtttc catgactatg aatggagcag ttattccagt    660
tcttgcaaat tttatagtaa ctggagaaga acaaggtgta cctaaagaga aacttactgg    720
taccatccaa aatgatatac taaaggaatt tatggttcga aatacataca ttttttcctcc   780 agaaccatcc atgaaaatta ttgctgacat atttgaatat acagcaaagc acatgccaaa    840
atttaattca atttcaatta gtggatacca tatgcaggaa gcaggggctg atgccattct    900
ggagctggcc tatactttag cagatggatt ggagtactct agaactggac tccaggctgg    960
cctgacaatt gatgaatttg caccaaggtt gtctttcttc tggggaattg gaatgaattt   1020
ctatatggaa atagcaaaga tgagagctgg tagaagactc tgggctcact taatagagaa   1080
aatgtttcag cctaaaaact caaaatctct tcttctaaga gcacactgtc agacatctgg   1140
atggtcactt actgagcagg atccctacaa taatattgtc cgtactgcaa tagaagcaat   1200
ggcagcagta tttggaggga ctcagtcttt gcacacaaat tcttttgatg aagctttggg   1260
tttgccaact gtgaaaagtg ctcgaattgc caggaacaca caaatcatca ttcaagaaga   1320
atctgggatt cccaaagtgg ctgatccttg gggaggttct tacatgatgg aatgtctcac   1380
aaatgatgtt tatgatgctg ctttaaagct cattaatgaa attgaagaaa tgggtggaat   1440
ggccaaagct gtagctgagg gaatacctaa acttcgaatt gaagaatgtg ctgcccgaag   1500
acaagctaga atagattctg ttctgaagt aattgttgga gtaaataagt accagttgga   1560
aaaagaagac gctgtagaag ttctggcaat tgataatact tcagtgcgaa acaggcagat   1620
tgaaaaactt aagaagatca aatccagcag ggatcaagct ttggctgaac attgtcttgc   1680
tgcactaacc gaatgtgctg ctagcggaga tggaaatatc ctggctcttg cagtggatgc   1740
atctcgggca agatgtacag tgggagaaat cacagatgcc ctgaaaaagg tatttggtga   1800
acataaagcg aatgatcgaa tggtgagtgg agcatatcgc caggaatttg agaaagtaa   1860 agagataaca tctgctatca agagggttca taaattcatg gaacgtgaag gtcgcagacc  1920
```

-continued

```
tcgtcttctt gtagcaaaaa tgggacaaga tggccatgac agaggagcaa aagttattgc      1980
tacaggattt gctgatcttg gttttgatgt ggacataggc cctcttttcc agactcctcg      2040
tgaagtggcc cagcaggctg tggatgcgga tgtgcatgct gtgggcgtaa gcaccctcgc      2100
tgctggtcat aaaaccctag ttcctgaact catcaaagaa cttaactccc ttggacggcc      2160
agatattctt gtcatgtgtg gaggggtgat accacctcag gattatgaat ttctgtttga      2220
agttggtgtt tccaatgtat ttggtcctgg gactcgaatt ccaaaggctg ccgttcaggt      2280
gcttgatgat attgagaagt gtttggaaaa gaagcagcaa tctgtataat atcctctttt      2340
tgttttagct tttgtctaaa atattatttt agttatgatc aaagaagaga gtaaagctat      2400
gtcttcaatt taatttcaat acctgatttg tactttcctt gaaagcttta ctttaaaata      2460
ccttacttat aggcctggtg tcatgctata agtatgtaca tacagtttca cttcaaaaat      2520
aaaaaaaaat ccctaaaaac tctctatact ctctataaca atactttatc aagaactctg      2580
gacaatggta ttatttttaa aaatcatggt gatgtattta ttagaatgtt tcttataaat      2640
ctctttcatt tttatattaa gaattaaact gtacctaaaa aaactctgac tattcccatt      2700
tctcagttta gcattacatt gtcttgagca ccagaaaata aaatccatat attaattaaa      2760
acctatcttg aaaaaaaaaa aaaaaaaaaa aaaaaaaa                              2798

<210> SEQ ID NO 35
<211> LENGTH: 1637
<212> TYPE: DNA
<213> ORGANISM: Homo sapiens

<400> SEQUENCE: 35
aagaactggc ctgtacattt tcaaggaatt cttgagaggt tcttggagag attctgggag        60
ccaaacactc cattgggatc ctagctgttt tagagaacaa cttgtaatgg agccttcatc       120
tcttgagctg ccggctgaca cagtgcagcg cattgcggct gaactcaaat gccacccaac       180
ggatgagagg gtggctctcc acctagatga ggaagataag ctgaggcact tcagggagtg       240
cttttatatt cccaaaatac aggatctgcc tccagttgat ttatcattag tgaataaaga       300
tgaaaatgcc atctatttct tgggaaattc tcttggcctt caaccaaaaa tggttaaaac       360
atatcttgaa gaagaactag ataagtgggc caaaatagca gcctatggtc atgaagtggg       420
gaagcgtcct tggattacag agatgagag tattgtaggc cttatgaagg acattgtagg       480
agccaatgag aaagaaatag ccctaatgaa tgctttgact gtaaatttac atcttctaat       540
gttatcattt tttaagccta cgccaaaacg atataaaatt cttctagaag ccaaagcctt       600
cccttctgat cattatgcta ttgagtcaca actacaactt cacggactta acattgaaga       660
aagtatgcgg atgataaagc caagagaggg ggaagaaacc ttaagaatag aggatatcct       720
tgaagtaatt gagaaggaag gagactcaat tgcagtgatc ctgttcagtg gggtgcattt       780
ttacactgga cagcacttta atattcctgc catcacaaaa gctggacaag cgaagggttg       840
ttatgttggc tttgatctag cacatgcagt tggaaatgtt gaactctact tacatgactg       900
gggagttgat tttgcctgct ggtgttccta caagtattta aatgcaggag caggaggaat       960
tgctggtgcc ttcattcatg aaaagcatgc ccatacgatt aaacctgcat tagtgggatg      1020
gtttggccat gaactcagca ccagatttaa gatggataac aaactgcagt taatccctgg      1080
ggtctgtgga ttccgaattt caaatcctcc cattttgttg gtctgttcct tgcatgctag      1140
tttagagatc tttaagcaag cgacaatgaa ggcattgcgg aaaaaatctg ttttgctaac      1200
tggctatctg gaatacctga tcaagcataa ctatggcaaa gataaagcag caaccaagaa      1260
```

-continued

```
accagttgtg aacataatta ctccgtctca tgtagaggag cgggggtgcc agctaacaat    1320
aacattttct gttccaaaca aagatgtttt ccaagaacta gaaaaaagag gagtggtttg    1380
tgacaagcgg aatccaaatg gcattcgagt ggctccagtt cctctctata attctttcca    1440
tgatgtttat aaatttacca atctgctcac ttctatactt gactctgcag aaacaaaaaa    1500
ttagcagtgt tttctagaac aacttaagca aattatactg aaagctgctg tggttatttc    1560
agtattattc gattttaat tattgaaagt atgtcaccat tgaccacatg taactaacaa    1620
taaataatat accttac                                                   1637
```

<210> SEQ ID NO 36
<211> LENGTH: 1908
<212> TYPE: DNA
<213> ORGANISM: Homo sapiens

<400> SEQUENCE: 36

```
gaattcatga aaacgtagct cgtcctcaaa aaaaacagaa gaggagtaat cattttaagg      60
gagaaatata tacgaaagga acaagatttt gaagcaccca agctgccacc tacattaaaa     120
cacggtaggt ggctaaacac cagtcttcaa tgcccttcca cagcctcagt ctgaaaaata     180
ctgtgcaggt gacccaagtg aggggtcacc cttgggcttt tcctgtggca gtatctctgg     240
tttaaaaaca aacaaacgta cttattgcgt tgaaggacgg caacaggaag gactccatga     300
ttagtcacat ctataccatc ctaagaaact ttatccaccc aaactgtatt tcagacttta     360
taatctaaac tacaaaaagt gttcactggg gaactgcaca atatgactgc ttttaaccgt     420
agtgatttca aatattgagc catgctgttg cagtcttaaa aactggagac ctaagggcag     480 cttttcttcta gtcacccaat ccagcacttt ttttaaaaaat cagtaaaact cttcgaccac     540
caaggaaaaa aaaaaggat ggaggttaaa agacgcaccc cttgcccaca agcccctca      600 tcagaatggg agtcaggaga cctgagttcc tgtctcaggc ctgccattaa aaacctgcat     660
aacctttgcc tatctcctca aacggaagta ctaaaaccto agcgcttcac ccaatttgta     720
gccccggctg ggctcttccc accttcccct tcttcagccc gccccttcct cctccagccc     780
tatcatcggg cggagggtcc ccgcctccgc ccgccttacc cacaagcccc gccccccag      840 ccccgatggc cctgcccagt cccagacaga acctactacg tgcggcggca gctgggggcgg    900 gaaggcgggc gctgggggcg ctgcggccgc tgcagcgcag ggtccacctg gtcggctgca     960
cctgtggagg aggaggtgga tttcaggctt cccgtagact ggaagaatcg gctcaaaacc    1020
gcttgcctcg caggggctga gctggaggca gcgaggccgc ccgacgcagg cttccggcga    1080
gacatggcag ggcaaggatg gcagcccggc ggcagggccc ggcgaggagc gcgaacccgc    1140
ggccgcagtt cccaggcgtc tgcgggcgcg agcacgccgc gacctgcgt gcgccggggc      1200 gggggggcgg ggcctcgcct gcacaaatag ggacgagggg gcgggcggc cacaatttcg     1260 cgccaaactt gaccgcgcgt tctgctgtaa cgagcgggct cggaggtcct cccgctgctg    1320
tcatggttgg ttcgctaaac tgcatcgtcg ctgtgtccca gaacatgggc atcggcaaga    1380
acggggacct gccctggcca ccgctcaggt atctgccggg ccggggcgat gggacccaaa    1440
cgggcgcagg ctgcccacgg tcggggtacc tgggcgggac gcgccggccg actccggcg     1500 agaggatggg gccagacttg cggtctgcgc tggcaggaag ggtgggccccg actggattcc    1560 ccttttctgc tgcgcgggag gcccagttgc tgatttctgc ccggattctg ctgcccggtg    1620
aggtcttgcc ctgcggcgcc ctcgcccagg gcaaagtccc agccctggag aaaacacctc    1680
acccctaccc acagcgctcc gtttgtcagg tgccttagag ctcgagccca agggataatg    1740
```

```
tttcgagtaa cgctgtttct ctaacttgta ggaatgaatt cagatatttc cagagaatga    1800
ccacaacctc ttcagtagaa ggtaatgtgg gattaagtag ggtcttgctt gatgaagttt    1860
accagtgcaa atgttagtta aatggaaagt tttccgtgtt aatctggg                 1908
```

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 37

```
cccacggtcg gggtggccga ctcccggcga                                       30
```

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 38

```
ctaaactgca tcgtcgctgt g                                                21
```

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 39

```
aaaagggaa tccagtcgg                                                    19
```

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence:PCR product

<400> SEQUENCE: 40

```
acctgggcgg gacgcgcca                                                   19
```

<210> SEQ ID NO 41
<211> LENGTH: 1275
<212> TYPE: DNA
<213> ORGANISM: Homo sapiens

<400> SEQUENCE: 41

```
ctgcagcgcc agggtccacc tggtcggctg cacctgtgga ggaggaggtg gatttcaggc      60
ttcccgtaga ctggaagaat cggctcaaaa ccgcttgcct cgcaggggct gagctggagg     120
cagcgaggcc gcccgacgca ggcttccggc gagacatggc agggcaagga tggcagcccg     180
gcggcagggc ccggcgagga gcgcgaaccc gcggccgcag ttcccaggcg tctgcgggcg     240
cgagcacgcc gcgaccctgc gtgcgccggg gcgggggggc ggggcctcgc ctgcacaaat     300
agggacgagg gggcggggcg gccacaattt cgcgccaaac ttgaccgcgc gttctgctgt     360
aacgagcggg ctcggaggtc ctcccgctgc tgtcatggtt ggttcgctaa actgcatcgt     420
cgctgtgtcc cagaacatgg gcatcggcaa gaacggggac ctgccctggc caccgctcag     480
gtatctgccg ggccggggcg atgggaccca aacgggcgca ggctgcccac ggtcgggta      540
```

| | |
|---|---|
| cctgggcggg acgcgccagg ccgactcccg gcgagaggat ggggccagac ttgcggtctg | 600 |
| cgctggcagg aagggtgggc ccgactggat tcccctttc tgctgcgcgg gaggcccagt | 660 |
| tgctgatttc tgcccggatt ctgctgcccg gtgaggtctt tgccctgcgg cgccctcgcc | 720 |
| cagggcaaag tcccagccct ggagaaaaca cctcacccct acccacagcg ctccgtttgt | 780 |
| caggtgcctt agagctcgag cccaagggat aatgtttcga gtaacgctgt ttctctaact | 840 |
| tgtaggaatg aattcagata tttccagaga atgaccacaa cctcttcagt agaaggtaat | 900 |
| gtgggattaa gtagggtctt gcttgatgaa gtttaccagt gcaaatgtta gttaaatgga | 960 |
| aagttttccg tgttaatctg ggaccttttc tcttattatg gatctgtatg atctgtatgc | 1020 |
| agttcccaag gttcatttac cattattaaa aaattttgt cttagaaatt ttatgtatgt | 1080 |
| caacgcacga gcaaattatc aggcatgggg cagaattggc aactgggtgg aggcttcggt | 1140 |
| ggaggttagc actccgaaag gaaaacagag taggcctttg gaacagctgc tggaagagat | 1200 |
| aaggcctgaa caagggcagt ggagaagaga gggtaaaaat ttttttaaggt tacatgaccc | 1260 |
| tggattttgg agatc | 1275 |

<210> SEQ ID NO 42
<211> LENGTH: 1256
<212> TYPE: DNA
<213> ORGANISM: Homo sapiens

<400> SEQUENCE: 42

| | |
|---|---|
| ctgcagcgcc agggtccacc tggtcggctg cacctgtgga ggaggaggtg gatttcaggc | 60 |
| ttcccgtaga ctggaagaat cggctcaaaa ccgcttgcct cgcaggggct gagctggagg | 120 |
| cagcgaggcc gcccgacgca ggcttccggc gagacatggc agggcaagga tggcagcccg | 180 |
| gcggcagggc ccgcgagga gcgcgaaccc gcggccgca ttcccaggcg tctgcgggcg | 240 |
| cgagcacgcc gcgaccctgc gtgcgccggg gcggggggc ggggcctcgc ctgcacaaat | 300 |
| agggacgagg gggcggggcg gccacaattt cgcgccaaac ttgaccgcgc gttctgctgt | 360 |
| aacgagcggg ctcggaggtc ctcccgctgc tgtcatggtt ggttcgctaa actgcatcgt | 420 |
| cgctgtgtcc cagaacatgg gcatcggcaa gaacggggac ctgccctggc caccgctcag | 480 |
| gtatctgccg ggccggggcg atgggaccca acgggcgca ggctgcccac ggtcggggtg | 540 |
| gccgactccc ggcgagagga tggggccaga cttgcggtct cgctggcag gaagggtggg | 600 |
| cccgactgga ttcccctttt ctgctgcgcg ggaggcccag ttgctgattt ctgcccggat | 660 |
| tctgctgccc ggtgaggtct ttgccctgcg gcgccctcgc ccagggcaaa gtcccagccc | 720 |
| tggagaaaac acctcacccc tacccacagc gctccgtttg tcaggtgcct tagagctcga | 780 |
| gcccaaggga taatgtttcg agtaacgctg tttctctaac ttgtaggaat gaattcagat | 840 |
| atttccagag aatgaccaca acctcttcag tagaaggtaa tgtgggatta agtagggtct | 900 |
| tgcttgatga agtttaccag tgcaaatgtt agttaaatgg aaagttttcc gtgttaatct | 960 |
| gggaccttt ctcttattat ggatctgtat gatctgtatg cagttcccaa ggttcattta | 1020 |
| ccattattaa aaattttgt tcttagaaat tttatgtatg tcaacgcacg agcaaattat | 1080 |
| caggcatggg gcagaattgg caactgggtg gaggcttcgg tggaggttag cactccgaaa | 1140 |
| ggaaaacaga gtaggccttt ggaacagctg ctggaagaga taaggcctga acaagggcag | 1200 |
| tggagaagag agggtaaaaa tttttttaagg ttacatgacc ctggattttg gagatc | 1256 |

<210> SEQ ID NO 43
<211> LENGTH: 55
<212> TYPE: DNA

```
<213> ORGANISM: Artificial Sequence
<220> FEATURE:
<223> OTHER INFORMATION: Description of Artificial Sequence:PCR product

<400> SEQUENCE: 43
gctgcccacg gtcggggtac ctgggcggga cgcgccaggc cgactcccgg cgaga        55

<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence:PCR product

<400> SEQUENCE: 44
gctgcccacg gtcggggtgg ccgactcccg gcgaga                              36

<210> SEQ ID NO 45
<211> LENGTH: 1273
<212> TYPE: DNA
<213> ORGANISM: Homo sapiens

<400> SEQUENCE: 45
ctgcagcgca gggtccacct ggtcggctgc acctgtggag gaggaggtgg atttcaggct    60
tcccgtagac tggaagaatc ggctcaaaac cgcttgcctc gcaggggctg agctggaggc   120
agcgaggccg cccgacgcag gcttccggcg agacatggca gggcaaggat ggcagcccgg   180
cggcagggcc cggcgaggag cgcgaacccg cggccgcagt tcccaggcgt ctgcgggcgc   240
gagcacgccg cgaccctgcg tgcgccgggg cgggggggcg gggcctcgcc tgcacaaata   300
gggacgaggg ggcggggcgg ccacaatttc gcgccaaact tgaccgcgcg ttctgctgta   360
acgagcgggc tcggaggtcc tcccgctgct gtcatggttg gttcgctaaa ctgcatcgtc   420
gctgtgtccc agaacatggg catcggcaag aacggggacc tgccctggcc accgctcagg   480
tatctgccgg gccggggcga tgggacccaa acgggcgcag gctgcccacg gtcggggtac   540
ctgggcggga cgcgccggcc gactcccggc gagaggatgg ggccagactt gcggtctgcg   600
ctggcaggaa gggtgggccc gactggattc cccttttctg ctgcgcggga ggcccagttg   660
ctgatttctg cccggattct gctgcccggt gaggtctttg ccctgcggcg ccctcgccca   720
gggcaaagtc ccagccctgg agaaaacacc tcaccccctac ccacagcgct ccgtttgtca   780
ggtgccttag agctcgagcc caagggataa tgtttcgagt aacgctgttt ctctaacttg   840
taggaatgaa ttcagatatt tccagagaat gaccacaacc tcttcagtag aaggtaatgt   900
gggattaagt agggtcttgc ttgatgaagt ttaccagtgc aaatgttagt taaatggaaa   960
gttttccgtg ttaatctggg accttttctc ttattatgga tctgtatgat ctgtatgcag  1020
ttcccaaggt tcatttacca ttattaaaaa attttgtct tagaaatttt atgtatgtca   1080
acgcacgagc aaattatcag gcatggggca gaattggcaa ctgggtggag gcttcggtgg  1140
aggttagcac tccgaaagga aaacagagta ggcctttgga acagctgctg gaagagataa  1200
ggcctgaaca agggcagtgg agaagagagg gtaaaaattt tttaaggtta catgacccctg 1260 gattttggag atc                                                    1273

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence:PCR product
```

```
<400> SEQUENCE: 46
acctgggcgg gacgcgcc                                          18
```